United States Patent
Kondo et al.

(10) Patent No.: US 11,066,665 B2
(45) Date of Patent: *Jul. 20, 2021

(54) ANTITUMOR DRUG DELIVERY FORMULATION

(71) Applicants: PUBLIC UNIVERSITY CORPORATION NAGOYA CITY UNIVERSITY, Nagoya (JP); THE UNIVERSITY OF TOKYO, Tokyo (JP)

(72) Inventors: Yutaka Kondo, Nagoya (JP); Keisuke Katsushima, Nagoya (JP); Kazunori Kataoka, Tokyo (JP); Kanjiro Miyata, Tokyo (JP); Hyun Jin Kim, Tokyo (JP)

(73) Assignees: PUBLIC UNIVERSITY CORPORATION NAGOYA CITY UNIVERSITY, Aichi (JP); THE UNIVERSITY OF TOKYO, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/777,498

(22) PCT Filed: Nov. 18, 2016

(86) PCT No.: PCT/JP2016/084328
§ 371 (c)(1),
(2) Date: May 18, 2018

(87) PCT Pub. No.: WO2017/086467
PCT Pub. Date: May 26, 2017

(65) Prior Publication Data
US 2018/0334674 A1 Nov. 22, 2018

(30) Foreign Application Priority Data
Nov. 19, 2015 (JP) .............................. JP2015-226895

(51) Int. Cl.
| | | |
|---|---|---|
| *C12N 15/11* | (2006.01) | |
| *C12N 15/113* | (2010.01) | |
| *A61K 31/713* | (2006.01) | |
| *A61K 35/76* | (2015.01) | |
| *A61K 31/7088* | (2006.01) | |
| *C12N 15/00* | (2006.01) | |
| *A61K 9/00* | (2006.01) | |
| *A61K 47/60* | (2017.01) | |
| *A61P 35/00* | (2006.01) | |
| *A61K 9/107* | (2006.01) | |

(52) U.S. Cl.
CPC .......... *C12N 15/113* (2013.01); *A61K 9/0019* (2013.01); *A61K 9/1075* (2013.01); *A61K 31/7088* (2013.01); *A61K 31/713* (2013.01); *A61K 35/76* (2013.01); *A61K 47/60* (2017.08); *A61P 35/00* (2018.01); *C12N 15/00* (2013.01); *C12N 2310/11* (2013.01); *C12N 2310/111* (2013.01); *C12N 2310/14* (2013.01); *C12N 2310/3231* (2013.01); *C12N 2310/351* (2013.01); *C12N 2310/3513* (2013.01); *C12N 2320/32* (2013.01)

(58) Field of Classification Search
CPC .............. C12N 15/113; C12N 15/1135; C12N 2310/11
See application file for complete search history.

(56) References Cited

U.S. PATENT DOCUMENTS

| | | |
|---|---|---|
| 2009/0018216 A1 | 1/2009 | Kataoka et al. |
| 2009/0258416 A1 | 10/2009 | Kataoka et al. |
| 2011/0052917 A1 | 3/2011 | Kataoka et al. |
| 2012/0053295 A1 | 3/2012 | Kataoka et al. |
| 2013/0109743 A1 | 5/2013 | Kataoka et al. |
| 2014/0017328 A1 | 1/2014 | Kataoka et al. |
| 2015/0080454 A1 | 3/2015 | Kataoka et al. |
| 2018/0163208 A1 | 6/2018 | Kondo et al. |

FOREIGN PATENT DOCUMENTS

| | | |
|---|---|---|
| EP | 2 213738 A2 | 8/2010 |
| EP | 2 213738 A3 | 11/2010 |
| EP | 2842546 A1 * | 3/2015 |
| JP | 2006 507841 A | 3/2006 |
| JP | WO2007099660 | 7/2009 |

(Continued)

OTHER PUBLICATIONS

Li et al., Long non-coding RNA TUG1 acts as a miR-26a sponge in human glioma cells, BBRC, vol. 477, pp. 743-748. (Year: 2016).*

(Continued)

*Primary Examiner* — Dana H Shin
(74) *Attorney, Agent, or Firm* — Brinks Gilson & Lione

(57) ABSTRACT

This invention provides an antitumor drug delivery formulation for treating a subject having a tumor more highly expressing a TUG1 gene than normal tissues or preventing the subject from tumor metastasis, comprising a polymeric micelle comprising a nucleic acid that suppresses high expression of the TUG1 gene as an active ingredient, wherein the polymeric micelle comprises a block copolymer having a cationic poly(amino acid) segment and a hydrophilic polymer chain segment and the nucleic acid, and wherein the nucleic acid is bound to a cationic group of the cationic poly(amino acid) segment to form a complex and/or the nucleic acid is incorporated in the micelle or attached into the micelle; and the polymeric micelle accumulates in the tumor.

17 Claims, 18 Drawing Sheets
Specification includes a Sequence Listing.

(56) References Cited

FOREIGN PATENT DOCUMENTS

| | | |
|---|---|---|
| JP | WO2007099661 | 7/2009 |
| JP | WO2009113645 | 7/2011 |
| JP | WO2010093036 | 8/2012 |
| JP | WO2012005376 | 9/2013 |
| WO | WO2012096399 | 7/2012 |
| WO | WO2013162041 | 10/2013 |
| WO | WO 2016/129633 A1 | 8/2016 |

OTHER PUBLICATIONS

Grünweller et al., Comparison of different antisense strategies in mammalian cells using locked nucleic acids, 2'-O-methyl RNA, phosphorothioates and small interfering RNA, Nucleic Acids Research, vol. 31, pp. 3185-3193. (Year: 2003).*

Oe et al., Actively-targeted polyion complex micelles stabilized by cholesterol and disulfide cross-linking for systemic delivery of siRNA to solid tumors, Biometerials, vol. 35, pp. 7887-7895. (Year: 2014).*

Yin et al., Downregulation of lncRNA TUG1 affects apoptosis and insulin secretion in mouse pancreatic beta cells, Cellular Physiology and Biochemistry, vol. 35, pp. 1892-1904. (Year: 2015).*

Young et al. Curr. Biol. 2005;15(6), pp. 501-512.

Zhang et al. Cell Death Dis. 2014, 5, pp. 1-12.

Xu et al. Tumor Biology 2015; 36(3) pp. 1643-1651.

Zhang et al., Asian Pac J Cancer Prev. 2013, 14 (4); pp. 2311-2315.

Han et al.J Surg Oncol, 2013 107(5), pp. 555-559.

Huang, et al. Mol Cancer; 2015; 14(165) pp. 1-12.

Cai et al., Oncotarget, 2015; 6 (23) pp. 19759-19779 (PMID: 26078353).

Sun et al., J Transl Med. 2016 14(42); pp. 1-10 (PMID: 26856330).

Tan et al., FEBS Lett. 2015; pp. 3175-3181 (PMID: 26318860).

Dong et al., Cell Death Dis. 2016; 7; pp. 1-13 (PMID: 27362796).

Ji et al., Asian Pac J Trop Med. 2016; 9 (5); pp. 508-512 (PMID: 27261864).

Jiang et al., Cancer Chemother Pharmacol. 2016; 78; pp. 333-339 (PMID: 27329359).

Kuang et al., Exp Mol Pathol. 2016; 101; pp. 267-273 (PMID: 27693324).

Wang et al., Oncotarget. 2016; 7 (32); pp. 51713-51719 (PMID: 27421138).

Zhai et al., Med Sci Monit. 2016; 22; pp. 3281-3287 (PMID: 27634385).

Zhang et al., Cell Death Dis. 2016; 7; pp. 1-10 (PMID: 26913601).

Zhang et al., J Mol Histol. 2016; 47; pp. 421-428 (PMID: 27323757).

Jones et al.AACR Special Conference, 2015; 2 pages.

Yoshida et al. the 40th Naito Conference, 2015; 3 pages.

Inazawa et al. the 34th Sapporo International Cancer Symposium, 2015; 2 pages.

Kondo et al. the 10th Asian Epigenomics Meeting, 2015; 2 pages.

Sasako et al. JSCO 53rd Annual Meeting of Japan Society of Clinical Oncology 2015 program 50(1); 3 pages.

Hashizume et al., American Journal of Pathology 156(4), 2000, p. 1363-1380.

Japan Patent Office as ISA, International Search Report for Japanese PCT Application No. PCT/JP2016/084328 dated Feb. 21, 2017, 3 pages.

Communication dated Jul. 2, 2019 received in connection with the corresponding European Application No. 16866467.0, including Supplementary European Search Report and Annex to the European Search Report.

Mahmud, A., et al., "Development of Targeted Polyethylene Glycol-poly(L-Lysine) Polyplex for the Delivery of siRNA to Pancreatic Cancer," AAPS, Poster Submission (Jan. 1, 2015); XP055421607.

EM PAT Database Accession No. GB477947, "Functional and Hyperfunctional siRNA," (Jun. 28, 2011).

Office Action received in European Patent Application No. 16866467.0 dated Aug. 18, 2020.

Kim, H.J., et al., "siRNA delivery from triblock copolymer micelles with spatially-ordered compartments of PEG shell, siRNA-loaded intermediate layer, and hydrophobic core," *Biomaterials*, 35:4548-4556 (2014).

Khalil, A.M., et al., "Many human large intergenic noncoding RNAs associate with chromatin-modifying complexes and affect gene expression," *PNAS*, 106(28):11667-11672 (2009).

Supporting Information for: Khalil, A.M., et al., "Many human large intergenic noncoding RNAs associate with chromatin-modifying complexes and affect gene expression," *PNAS*, 106(28):11667-11672 (2009)—10 pages.

\* cited by examiner

Fig. 3A

| Sequence name | Antisense strand (5'→3') | | Sense strand (5'→3') | | Remarks |
|---|---|---|---|---|---|
| si-TUG1 #1 | UGAUUCUUAACUCUCUdTdG | (SEQ ID NO: 28) | CCAGAGAGUUAAGAAUdCdA | (SEQ ID NO: 20) | PNAS106:11667-11672,2009 |
| si-TUG1 #2 | UUACUCUGGGCUUCUGCdAdC | (SEQ ID NO: 29) | GUGCAGAAGCCAGAGUdAdA | (SEQ ID NO: 21) | PNAS106:11667-11672,2009 |
| si-TUG1 #3 | UUGUUCUCUGGCUAUAUCCdCdA | (SEQ ID NO: 30) | GGAUAUAGCCAGAGAACAAdTdT | (SEQ ID NO: 22) | PNAS106:11667-11672,2009 |
| si-TUG1 #4 | ACGAUAAUUCUUCUUAACdAdA | (SEQ ID NO: 31) | GUUAAGAAGAAUUAUCGUdCdA | (SEQ ID NO: 23) | |
| si-TUG1 #5 | AUUAAUAACUAAAAAUCCdCdC | (SEQ ID NO: 32) | GGAUUUUUAGUUAUUAAUdGdC | (SEQ ID NO: 24) | |
| si-TUG1 #6 | UGAAUUUCAAUCAUUUGAGdAdT | (SEQ ID NO: 33) | CUCAAAUGAUGAAAUUCAdTdG | (SEQ ID NO: 25) | |
| si-TUG1 #7 | UUGAAGUAGAAAAAACAGGdGdT | (SEQ ID NO: 34) | CCUGUUUUUCUACUUCAAdAdT | (SEQ ID NO: 26) | |
| si-TUG1 #8 | AGAAUUCUUACAUUUGUGdTdA | (SEQ ID NO: 35) | CACAAAUGUAAGAAAUUCUdAdC | (SEQ ID NO: 27) | |

Fig. 3B

| Sequence name | Antisense strand (5'→3') | | Sense strand (5'→3') | | Remarks |
|---|---|---|---|---|---|
| si-TUG1 #9 | GCCAUUUAAAGAAAACAGUAdCdC | (SEQ ID NO: 45) | UACUGUUUUCUUUAAAUGGCdGdG | (SEQ ID NO: 39) | |
| si-TUG1 #10 | GAUUCAAAGCUAAACUUUUdTdC | (SEQ ID NO: 46) | AAAAGUUUAGCUUUGAAUCdAdC | (SEQ ID NO: 40) | |
| si-TUG1 #11 | CAUAUCAAGAUGCAUUUUAUdTdA | (SEQ ID NO: 47) | AUAAAAUGCAUCUUGAUAUGdTdT | (SEQ ID NO: 41) | |
| si-TUG1 #12 | GGAUUUUUAGUUAUUAAUdGdC | (SEQ ID NO: 48) | AUUAAUAACUAAAAAUCCdCdC | (SEQ ID NO: 42) | |
| si-TUG1 #13 | UAAUCCAUAGGGCUUAUdTdC | (SEQ ID NO: 49) | GAAUAAGCCCUAUGGAUdTdA | (SEQ ID NO: 43) | PNAS106:11667-11672,2009 |
| si-TUG1 #14 | CCCUUUUUGCUUAAGUUAdCdT | (SEQ ID NO: 50) | UAACUUAAGCAAAAAGGGdTdA | (SEQ ID NO: 44) | |

Fig. 6

| Sequence name | Antisense strand (5'→3') | |
|---|---|---|
| LNA-TUG1-1 #1 | UUACUCUGGGCUUCUGCAC | (SEQ ID NO: 36) |
| LNA-TUG1-1 #2 | UUACUCUGGGCUUCUGCAC | (SEQ ID NO: 37) |
| LNA-TUG1-1 #3 | UUACUCUGGGCUUCUGCAC | (SEQ ID NO: 38) |

Fig. 9

| Sequence name | Antisense strand (5'→3') | |
|---|---|---|
| LNA-TUG1-2 #1 | UGAAUUUCAAUCAUUUGAGAU | (SEQ ID NO: 51) |
| LNA-TUG1-2 #2 | UGAAUUUCAAUCAUUUGAGAU | (SEQ ID NO: 52) |
| LNA-TUG1-2 #3 | UGAAUUUCAAUCAUUUGAGAU | (SEQ ID NO: 53) |

Fig. 17
Panel A
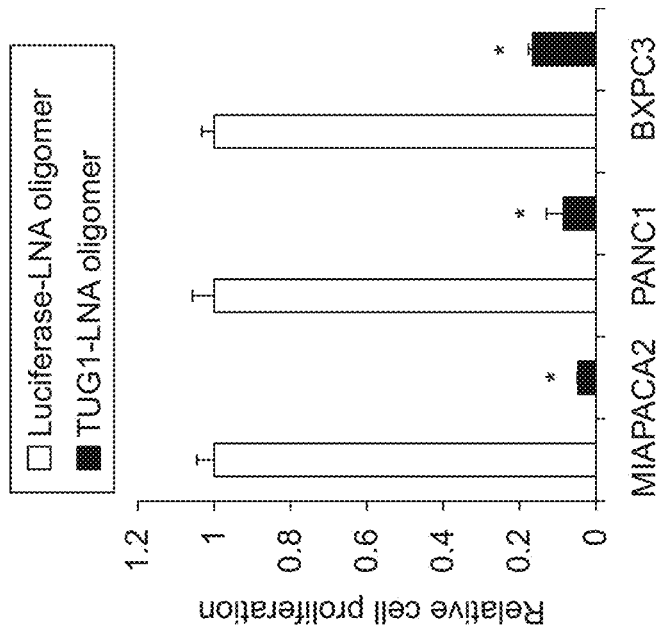
Panel B
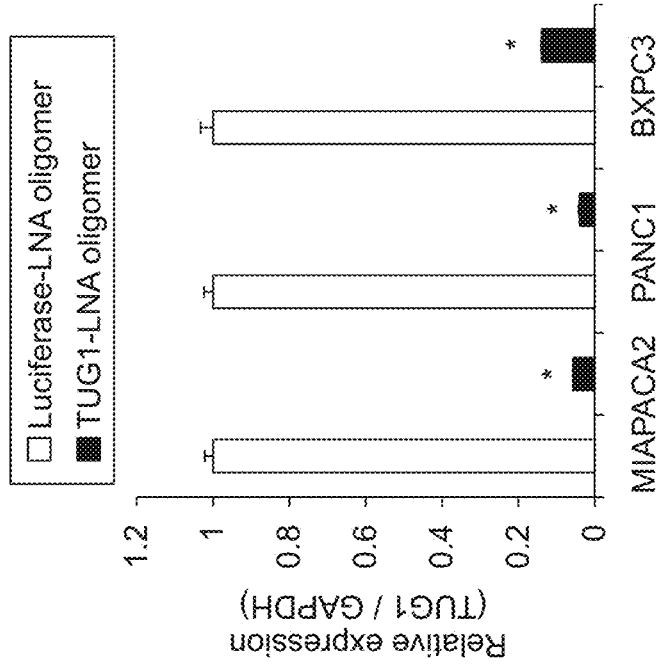

ANTITUMOR DRUG DELIVERY FORMULATION

This application is a 371 application of PCT/JP2016/084328 having an international filing date of Nov. 18, 2016, which claims priority to JP2015-226895 filed Nov. 19, 2015, the entire contents of each of which are incorporated herein by reference.

TECHNICAL FIELD

The present invention relates to antitumor drug delivery formulations for tumors highly expressing a TUG1 gene.

More specifically, the present invention relates to drug delivery formulations comprising a nucleic acid such as a modified siRNA, a modified antisense RNA, or an antisense DNA, each of which effectively suppresses expression of TUG1 in tumor cells.

This application is being filed electronically via EFS-Web and includes an electronically submitted Sequence Listing in .txt format. The .txt file contains a sequence listing entitled "16224_4_Seq_Listing_ST25" created on Jan. 28, 2020 and is 43,078 bytes in size. The sequence listing contained in this .txt file is part of the specification and hereby incorporated by reference in its entirety.

BACKGROUND ART

TUG1 is the abbreviation of taurine upregulated gene 1, which is a spliced polyadenylated RNA, identified by Young et al. (Non-Patent Literature 1) as being a non-coding RNA necessary for the differentiation of the rodent retina and highly expressed in tissues of the nervous system including retina and the brain.

With regard to the role of TUG1 in cancer or tumors, for example, it is disclosed by Zhang et al. (Non-Patent Literature 2) that knocking down of TUG1 in non-small-cell lung carcinoma (NSCLC) promotes the cell proliferation. In contrast, it is also reported that TUG1 is overexpressed in particular cancers or tumors and when the TUG1 expression is suppressed, then the proliferation of the cancers or tumors are suppressed. For example, Xu et al. (Non-Patent Literature 3) discloses that TUG1 silencing suppresses the proliferation of esophageal squamous cell carcinoma (ESCC) cells and prevents the progression of the cell cycle. Moreover, Zhang et al. (Non-Patent Literature 4) discloses that TUG1 is overexpressed in osteosarcoma cell lines and that the suppression of the TUG1 expression causes apoptosis of osteosarcoma cells. Furthermore, Han et al. (Non-Patent Literature 5) discloses that TUG1 is overexpressed in urothelial carcinoma and is associated with high stage carcinomas and that silencing of TUG1 causes the inhibition of proliferation and the induction of apoptosis.

Glioblastoma multiforme (GBM), which has the highest grade of malignancy among the primary brain tumors, is a tumor that is still very difficult to achieve a radical cure. GBM has epigenomic abnormalities such as untranslated RNAs, histone modification, and DNA methylation in addition to genomic abnormalities and these epigenomic abnormalities are suggested to contribute to malignant progression of the GBM. The control of gene expression with long non-coding RNA (lncRNA), which is one of the untranslated RNAs, is deeply involved in various biological phenomena such as differentiation and proliferation of cells and its involvement in the malignant progression of cancers has also been reported. Based on such findings, the research and development of therapies for intractable tumoral diseases such as GBM have been conducted, but no innovative technology has been found.

A promising technology having attracted attention in recent years particularly in terms of practicability is the polymeric micelle drug delivery system developed by Kataoka et al. This technology comprises, for example, incorporating an agent in micelles formed from block copolymers containing a hydrophilic block and a cationic amino acid block (Patent Literatures 1 to 6, etc.). Tumor is among the diseases to which this technology can be applied, but what kind of agent is to be contained, as well as the therapeutic effect, is largely dependent on future studies.

PRIOR ART LITERATURE

Patent Literature

Patent Literature 1: JP WO 2007/099660
Patent Literature 2: JP WO 2007/099661
Patent Literature 3: JP WO 2009/113645
Patent Literature 4: WO2013/162041
Patent Literature 5: JP WO 2010/093036
Patent Literature 6: JP WO 2012/005376

Non-Patent Literature

Non-Patent Literature 1: T. L. Young et al., Curr. Biol., 2005, 15 (6) 501-512:
Non-Patent Literature 2: E. B. Zhang et al., Cell Death Dis. May 22, 2014, 5: e1243.doi: 10.1038/cddis.2014.201
Non-Patent Literature 3: Y. Xu et al., Tumor Biology Oct. 31, 2014, doi: 10, 1007/s13277.014.2763.6
Non-Patent Literature 4: Q. Zhang et al., Asian Pacific J Cancer Prev, 2013, 14 (4): 2311-2315
Non-Patent Literature 5: Y. Han et al., J Surg Oncol, 2013, 107:555-559

SUMMARY OF INVENTION

Problem to be Solved by Invention

An object of the present invention is to provide nucleic acid medicaments that can prevent or treat cancers or tumors highly expressing TUG1 including a brain tumor such as glioblastoma multiforme (GBM).

GBM has the highest grade of malignancy among primary brain tumors and is a tumor that is still very difficult to achieve a radical cure (or complete cure), as mentioned above. The GBM has epigenomic abnormalities, such as untranslated RNA, histone modification, and DNA methylation, in addition to genomic abnormalities, and these epigenomic abnormalities are suggested to contribute to malignant progression of GBM.

The present inventors previously found that TUG1, which is one of lncRNAs, is highly expressed in some tumors including GBM and nucleic acids targeting TUG1 are effective for significant regression of the tumors (WO2016/129633A1). The present inventors have now further found antitumor drug delivery formulations that are specifically accumulated in tissues of tumors such as brain tumor and are capable of suppressing the expression of TUG1 and causing the regression of the tumors, thereby completing the present invention.

Means for Solution of Problem

Accordingly, the present invention encompasses the following features.

(1) An antitumor drug delivery formulation for treating a subject having a tumor more highly expressing a TUG1 gene than normal tissues or preventing the subject from tumor metastasis, comprising a polymeric micelle comprising a nucleic acid that suppresses high expression of the TUG1 gene as an active ingredient; wherein the polymeric micelle comprises a block copolymer having a cationic poly(amino acid) segment and a hydrophilic polymer chain segment and the nucleic acid, and wherein the nucleic acid is bound to a cationic group of the cationic poly(amino acid) segment to form a complex and/or the nucleic acid is incorporated in the micelle or attached into the micelle; and the polymeric micelle accumulates in the tumor.

(2) The drug delivery formulation according to (1) above, wherein the tumor is brain tumor, pancreatic cancer, breast cancer, colorectal cancer, prostate cancer, liver cancer, lung cancer, leukemia, or lymphoma.

(3) The drug delivery formulation according to (2) above, wherein the tumor is brain tumor or pancreatic cancer.

(4) The drug delivery formulation according to any one of (1) to (3) above, wherein the nucleic acid is an siRNA, a precursor RNA thereof, an antisense RNA, or a modified RNA thereof, or an antisense DNA, to a transcript RNA of a TUG1 gene.

(5) The drug delivery formulation according to any one of (1) to (4) above, wherein the nucleic acid targets a region at nucleotide positions 1044 to 1062, 1044 to 1062, or 1044 to 1062 and/or a region at nucleotide positions 2997 to 5181, 2941 to 5111, or 2941 to 5125, respectively, in the nucleotide sequence of SEQ ID NO: 1, 2, or 3 of the transcript RNA of the TUG1 gene.

(6) The drug delivery formulation according to any one of (1) to (5) above, wherein the nucleic acid is any one or a combination of two or more of siRNAs, precursor RNAs, or modified RNAs thereof comprising sense strands consisting of the nucleotide sequences of SEQ ID NOs: 4 to 11 and antisense strands consisting of the nucleotide sequences of SEQ ID NOs: 12 to 19 complementary to the sense strands, respectively.

(7) The drug delivery formulation according to any one of (4) to (6) above, wherein the modified RNA comprises one or more modified nucleotides or deoxyribonucleotides.

(8) The drug delivery formulation according to any one of (4) to (7) above, wherein the modified RNA is an siRNA comprising a sense strand consisting of the nucleotide sequence of any of SEQ ID NOs: 20 to 27 and an antisense strand consisting of the nucleotide sequence of any of SEQ ID NOs: 28 to 35 comprising a sequence complementary to the sense strand, respectively, or an antisense RNA/DNA chimera consisting of the nucleotide sequence of any of SEQ ID NOs: 28 to 35.

(9) The drug delivery formulation according to any one of (4) to (8) above, wherein the modified RNA is an LNA modified antisense RNA comprising at least two LNA modified nucleotides that have a 2'-O, 4'-C methylene bridge and are locked by the bridge on respective end sides.

(10) The drug delivery formulation according to any one of (4) to (5) and (7) to (9) above, wherein the modified RNA is an LNA modified antisense RNA consisting of any of the nucleotide sequences of SEQ ID NOs: 36 to 38 and 51 to 53.

(11) The drug delivery formulation according to any one of (1) to (7) above, wherein the nucleic acid is a vector comprising a DNA encoding an siRNA or a precursor RNA thereof or an antisense RNA, or an antisense DNA, each of them being for the transcript RNA of the TUG1 gene.

(12) The drug delivery formulation according to any one of (1) to (11) above, wherein the hydrophilic polymer chain segment comprises a plurality of branched polymer chains.

(13) The drug delivery formulation according to any one of (1) to (12) above, wherein the cationic poly(amino acid) segment comprises polylysine.

(14) The drug delivery formulation according to any one of (1) to (13) above, wherein the hydrophilic polymer chain segment comprises poly(ethylene glycol) or an end-modified poly(ethylene glycol).

(15) The drug delivery formulation according to any one of (1) to (14) above, wherein the block copolymer comprises a linking group between the cationic poly(amino acid) segment and the hydrophilic polymer chain segment.

(16) The drug delivery formulation according to any one of (1) to (14) above, wherein the hydrophilic polymer chain segment comprises a cyclic peptide comprising the sequence of arginine-glycine-aspartic acid or the sequence of asparagine-glycine-arginine.

(17) The drug delivery formulation according to any one of (1) to (16) above, wherein the block copolymer has an N/P ratio of more than 1, the N/P ratio being defined as [total number of cationic groups in block copolymer (N)]/[total number of phosphate groups in nucleic acid (P)].

(18) The drug delivery formulation according to (17) above, wherein the N/P ratio is 2 or more, 3 or more, 4 or more, or 5 or more.

(19) A method for treating or preventing a tumor more highly expressing a TUG1 gene than normal tissues in a subject having the tumor, comprising administering to the subject the drug delivery formulation according to any one of (1) to (18) above.

(20) The method according to (19) above, wherein the tumor is brain tumor, pancreatic cancer, breast cancer, colorectal cancer, prostate cancer, liver cancer, lung cancer, leukemia, or lymphoma.

The drug delivery formulations according to the present invention have an effect that makes it possible to strongly suppress the proliferation of tumors highly expressing a TUG1 gene in comparison with normal tissues, such as brain tumor, pancreatic cancer, breast cancer, colorectal cancer, prostate cancer, liver cancer, lung cancer, leukemia, and lymphoma.

BRIEF DESCRIPTION OF DRAWINGS

FIG. 3 illustrates the nucleotide sequences (i.e., sense strand sequences and antisense strand sequences) of si-TUG1 #1 to si-TUG1 #14 tested in FIG. 2. The figure illustrates that siRNAs that exhibited the suppressive effect are si-TUG1 #1 to si-TUG1 #8 (FIG. 3A) and si-TUG1 #9 to si-TUG1 #14 exhibited a low suppressive effect or no suppressive effect (FIG. 3B).

FIG. 6 illustrates LNA modified antisense RNAs prepared based on the nucleotide sequence of SEQ ID NO: 13, i.e., LNA-TUG1-1 #1 (SEQ ID NO: 36), LNA-TUG1-1 #2 (SEQ ID NO: 37), and LNA-TUG1-1 #3 (SEQ ID NO: 38). The sites subjected to the LNA modification are indicated with underline.

FIG. 9 illustrates LNA modified antisense RNAs prepared based on the nucleotide sequence of SEQ ID NO: 17, i.e., LNA-TUG1-2 #1 (SEQ ID NO: 51), LNA-TUG1-2 #2 (SEQ ID NO: 52), and LNA-TUG1-2 #3 (SEQ ID NO: 53). The sites subjected to the LNA modification are indicated with underline.

FIG. 12 illustrates a proliferation-suppressive effect of the TUG1 inhibition on the prostate cancer cell line PC3.

FIG. 17 illustrates the proliferation-suppressive effect of the TUG1 inhibition on the pancreatic cancer cell lines (MIAPACA2, PANC1, BXPC3). Panel A illustrates the TUG1 expression levels in the pancreatic cancer cell lines when the TUG1-LNA oligomer (LNA modified antisense DNA, SEQ ID NO: 56) or the LNA oligomer (SEQ ID NO: 57) for Firefly GL3 Luciferase gene was acted on the pancreatic cancer cell lines, and Panel B illustrates the relative cell proliferation rate of the pancreatic cancer cell lines when the respective LNA oligomers acted on the pancreatic cancer cell lines. * indicates statistical significance (p<0.01).

Figure 1:
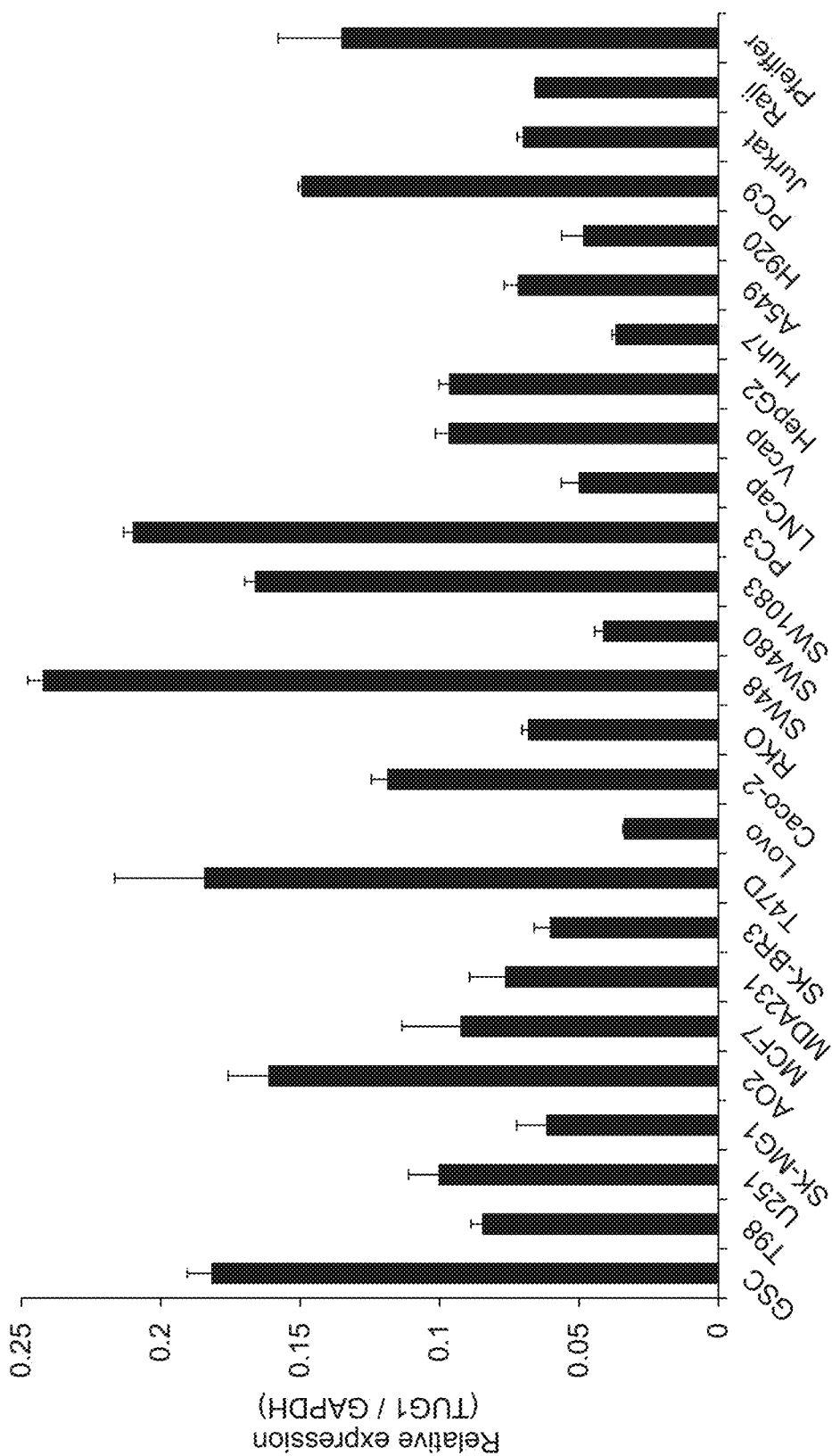
FIG. 1 illustrates expression levels of TUG1 in various tumor cell lines. In the figure, GSC denotes a glioma stem cell line; T98, U251, SK-MG1, and A02 denote glioma cell lines; MCF7, MDA231, SK-BR3, and T47D denote breast cancer cell lines; Lovo, Caco-2, RKO, SW48, SW480, and SW1083 denote colorectal cancer cell lines; PC3, LNCap, and Vcap denote prostate cancer cell lines; HepG2, Huh7, and A549 denote liver cancer cell lines; H920 and PC9 denote lung cancer cell lines; Jurkat denotes a leukemia cell line; Raji denotes a Burkitt lymphoma cell line; and Pfeiffer denotes a lymphoma cell line. The expression levels are represented by the relative expression of TUG1 to the internal standard GAPDH.

The description of this application includes the contents described in the description and/or drawings of Japanese patent application No: 2015-226895 from which the present application claims the priority.

MODE FOR CARRYING OUT THE INVENTION

In recent years, the relationship of the abnormal expression of lncRNA with cancers has attracted attention. In particular, a lot of microRNAs (miRNAs) have been found in the field of cancer diagnosis. Depending on the kind of cancers or tumors, the kind of miRNAs is different and some miRNAs are overexpressed in comparison with those in normal cells and miRNAs that are decreased, on the contrary, are also present, thereby making things complicated. Moreover, in the relationship between lncRNAs and cancers, cases where lncRNAs are overexpressed and cases where the expression of lncRNAs is decreased are both known although reports on lncRNA are less than those on miRNA.

The present inventors have developed therapeutic agents for brain tumors, which are in particular difficult to treat among tumors. Glioblastoma multiforme (GBM), which has the highest grade of malignancy among the primary brain tumors, is a tumor that is very difficult to ameliorate. The GBM have epigenomic abnormalities, such as untranslated RNAs, histone modification, and DNA methylation, in addition to genomic abnormalities, and these epigenomic abnormalities are suggested to contribute to malignant progression of the GBM. The control of the gene expression of lncRNAs, which are a type of the untranslated RNAs mentioned above, is deeply involved in various biological phenomena such as differentiation and proliferation of cells and its involvement in the malignant progression of cancers has also been reported (R. A. Gupta et al., Nature, 464: 1071-1076, 2010; L. Yang et al., Nature, 500: 598-602, 2013; J. H. Yuan et al., Cancer Cell, 25: 666-681, 2014; A. M. Khalil et al., PNAS, 106: 11667-11672, 2009).

The present inventors have previously found that TUG1, which is one of lncRNA, is highly expressed in glioma stem cells (GSCs) established from a human GBM in comparison with that in normal tissues and the suppression of TUG1 expression contributes to the suppression of GSC proliferation, and have further found that nucleic acid medicaments targeting TUG1 are effective in treating the GBM. Furthermore, based on such findings, the present inventors have found that TUG1 is highly expressed also in some tumors that had been not reported so far and that the antitumor effect of the nucleic acid medicaments could also be expected on such TUG1 highly expressing tumors as in GSCs (Japanese Patent Application No. 2015-024713 (filing date: Feb. 10, 2015), WO2016/129633A1)).

As described in Background Art above, there are very few reports on the relationship between TUG1 and tumors and moreover, also on the treatment of tumors, it has not been sufficiently proved whether the suppression of TUG1 expression is effective in treatment of particular tumors having high expression although the expression of TUG1 varies depending on the kind of tumor.

TUG1 is induced by p53 and has a role to suppress particular genes involved in the cell cycle and the possibility that lncRNAs including TUG1 function in a tumor proliferation-suppressing way in the p53 transcription pathway has also been pointed out hypothetically, but in fact that is not well known (A. M. Khalil et al., PNAS, 106: 11667-11672, 2009).

Under such circumstances, the present inventors have found that the proliferation of tumors such as brain tumor is suppressed by the suppression of TUG1 expression. The present inventors have now further found that the drug delivery formulation comprising a nucleic acid that suppresses high expression of a TUG1 gene is very effective in treating a subject having a tumor expressing the TUG1 gene at statistically significantly (P<0.01) higher levels than normal tissues (hereinafter referred to as "high expression"), such as brain tumor, pancreatic cancer, breast cancer, colorectal cancer, prostate cancer, liver cancer, lung cancer, leukemia, and lymphoma, or in preventing the subject from tumor metastasis. Here, the prevention of tumor metastasis is considered to involve the suppression of tumor metastasis caused by cancer stem cells since the TUG1 gene is expressed in cancer stem cells and the tumor proliferation is suppressed when the gene expression is suppressed.

Since cancer stem cells often have resistance to anticancer agents, they are known to remain even after the cancer cells are reduced apparently and cause metastasis and recurrence. Accordingly, the ability to develop agents targeting cancer stem cells is considered to enable the suppression of metastasis and the prevention of recurrence. Since the TUG1 gene is also expressed in cancer stem cells, the drug delivery formulation according to the present invention enables effective attacks to cancers or tumors expressing the TUG1 gene.

The drug delivery formulation according to the present invention comprises a nucleic acid that suppresses high expression of a TUG1 gene and is capable of delivering the nucleic acid specifically to cancer or tumor cells. Among the cancers and tumors exemplified above, brain tumor and pancreatic cancer in particular are known to be most difficult to treat and the formulation can produce effective anticancer effect on such cancers or tumors.

The present invention will be described more specifically below.

1. Nucleic Acids that Suppress High Expression of TUG1 Gene

The active ingredients of the compositions according to the present invention are nucleic acids that suppress high expression of the TUG1 gene in tumors.

With regard to the term "suppress high expression of the TUG1 gene" herein, the term "high expression" refers to an abnormal state where the level (or an amount) of TUG1 is higher than that expressed normally in normal tissues (or normal cells) and the term is used in the meaning of suppressing the high expression of the TUG1 gene to a normal level or a level lower than the normal level and suppressing functions of lncRNA that is a transcript of the TUG1 gene. Here, the functions of lncRNA refer, in the present invention, to functions related to the proliferation, progression, or metastasis of cancers or tumors. According to the present invention, it is possible to suppress the expression of TUG1 in a subject having a tumor highly expressing TUG1, such as brain tumor, pancreatic cancer, breast cancer, colorectal cancer, prostate cancer, liver cancer, lung cancer, leukemia, and lymphoma and to thereby suppress the proliferation of the tumor.

The subject is not limited, as long as it is an animal, but preferably a mammal, for example, a human, a dog, a cat, a horse, a cow, or another mammal, for example, a mammal maintained in a zoo and a preferred animal is a human. Among such animals, subjects having tumors in which the gene of TUG1 is highly expressed are subject animals of the present invention.

The TUG1 is a TUG1 in the above-mentioned animal, for example, a TUG1 which is a natural variant consisting of: the nucleotide sequence of NR_110492 (SEQ ID NO: 1), NR_110493 (SEQ ID NO: 2), or NR_002323 (SEQ ID NO: 3) known as a transcript (lncRNA) of the human TUG1 gene; or a nucleotide sequence comprising a deletion(s), substitution(s), addition(s), or insertion(s) of one or several nucleotides in any of the nucleotide sequences; or a nucleotide sequence having 70% or more, 80% or more, or 90% or more, preferably 95% or more, further preferably 98% or more or 99% or more sequence identity with any of the above-mentioned nucleotide sequences.

The term "several" used herein refers to an integer between 2 and 10 and preferably an integer between 2 and 5. Moreover, the sequence identity may be determined using a known algorithm for obtaining sequence alignments such as nucleotide sequences, for example, BLAST.

The nucleic acids that suppress high expression of the TUG1 gene in the present invention include, for example, an siRNA or a precursor RNA thereof or a modified RNA thereof having the RNA interference (RNAi) effect, or a vector comprising a DNA encoding an siRNA for a transcript RNA of the TUG1 gene or a precursor RNA of the siRNA. Other examples of the nucleic acids are an antisense RNA or an antisense DNA or a modified nucleic acid thereof or a vector comprising a DNA encoding the antisense RNA or antisense DNA.

The nucleic acids in the present invention are not limited to particular sequences of nucleic acids, as long as they suppress high expression of the TUG1 gene and suppress the proliferation of a tumor(s), but it is preferred that they target a region(s) in the nucleotide sequence of a transcript RNA of the TUG1 gene in the above-mentioned subject, for example, a region at the nucleotide positions 1044 to 1062, 1044 to 1062, or 1044 to 1062 (region #1 in FIG. 2) and/or a region at the nucleotide positions 2997 to 5181, 2941 to 5111, or 2941 to 5125 (a region including #5 to #4 in FIG. 2) in the nucleotide sequence of SEQ ID NO: 1, 2, or 3, respectively, which is the nucleotide sequence of a transcript RNA of the human TUG1 gene, for example.

With regard to the siRNA having the RNAi effect to TUG1 or a precursor RNA thereof, the siRNA is a double stranded RNA consisting of a sense RNA and an antisense RNA, consisting of 18 to 25 nucleotides, preferably 20 to 24 nucleotides, and more preferably 21 to 23 nucleotides complementary to a part of a transcript RNA of the TUG1 gene and having the RNAi effect. Each of the 3' ends of the sense RNA and the antisense RNA may have an overhang of 2 to 5 nucleotides, preferably 2 nucleotides. The possibility that overhang interacts with RISC has been pointed out (W. R. Strapps et al., Nucleic Acids Res. 2010 August, 38 (14): 4788-4797).

The RNAi effect has a meaning that is generally used in the field and is a phenomenon where a small double-stranded RNA (siRNA) degrades a target transcript RNA in a way specific to its nucleotide sequence and suppresses the gene expression.

The above-mentioned precursor RNA is a priRNA, preRNA, or shRNA of the siRNA. The priRNA has a transcript RNA sequence of the TUG1 gene, such as the nucleotide sequence of SEQ ID NO: 1, 2, or 3. The preRNA is a preshRNA produced by enzymatic processing of the priRNA. The shRNA is the abbreviation for short hairpin RNA and comprises a stem of sense and antisense strands that have the same sequences as the siRNA and a hairpin loop, and it is produced enzymatically from preshRNA. The hairpin structure of the shRNA is cut into siRNA by the cellular mechanism and binds with an RNA-induced silencing complex (RISC), which binds to a transcript RNA having a sequence complementary to the antisense strand of the siRNA and cuts the transcript RNA.

The nucleic acid according to the present invention is any one or a combination of two or more of siRNAs comprising sense strands consisting of the nucleotide sequences of SEQ ID NOs: 4 to 11 and antisense strands consisting of the nucleotide sequences of SEQ ID NOs: 12 to 19 complementary to the sense strands, respectively.

Alternatively, the nucleic acid according to the present invention is a vector comprising a DNA encoding the above-mentioned siRNA or precursor RNA thereof, or antisense RNA, or an antisense DNA, each of them being for a transcript RNA of the TUG1 gene. A preferred precursor RNA is shRNA.

The vector is a viral vector, such as adeno associated virus, retrovirus, lentivirus, or Sendai virus, or a nonviral vector such as plasmid or artificial chromosome (for example, bacterial artificial chromosome (BAC), yeast artificial chromosome (YAC), human artificial chromosome (HAC), or murine artificial chromosome (MAC)), comprising a regulatory sequence that allows the expression of the above-mentioned DNA when it is introduced in cells. The preferred vector is a plasmid, Sendai virus vector, an adeno associated virus vector from the view point of safety. The plasmid is preferably a plasmid that is available in mammalian cells, preferably human cells, and is proved to be safe. Examples of the plasmid vector include, but are not limited to, for example, the vectors described in JP Patent Publication (Kohyo) No. 2014-508515A, for example, non-viral vectors such as pSilencer 4.1-CMV (Ambion), pcDNA3, pcDNA3.1/hyg, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL, pKSV-10, pBPV-1, pML2d, and pTDT1.

The regulatory sequence can comprise a promoter, a transcription initiation site, a terminator, or the like and may comprise an enhancer, a selection marker sequence, or the like, where needed. The usable promoter may be any endogenous or exogenous promoter, as long as it promotes the transcription initiation of the above-mentioned DNA in particular host cells, and examples thereof include the U6 or H1 promoter, which allows constitutive expression from the vector after its introduction into cells and also allows inheritance of the vector to daughter cells and inheritance of the effect of gene silencing.

In general, RNA is considerably unstable in the body, for example, because it is easy to be degraded by ribonucleases in the blood. To solve the problem, preferably a sense strand and an antisense strand are subjected to nucleotide modification in the present invention. The modification may include a modification of at least one nucleotide, preferably a plurality of nucleotides, for example, a base modification, a sugar modification, a modification of phosphodiester moieties, or a combination thereof, and/or a ring structure (i.e., a structure consisting of a double stranded stem and two loops), a chimeric structure containing DNA, and the like. Non-limiting examples of the modification include the following.

Both RNA and DNA are nucleic acids composed of a chain of nucleotides comprising sugars, bases, and phosphodiester linkages. A structural difference between the nucleic acids is that of the sugars in nucleotides. Specifically, the sugar in RNA is ribose, while the sugar in DNA is 2'-deoxyribose, in which the hydroxyl group at the position 2' is replaced with hydrogen. A further difference is that of the bases. Specifically, the bases of RNA are constituted by adenine (A), uracil (U), guanine (G), and cytosine (C), while the bases of DNA are constituted by adenine (A), thymine (T), guanine (G), and cytosine (C).

Examples of the modification of the phosphodiester moieties, which form the backbone, include the substitution of phosphorothioate, phosphorodithioate, alkylphosphonate or phosphoramidate linkages, for phosphodiester linkages.

Examples of the modification of the bases and the sugars include 2'-deoxy-2'-halo (for example, fluoro, chloro, or bromo) nucleotide, 2'-deoxy-2'-halo (where the halo is, for example, fluoro, chloro, or bromo) pyrimidine nucleotide, 2'-deoxy-2'-halo (where the halo is, for example, fluoro, chloro, or bromo) cytidine nucleotide, 2'-deoxy-2'-halo (where the halo is, for example, fluoro, chloro, or bromo) uridine nucleotide, 2'-deoxy-2'-halo (where the halo is, for example, fluoro, chloro, or bromo) guanosine nucleotide, 2'-O-methyl purine nucleotide, 2'-deoxyribonucleotide, locked nucleic acid (LNA; for example, 2'-O, 4'-C methylene bridge (—O—CH$_2$—) modified nucleotide, 2'-O, 4'-C ethylene bridge (—O—CH$_2$CH$_2$—) modified nucleotide, and the like), 2'-methoxyethyl nucleotide, 4'-thionucleotide, 2'-methoxyethoxy (2'-MOE) nucleotide, 2'-methoxy(2'-OMe) nucleotide, 2'-deoxy-2'-chloronucleotide, 2'-azide nucleotide, and the like, as illustrated in JP Patent Publication (Kohyo) No. 2007-525192. Moreover, as for 2'-modified nucleotide, in addition to the above-mentioned examples, the position 2' of the sugar may be substituted with, for example, halogen, allyl, amino, azide, acetoxy, alkyl, alkoxy, carboxy, acyl, carbonyloxy, benzyl, phenyl, nitro, thiol, thioalkoxy, aryl, alkenyl, alkynyl, cyano, OCN, CF$_3$, OCF$_3$, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkylaryl, aralkyl, O-alkylaryl, O-aralkyl, O(CH$_2$)$_2$SCH$_3$, O—(CH$_2$)$_2$—O—N(R$_m$)(R$_n$), or O—CH$_2$—C(=O)—N(R$_m$)(R$_n$), as described in, for example, JP Patent Publication (Kohyo) No. 2010-507579, where R$_m$ and R$_n$ are independently H, an amino-protecting group, or a substituted or unsubstituted C$_1$-C$_{10}$ alkyl.

The position of the modification in the nucleotide sequence of a nucleic acid according to the present invention is not particularly limited, as long as the tumor proliferation is suppressed, and it is, for example, 1 to 4 nucleotides at the 5' end and/or 1 to 4 nucleotides at the 3' end of the sequence. Furthermore, when the nucleic acid is a double stranded RNA such as siRNA, the tumor proliferation effect can be obtained by the modification of the antisense strand only.

The LNA modified nucleotides are artificial nucleic acids developed by Takeshi Imanishi et al. (M. Abdur Rahman, Sayori Seki, Satoshi Obika, Haruhisa Yoshikawa, Kazuyuki Miyashita, Takeshi Imanishi: "Design, synthesis and properties of 2',4'-BNA: A bridged nucleic acid analogue" J. Am. Chem. Soc. 130. 4886-4896 (2008); Satoshi Obika et al., Tetrahedron Lett., 38 (50): 8735-8738 (1997); JP Patent No. 4755972 (Sautaris Pharma)) and nucleotides modified from the nucleotide sequences of nucleic acids such as siRNAs, antisense RNAs, and antisense DNAs according to the present invention by introducing LNA (also referred to as "BNA (Bridged Nucleic Acid)") into sugar moieties thereof have markedly increased resistance to nucleases. Such nucleic acids contain at least 2, preferably 3 to 4, LNA modified nucleotides in each end side. Some examples of the LNA modified antisense RNAs and LNA modified antisense DNAs are modified RNAs having the antisense strand nucleotide sequences (SEQ ID NOs: 28 to 35) of FIG. 3A and, for example, LNA modified RNAs consisting of any of the nucleotide sequences such as SEQ ID NOs: 36 to 38, and SEQ ID NO: 51 to 53, and LNA modified DNAs consisting of the nucleotide sequence of SEQ ID NO: 56, but not limited thereto.

The nucleic acids according to the present invention may also have an RNA/DNA chimeric structure containing a deoxyribonucleotide sequence in a part of the nucleotide sequence of an siRNA. By including a deoxyribonucleotide sequence(s), such nucleic acids can become more nuclease-resistant as compared with those having only a ribonucleotide sequence (for example, JP Patent No. 3803318). The deoxyribonucleotide may be contained in the percentage of 30% or less, preferably 20% or less, relative to the total number of nucleotides in the antisense strand or the sense strand of the nucleotide sequence of an siRNA. The deoxyribonucleotides may also be contained in both of the antisense strand and the sense strand of the siRNA or may be contained in only the sense strand. Moreover, the deoxyribonucleotides in the nucleotide sequence of a siRNA are preferably located on the 3' side and for example, 2 to 4 deoxyribonucleotides may be present, in a consecutive sequence, as an overhang at the 3' end. Specifically, the RNA/DNA chimeras are double stranded RNAs in which the nucleotide sequences of the sense strands are the nucleotide sequences of SEQ ID NOs: 20 to 27 and the nucleotide sequences of the antisense strands are the nucleotide sequences of SEQ ID NOs: 28 to 35, respectively.

Nucleic acids having the above-mentioned ring structure (that is, a structure consisting of a double stranded stem and two loops) are a so-called dumbbell type of single stranded RNAs. The stem is constituted by a sense strand sequence and an antisense strand sequence of the siRNA that are sequences complementary to each other. The loops are constituted, for example, by approximately 2 to approximately 15 non-complementary nucleotides per loop connected to respective ends of the stem (for example, U.S. Pat. Nos. 5,168,053; 5,190,931; 5,135,917; Smith and Clusel et al. (1993) Nucl. Acids Res. 21: 3405-3411; and U.S. Pat. No. 5,087,617).

Other examples of the nucleic acids include the above-mentioned antisense RNAs or antisense DNAs, or modified nucleic acids thereof.

The antisense RNAs or antisense DNAs are single stranded nucleic acids that target the lncRNA which is a transcription product of the TUG1 gene. While the siRNA targeting the lncRNA degrades the lncRNA, the antisense RNAs or antisense DNAs suppress or inhibit the function of the lncRNA. In order to increase in vivo stability, the antisense RNAs or antisense DNAs are preferably modified derivatives comprising an RNA/DNA chimeric structure and/or one or more of the above-mentioned modified nucleotides. Examples of the modified nucleotides are those described above and more preferable examples are a combination of phosphorothioate modification and 2'-MOE nucleotides, 2'-OMe nucleotides, or LNA modified nucleotides. The nucleotide length of the antisense RNAs or antisense DNAs or modified derivatives thereof are usually 12 to 100 nucleotides, preferably 15 to 50 nucleotides, more preferably 20 to 30 nucleotides. The nucleotide length may be a length longer than 100 nucleotides, but it might be disadvantageous particularly in terms of the production costs and therefore the above-mentioned range is suitable. The sequences of the antisense RNAs or antisense DNAs may be nucleotide sequences or modified nucleotide sequences, which are complementary to consecutive nucleotide sequences of the above-mentioned size selected from: transcript lncRNAs of the TUG1 gene; or nucleotide sequences of DNAs encoding the transcript lncRNAs, for example, a nucleotide sequence of SEQ ID NO: 1, 2, or 3 from human TUG1 or a nucleotide sequence of a natural variant of TUG1 consisting of a nucleotide sequence having 70% or more, 80% or more, or 90% or more, preferably 95% or more, further preferably 98% or more or 99% or more sequence identity with any of the aforementioned nucleotide sequences. With regard to the target, the antisense RNAs or antisense DNAs preferably target, for example, the region at nucleotide positions 1044 to 1062, 1044 to 1062, or 1044 to 1062 (the region #1 in FIG. 2) and/or the region at nucleotide positions 2997 to 5181, 2941 to 5111, or 2941 to 5125 (the region including #5 to #4 in FIG. 2) in the nucleotide sequence of SEQ ID NO: 1, 2, or 3, respectively, which is the nucleotide sequence of a transcript RNA of the human TUG1 gene, as described above. Specifically, some examples of the antisense RNAs comprising at least 2, preferably 3 to 4, LNA modified nucleotides on each end side are antisense RNAs having the antisense strand nucleotide sequences (SEQ ID NOs: 28 to 35) of FIG. 3A, for example, those having any of the nucleotide sequences of SEQ ID NOs: 36 to 38 and 51 to 53, but not limited thereto. Furthermore, the antisense DNAs in these specific examples are those having nucleotide sequences modified from the above-mentioned antisense RNA sequences by substituting uracil (U) with thymine (T).

2. Drug Delivery Formulation for Treating or Preventing Tumor

The formulation of the present invention is characterized in that it comprises a nucleic acid that suppresses high expression of a TUG1 gene and thereby suppresses the proliferation of tumors. The formulation of the present invention has micelles or a micelle-like structure (referred to as "polymeric micelle(s)") formed from a block copolymer. The block copolymer and the formulations will be explained below.

<Block Copolymer>

The block copolymer that is one of the components of the formulations according to the present invention may be prepared by the methods described, for example, in WO2013/162041, WO2012/096399, or the like. The block copolymer and methods for production thereof will be described below.

The block copolymer that forms the polymeric micelle comprises a cationic poly(amino acid) segment(s) and a hydrophilic polymer chain segment(s). The cationic poly (amino acid) segment may preferably comprise a hydrophobic amino acid segment and/or a hydrophobic side group to increase hydrophobicity. Moreover, the cationic poly(amino acid) segment and the hydrophilic polymer chain segment may be bound via a linking group. The micelle has a multimolecular micellar structure (hereinafter, referred to as "micelle-type polyion complex (PIC)"), in which the hydrophilic polymer chain segment is oriented on the outer shell side, while the cationic poly(amino acid) segment is oriented on the inner shell side, or the micelle has a unimolecular micelle-like structure (hereinafter referred to as "unit-type PIC") in which the hydrophilic polymer chain segment encapsulates or covers the cationic poly(amino acid) segment. More specifically, the micelle may have a particles-like structure to incorporate a nucleic acid in the micelle or may have a structure in which a nucleic acid is electrostatically bound to the cationic poly(amino acid) segment to form a complex and the hydrophilic polymer chain segment encapsulates or covers the poly(amino acid) segment. In either case, preferably the micelle has a nanoparticle-size micelle or micelle-like structure.

In the polymeric micelle, a nucleic acid is preferably electrostatically attracted by the cationic poly(amino acid) segment and the nucleic acid is incorporated in or attached into the micelle and the micelle has a so-called EPR (Enhanced Permeability and Retention) effect, which enables the micelle to penetrate the neovascular wall and to accumulate in tumors.

In new blood vessels (or neovascularization) in tumors, pericytes are weakly bound to endothelial cells, smooth muscle cells are very few or lost, and basement membranes are thin or almost missing. Therefore, new blood vessels in tumors are known to have a vascular structure in which even substances with sizes larger than the size that allows passage in the new blood vessels of tumors easily leak out of the neo blood vessel walls and easily penetrate the neo blood vessel walls. The range of molecular weights of substances that can penetrate the blood vascular walls in tumors, such as the above-mentioned block copolymers that form the polymeric micelles, is preferably approximately 10 kDa to approximately 100 kDa and more preferably approximately 15 kDa to approximately 50 kDa, or the maximum (diameter) size of the substances is preferably approximately 10 nm to approximately 100 nm and more preferably approximately 20 nm to approximately 50 nm (S. Azzi et al. Front Oncol. 2013, 3:211. doi: 10.3389/fonc. 2013. 00211; F. Alexis et al., Mol Pharmaceutics 2008, 5 (4): 505-515). Such a size allows the substances to accumulate in the tumor. Moreover, in order to increase the accumulation in the tumor, as described below, the RGD (arginine-glycine-aspartic acid) or NGR (asparagine-glycine-arginine) peptide, which specifically binds to endothelial cells of new blood vessels in tumors, can be bound to the above-mentioned block copolymers (R. J. Boohaler et al., Curr Med Chem 2012, 19 (22): 3794-3804).

As used herein, the term "electrostatically attract" refers to binding or attachment of a nucleic acid molecule to a polymer molecule by the attraction between the positive charge of a cationic poly(amino acid) segment and the negative charge of phosphate ions of the nucleic acid by the electrostatic force.

The cationic poly(amino acid) segment has positive charges that counterbalance the negative charges of the nucleic acid to electrically neutralize the micelles overall or partially and, while the hydrophilic polymer chain segment has a chain length that enables the hydrophilic polymer chain segment to incorporate or encapsulate (or cover) the nucleic acid.

The hydrophilic polymer chain segment and the cationic poly(amino acid) segment are components of the block copolymer molecule, and the structural characteristics and arrangement of the segments will further be described below.

The hydrophilic polymer chain segment may be arranged, for example, at the end (one end or both ends) of the cationic poly(amino acid) segment. In addition, the hydrophilic polymer chain segment may be grafted to side chains of intermediate portions (preferably, substantially central portions) of the cationic poly(amino acid) segment or may be arranged between two adjacent cationic poly(amino acid) segments, instead of or in addition to the end. When the hydrophilic polymer chain segment is arranged between two adjacent cationic poly(amino acid) segments, the hydrophilic polymer chain segment may be arranged so as to extend in the direction that crosses the arrangement direction of these cationic poly(amino acid) segments.

The block copolymer has one or more hydrophilic polymer chain segments. When the block copolymer has a plurality of hydrophilic polymer chain segments per molecule of the block copolymer, the hydrophilic polymer chain segments may consist of one or more branched polymer chains. Since the block copolymer that is a component of the formulation according to the present invention can incorporate or cover a nucleic acid, the metabolism or degradation by enzymes or the like can be preferably avoided. As a result, micellar particles excellent in blood retainability are obtained. The number of the hydrophilic polymer chain segments in a block copolymer may be, for example, 1 to 4 and preferably 1 to 2.

The hydrophilic polymer chain segment may be composed of any appropriate hydrophilic polymer. Examples of the hydrophilic polymer include poly(ethylene glycol), polysaccharide, poly(vinyl pyrrolidone), poly(vinyl alcohol), poly(acrylamide), poly(acrylic acid), poly(methacrylamide), poly(methacrylic acid), poly(methacrylic acid ester), poly (acrylic acid ester), poly(amino acid), poly (malic acid), poly(oxazoline), or derivatives thereof. Examples of the polysaccharide include starch, dextran, fructan, and galactan. The poly(ethylene glycol) may be, for example, poly (ethylene glycol) that has been end-modified with a group such as C1-C6 alkyl group. Furthermore, poly(ethylene glycol) substances having, at the end, for example various functional groups for binding with a cationic poly(amino acid) segment or a linking group (also referred to as "linker") are commercially available and poly(ethylene glycol)s with various molecular weights or of branched type are also commercially available. Such poly(ethylene glycol) substances are easily obtainable and are thus preferably used.

The hydrophilic polymer chain segment may have a weight average molecular weight of preferably 10000 to 80000 and more preferably 10000 to 60000, for example 10000 to 40000 per segment.

In the case of block copolymers for the preparation of unit-type PIC, the length of the hydrophilic polymer chain segment is set at an appropriate length depending on the chain length of the nucleic acid contained in the polymeric micelles and, specifically, the hydrophilic polymer chain segment is set so as to have a length that can encapsulate or cover the nucleic acid. When at least one hydrophilic polymer chain segment in the polymeric micelle has a radius of gyration (Rg) equal to or longer than the length of the nucleic acid contained in the polymeric micelles (Note: where a plurality of nucleic acids are contained, the length of the nucleic acid is the total length of the nucleic acids.), it is determined that the entirety of the nucleic acid is encapsulated in or covered with the hydrophilic polymer chain segment. For example, since the radius of gyration (Rg) of the poly(ethylene glycol) with a weight average molecular weight of 21,000 or 42,000 is approximately 6.5 nm or approximately 9.7 nm, respectively, it is determined that these can singly cover siRNA (length, approximately 5.7 nm). Moreover, with regard to the polymeric micelle that comprises: a hydrophilic polymer chain segment arranged so as to have a rotation center (for example, a site linking to a poly(amino acid) segment) on one end side of a nucleic acid; and a hydrophilic polymer chain segment arranged so as to have a rotation center on the other end side of the nucleic acid, when the total of the radii of gyration (Rg) of the hydrophilic polymer chain segments at the both ends of the nucleic acid is equal to or longer than the length of the nucleic acid contained in the polymeric micelle particles, then it is determined that the entirety of the nucleic acid is encapsulated in or covered with the hydrophilic polymer chain segment. In such a polymeric micelle, each hydrophilic polymer chain segment preferably has a radius of gyration (Rg) equal to or longer than half of the length of the nucleic acid, more preferably a radius of gyration (Rg) equal to or longer than the length of the nucleic acid, far more preferably equal to or longer than 1.2 times of the length of the nucleic acid, and most preferably equal to or longer than 1.3 times of the length of the nucleic acid. The upper limit of the length of the hydrophilic polymer chain segment is hard to be affected by the steric hindrance or the like and is not limited as long as it is advantageous to the formation of the polymeric micelle, but it may be set at, for example, such a length that the radius of gyration (Rg) thereof is, for example, equal to or shorter than 2.5 times, preferably equal to or shorter than 1.6 times, of the length of the nucleic acid contained in the polymeric micelle particles.

In the block copolymers that can be used in the formulation according to the present invention, a cyclic peptide comprising the arginine-glycine-aspartic acid (RGD) sequence (referred to as "cRGD"), for example, a cyclic peptide consisting of the arginine-glycine-aspartic acid-phenylalanine-lysine sequence (WO2012/096399) can be bound to the end of the hydrophilic polymer chain segment. cRGD can serve as a ligand to adhere or bind the micelle to cancer cells. Similarly, the NGR peptide may also be used as the ligand as described below.

In the block copolymers, the cationic poly(amino acid) segment and the hydrophilic polymer chain segment may be linked to each other via any appropriate linking group. Examples of the linking group include an ester bond, an amide bond, an imino group, a carbon-carbon bond, an ether bond, or the like. Moreover, these segments may be linked via a linking group (for example, a disulfide bond, a hydrazone bond, a maleamate bond, or an acetal group) that can be cleaved in the living body. In addition, the cationic poly(amino acid)-side end and/or the hydrophilic polymer chain-side end of the block copolymer may be modified in any appropriate way, unless the effect of the present invention is adversely affected.

The amino acids that constitute the cationic poly(amino acid) segment may be any appropriate cationic amino acids having a cationic group (for example, an amino group, a guanidyl group, an imidazoyl group, or the like) in the side chain. Examples thereof include basic amino acids such as lysine, arginine, histidine, ornithine, and the like. Alternatively, in order to increase the hydrophobicity of the cationic poly(amino acid) segment, hydrophobic amino acids (for example, leucine, isoleucine, valine, phenylalanine, proline, and the like) and cationic amino acids may be contained.

the following formula (1) or (2). In the formula (1) or (2), examples in which the number of poly(ethylene glycol) chains that are hydrophilic polymer chain segments is 2 are illustrated, but the number of poly(ethylene glycol) chains may also be 1.

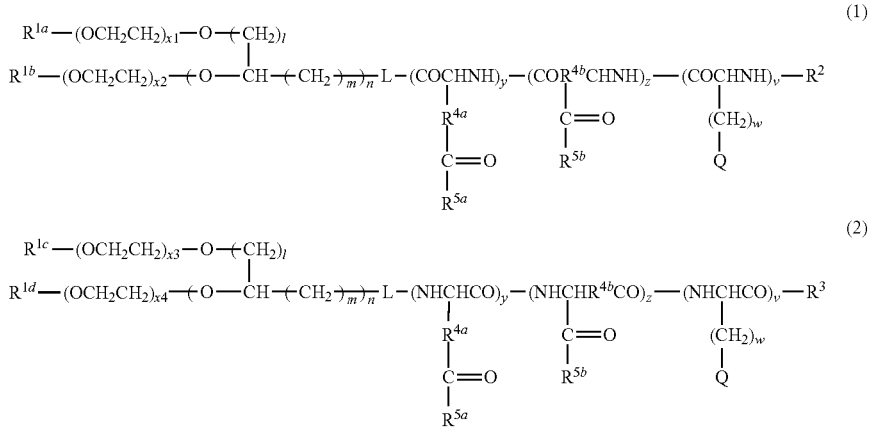

The cationic poly(amino acid) segment comprises, for example, polylysine.

In the case of block copolymers for the preparation of unit-type PIC, amino acids having one cationic group in the side chain, more specifically, amino acids that has one positive charge in the side chain at blood pH, may preferably be used in terms of preferable formation of electrostatic bond with each phosphate group in a nucleic acid, since the negative charges of the nucleic acid are from phosphate groups and the nucleic acid has one negative electric charge (electric charge=−1) at substantially equal intervals.

In the cationic poly(amino acid) segment, the distance from the main chain to the cationic group in the side chain is preferably short. Specifically, it is preferred that the cationic group is bound to the main chain via preferably 1 to 6 atoms, more preferably 1 to 4 atoms.

In the case of block copolymers for the preparation of micelle-type PIC, the cationic poly(amino acid) segment may preferably have an approximately equal amount, an approximately ½ amount, an approximately ¼ amount, or an approximately ⅛ amount of positive charges to the negative charges of the nucleic acid contained in the polymeric micelle. Because the cationic poly(amino acid) segments have such amounts of electric charges, different polymeric micelles that vary in terms of the number of block copolymers contained (for example, 1, 2, 4, or 8) can be obtained. In addition, the number of amino acid residues contained in the cationic poly(amino acid) segment may be set appropriately according to the amount of electric charges that the segment is desired to have. The cationic poly(amino acid) segment may contain non-cationic amino acid residues in a range that does not harm the effect of the present invention. The number of non-cationic amino acid residues may be, for example, equal to or less than 20%, preferably equal to or less than 10%, more preferably equal to or less than 5%, and far more preferably equal to or less than 2% of the total number of amino acid residues contained in the cationic poly(amino acid) segment.

Examples of the block copolymer for the preparation of the unit-type PIC may be represented, without limiting, by In each formula, $R^{1a}$ to $R^{1d}$ are independently a hydrogen atom or an unsubstituted or substituted linear or branched alkyl group having 1 to 12 carbon atoms, $R^2$ is a hydrogen atom, an unsubstituted or substituted linear or branched alkyl group having 1 to 12 carbon atoms, or an unsubstituted or substituted linear or branched alkyl-carbonyl group having 1 to 24 carbon atoms, $R^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms, $R^{4a}$ and $R^{4b}$ independently represent a methylene group or an ethylene group, $R^{5a}$ and $R^{5b}$ are independently selected from the same or different groups of the group consisting of the following groups:

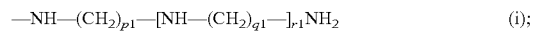

$$-NH-(CH_2)_{p1}-[NH-(CH_2)_{q1}-]_{r1}NH_2 \qquad (i);$$

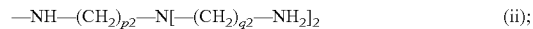

$$-NH-(CH_2)_{p2}-N[-(CH_2)_{q2}-NH_2]_2 \qquad (ii);$$

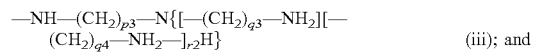

$$-NH-(CH_2)_{p3}-N\{[-(CH_2)_{q3}-NH_2][-(CH_2)_{q4}-NH_2-]_{r2}H\} \qquad (iii); \text{ and}$$

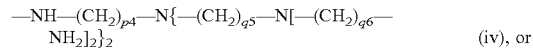

$$-NH-(CH_2)_{p4}-N\{-(CH_2)_{q5}-N[-(CH_2)_{q6}-NH_2]_2\}_2 \qquad (iv), \text{ or}$$

$R^{5a}$ and $R^{5b}$ are independently a hydrogen atom, a phenyl group, a benzyl group, a $-(CH_2)_4$-phenyl group, an unsubstituted or amino group- or carbonyl group-substituted C4-C16 alkyl group, or a residue of a sterol derivative, bonded to $-O-$ or $NH-$, wherein p1 to p4, q1 to q6, r1 and r2 are independently an integer of 1 to 5, Q is $-NH_2$ or $-NHC(=NH)NH_2$, L is a divalent linking group or a valence bond, x1 to x4 are independently, for example, an integer of 110 to 2,000, y, z, and v are independently, for example, an integer of 0 to 60, provided that the relationship of $5 \leq y+z+v \leq 60$ is satisfied, w is, for example, an integer of 1 to 6, l and m are independently, for example, an integer of 0 to 5, and n is, for example, 0 or 1.

In the formula (1) or (2), L is a divalent linking group or a valence bond. Any appropriate linking group can be adopted as the divalent linking group. For example, in the formula (1), L can be -$L^1$-$L^2$-$L^3$-, and in the formula (2), L can be -$L^4$-$L^5$-$L^6$-. In this context, $L^1$ and $L^4$ are independently —(O—$(CH_2)_a)_b$-$L^{1a}$-, wherein a is, for example, an integer of 1 to 5, b is, for example, an integer of 0 to 300, when b is 2 or larger, all the moieties a do not have to be the same, and $L^{1a}$ is a valence bond, —S—S—, —NH—, —O—, —O—$CH(CH_3)$—O—, —OCO—, —OCONH—, —NHCO—, —NHCOO—, —NHCONH—, —CONH— or —COO—; $L^2$ and $L^5$ are independently a valence bond or -$L^{2a}$-$L^{2b}$-$L^{2c}$-, wherein each of $L^{2a}$ and $L^{2c}$ is a structure serving as a spacer and is, but is not particularly limited to, for example, a substituted or unsubstituted alkyl group having 1 to 12 carbon atoms, and $L^{2b}$ is, for example, a structure represented by any of the following formulas (3) to (5); $L^3$ is —$((CH_2)_c$—O$)_d$—$(CH_2)_e$-$L^{3a}$-, wherein c is, for example, an integer of 1 to 5, d is, for example, an integer of 0 to 500, e is, for example, an integer of 0 to 5, when d is 2 or larger, all the moieties c do not have to be the same, and $L^{1a}$ is —NH— or —O—; and $L^6$ is —$((CH_2)_f$—O$)_g$—$(CH_2)_h$-$L^{6a}$-$(CH_2)_i$—CO—, wherein f is, for example, an integer of 1 to 5, g is, for example, an integer of 0 to 300, h is, for example, an integer of 0 to 5, i is, for example, an integer of 0 to 5, when g is 2 or larger, all the moieties f do not have to be the same, and $L^h$a is —OCO—, —NHCO—, —OCONH—, —NHCOO—, —NHCONH—, —CONH—, or —COO—.

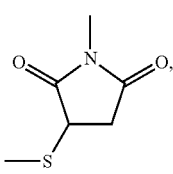

(3)

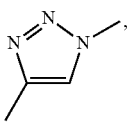

(4)

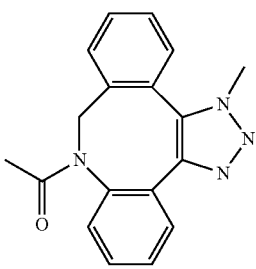

(5)

Examples of the alkyl moiety of the linear or branched alkyloxy group, alkyl-substituted imino group, or alkyl group having 1 to 12 carbon atoms, defined in the group represented by $R^{1a}$ to $R^{1d}$, $R^2$, or $R^3$ can include a methyl group, an ethyl group, a n-propyl group, an isopropyl group, a n-butyl group, a sec-butyl group, a tert-butyl group, a n-hexyl group, a decyl group, and an undecyl group. Examples of the alkenyl or alkynyl moiety of the linear or branched alkenyloxy group having 2 to 12 carbon atoms or the linear or branched alkynyloxy group having 2 to 12 carbon atoms can include those containing a double bond or a triple bond in the above-exemplified alkyl groups having 2 or more carbon atoms.

The substituent where such a group or moiety is "substituted" includes, but is not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkylsiloxy group, a siloxy group, or a silylamino group, or an acetalized formyl group, a formyl group, or a halogen atom such as chlorine or fluorine.

The groups represented by $R^{5a}$ and $R^{5b}$ will be defined. The groups selected from the group consisting of:

—NH—$(CH_2)_{p1}$—[NH—$(CH_2)_{q1}$—]$_{r1}NH_2$     (i);

—NH—$(CH_2)_{p2}$—N[—$(CH_2)_{q2}$—$NH_2$]$_2$     (ii);

—NH—$(CH_2)_{p3}$—N{[—$(CH_2)_{q3}$—$NH_2$][— $(CH_2)_{q4}$—$NH_2$—]$_{r2}$H}     (iii); and —NH—$(CH_2)_{p4}$—N{—$(CH_2)_{q5}$—N[—$(CH_2)_{q6}$— $NH_2$]$_2$}$_2$     (iv), or are preferably the same groups, more preferably groups of the formula (i). p1 to p4 and q1 to q6 are independently, for example, preferably 2 or 3, more preferably 2. On the other hand, r1 and r2 are independently, for example, preferably an integer of 1 to 3. The group represented by $R^{5a}$ or $R^{5b}$ may be selected as the same groups as to all the repeat units to which $R^{5a}$ or $R^{5b}$ belongs, or may be selected as different groups as to the respective repeat units.

Q may be selected as the same groups as to all the repeat units to which Q belongs, or may be selected as different groups as to the respective repeat units. w is, for example, 1, 2, 3, or 4.

x1 to x4 each representing the number of repeats of ethylene glycol are values that can be appropriately set according to the length of the nucleic acid contained in the desired polymeric micelle. In the case of forming, for example, polymeric micelle particles containing one double-stranded RNA of 21 base pairs, the lower limits of x1 to x4 are independently, but are not limited to, for example, 100 to 250, and the upper limits of x1 to x4 are independently, but are not limited to, for example, 900 to 1200.

Each of y, z and v is a value that can be appropriately set according to the amount of negative charge of the nucleic acid contained in the desired polymeric micelle, and the number of block copolymers contained therein. In the case of forming, for example, a block copolymer for unit-type PIC preparation containing one double-stranded RNA of 21 base pairs and two block copolymers, y, z, and v can be set such that the number of cationic groups in the cationic poly(amino acid) segment is, but is not limited to, an integer of preferably 18 to 22, more preferably 19 to 21, far more preferably 19 to 20. Thus, the drug delivery formulation of the present invention may comprise two block copolymers and may be in a state where the cationic poly(amino acid) segment in each block copolymer contains, for example, 18 to 22 cationic amino acid residues.

For the block copolymer for unit-type PIC preparation, n is, for example, 0 or 1, preferably 1. A block copolymer having two poly(ethylene glycol) chains can give polymeric micelles significantly excellent in blood retainability.

In the formula (1) or (2), the order of bonding of respective units constituting the cationic poly(amino acid) segment is arbitrary, and the formed structure may be a random structure or a block structure.

Block copolymers for micelle-type PIC preparation will be described below as the example (formulas (6) and (7)).

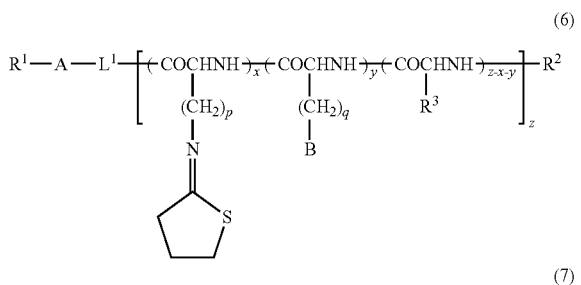

(6)

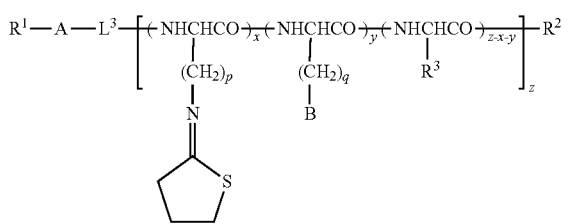

(7)

In each of the formulas, $R^1$ and $R^2$ are independently a hydrogen atom or, for example, an optionally substituted linear or branched alkyl group having 1 to 12 carbon atoms, A is a hydrophilic polymer chain, each of $L^1$ and $L^3$ is a linking group, B is a cation-containing group, $R^3$ represents the side chain of any amino acid, z represents, for example, an integer of 5 to 500, x represents, for example, an integer of 40% or more of z, y represents an integer and is 0 or 1 or more, z-x-y represents an integer and is 0 or 1 or more, provided that x and y are set such that the total of x, y, and z-x-y is z, p represents, for example, an integer of 1 to 10, and q represents, for example, an integer of 1 to 10, but x, y, z, p and q are not limited to the ranges described above.

The number of repeats of a hydrophilic polymer in the hydrophilic polymer chain can be, but is not limited to, preferably an integer of 30 to 2,000, more preferably an integer of 40 to 1,500, further preferably an integer of 50 to 1,000.

As is evident from the descriptions above, z represents the number of repeats of a poly(amino acid) segment. z is, but is not limited to, for example, an integer in the range of 5 to 500. The lower limit of this range may be, but is not limited to, for example, 10 to 20, and the upper limit of this range may be, but is not limited to, for example, 100 to 200.

B represents a cation-containing group of the amino acid segment having the cation-containing group. The cation-containing group is any appropriate group that contains a cation or is capable of forming a cation. Examples thereof include an amino group and a group containing an ammonium cation. By containing the amino acid segment having the cation-containing group, the block copolymer is capable of forming a complex (PIC) with the nucleic acid used as a drug under physiological conditions. Specific examples thereof include an amidine group and a diethylenetriamine-derived group selected from the group consisting of the following (i) to (iv):

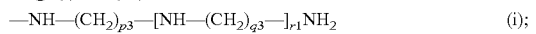   (i);

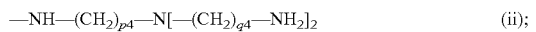   (ii);

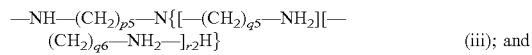   (iii); and

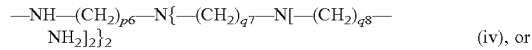   (iv), or

Preferably, the group represented by (i) can be used. p3 to p6 and q3 to q8 are independently, for example, preferably 2 or 3, more preferably 2. On the other hand, r1 and r2 are independently, for example, preferably an integer of 1 to 3.

The amino acid segment having the cation-containing group may have a thiol group (—SH group) at the terminus of the side chain, i.e., the terminus of the cation-containing group. Such thiol groups are capable of reacting with each other and thereby forming a crosslinking reaction through a disulfide bond.

Specifically, the block copolymer having a target binding site is represented by, for example, the following formula (8) or (9):

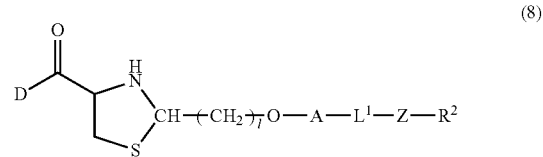

(8)

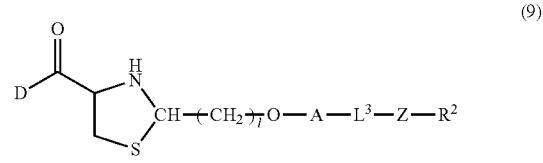

(9)

In the formulas, A, $R^2$, $L^1$, and $L^3$ are as defined in the formulas (6) and (7), Z represents the poly(amino acid) segment of the formula (6) or (7), l represents, but is not limited to, for example, an integer of 1 to 5, and D represents the target binding site.

The target binding site (D in the formulas (8) and (9)) of the block copolymers is, but is not limited to, preferably a peptide having a molecular weight of, for example, 200 to 20,000 Da, more preferably a peptide having a molecular weight of 300 to 10,000 Da, far more preferably a peptide having a molecular weight of 500 to 3,000 Da.

D is, but is not limited to, preferably a peptide having, for example, 2 to 200 amino acid residues, more preferably a peptide having 1 to 100 amino acid residues, further preferably a peptide having 3 to 30 amino acid residues.

Examples of the peptide include peptides that can specifically bind to integrins involved in angiogenesis, intimal thickening, or malignant tumor proliferation and specifically include the RGD peptide and the NGR peptide. In this context, the RGD peptide refers to a peptide comprising the arginine-glycine-aspartic acid (RGD) sequence, and the NGR peptide refers to a peptide comprising the asparagine-glycine-arginine (NGR) sequence. Because these peptides can bind to neovascular endothelial cells of tumors, the block copolymer according to the present invention can specifically accumulate in tumor cells. The RGD peptide is preferably a cyclic RGD (cRGD) peptide. An example of the cRGD peptide contained in the block copolymer represented by any of the formulas above is the peptide represented by the following formula (10):

(10)

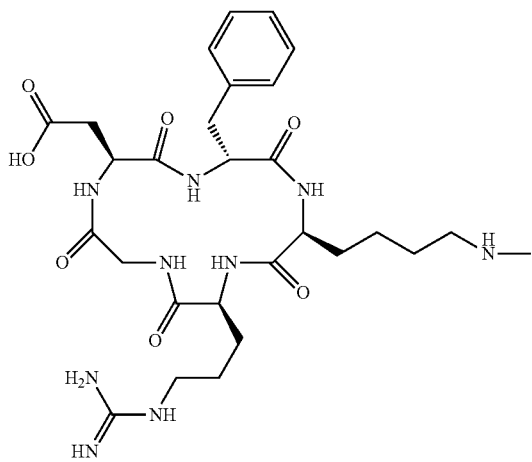

The NGR peptide is preferably a cyclic peptide and is, for example, a peptide containing a cyclized sequence containing K on the N-terminal side of the NGR sequence and E on the C-terminal side thereof, or containing C on both the N-terminal and C-terminal sides of the NGR sequence (A. H. Negussie et al., J Control Release 2010; 143 (2): 265-273; and T. R. Pearce et al., Adv. Mater 2012; 24: 3803-3822).

The block copolymer can be prepared by any appropriate method. For example, N-carboxylic anhydrides (NCA) of predetermined amino acids, if necessary, with a protective group introduced therein are sequentially polymerized by using the terminal amino group of a ω-terminally aminated hydrophilic polymer (for example, poly(ethylene glycol)) as an initiator. Subsequently, the resultant may be converted to a polycation segment by deprotection or side chain conversion. Alternatively, a poly(amino acid), if necessary, with a protective group introduced therein is first synthesized and subsequently bonded to a hydrophilic polymer. Then, a block copolymer having a polycation segment may be synthesized, if necessary, followed by deprotection or side chain conversion. Various methods can be used as a method for bonding the poly(amino acid) to the hydrophilic polymer. A typical method involves introducing reactive functional groups to their respective termini, followed by coupling. Examples thereof include a method of bonding a carboxyl group to an amino group using a condensing agent or by active esterification, a method based on maleimide and thiol, and a so-called click chemistry method based on alkyne and azide.

<Drug Delivery Formulation>

The drug delivery formulation of the present invention is an antitumor drug delivery formulation for treating a subject having a tumor more highly expressing TUG1 gene than normal tissues or for preventing the subject from metastasis of the tumor, wherein the formulation comprises, as the active ingredient, polymeric micelles having a nucleic acid suppressing the high expression of the TUG1 gene, the polymeric micelle particles comprising a block copolymer having a cationic poly(amino acid) segment and a hydrophilic polymer chain segment, and the nucleic acid, wherein the nucleic acid forms a complex by binding to cationic groups of the cationic poly(amino acid) segment, and/or the nucleic acid is incorporated in the micelles or is electrostatically bound (or attached) within the micelles, and the polymeric micelles accumulate in a tumor.

The drug delivery formulation of the present invention can be obtained, for example, by admixing the block copolymer and the nucleic acid at an N/P ratio of more than 1, if necessary, in a buffered aqueous solution. A block copolymer for micelle-type PIC preparation can be obtained by admixing the block copolymer and the nucleic acid such that the N/P ratio of 1 or more is, but is not limited to, for example, preferably 1.0 to 2.5, more preferably 1.1 to 2.0, further preferably 1.2 to 1.6. When the N/P ratio is thus set, free nucleic acids or block copolymers can be decreased, and the formulation comprising the block copolymer and the nucleic acid at high contents can be obtained. When the N/P ratio of a block copolymer for unit-type PIC preparation is more than 1, for example, the formulation containing a given amount of block copolymers that are not electrostatically bound to the nucleic acid (free block copolymers) can have a high level of balance between the effect of recapturing free nucleic acids by free block copolymers and the smooth release of the nucleic acid from the formulation delivered to target tumor cells. Therefore, the improvement in blood retainability of the nucleic acid and the antitumor effect can be achieved more significantly. In this context, the N/P ratio means [the total number of cationic groups in the block copolymer (N)]/[the total number of phosphate groups in the nucleic acid (P)].

In another embodiment, the unit-type PIC which is the formulation of the present invention can also be obtained by admixing the block copolymer and the nucleic acid at a N/P ratio of, for example, more than 2.5, preferably 3 or more, 4 or more, or 5 or more, more preferably 10 or more, if necessary, in a buffered aqueous solution. When the N/P ratio is thus increased, the stability in blood of the nucleic acid contained in the formulation can be drastically improved. The upper limit of the N/P ratio is, but is not limited to, for example, 20 to 50.

The buffered aqueous solution can be, for example, a HEPES buffer solution (pH 7.3 to 7.4) or a Tris buffer solution (pH 7.4).

Figure 16:
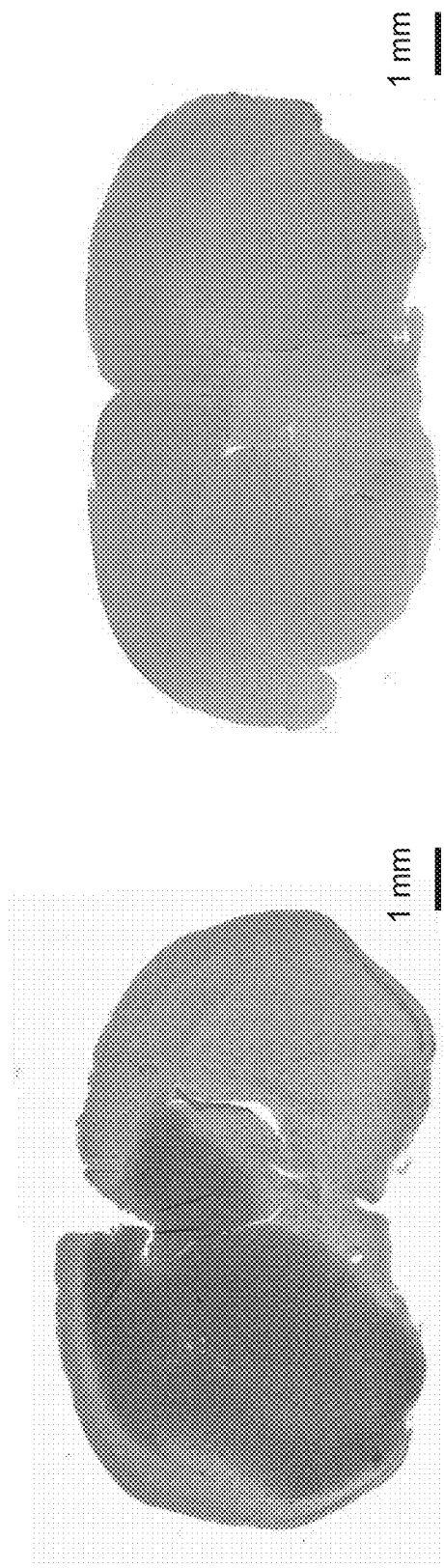
FIG. 16 illustrates the result of the hematoxylin eosin (HE) staining of the mouse brain tissues after the drug delivery formulation (25 µg/mouse) containing the TUG1-LNA oligomer (LNA-TUG1-2 #1 (SEQ ID NO: 51)) was administered intravenously to brain tumor orthotopic mouse models 10 times every 3 days. The left panel is the brain tissues of the mice to which the drug delivery formulation containing a siRNA (SEQ ID NOs: 54 and 55) for Luciferase gene (firefly GL3 luciferase) was transformed (as the control), while the right panel is the brain tissues of the mice to which the drug delivery formulation containing the TUG1-LNA oligomer was transformed (as the present invention).

The formulation of the present invention permeates new blood vessels in a tumor and accumulates in the tumor. This is demonstrated by the accumulation of a nucleic acid agent in glioma (brain tumor stem cells) of FIG. 16. For the micelle-type PIC, the particle size of the micelle is, but is not limited to, for example, preferably within the range of approximately 10 nm to approximately 100 nm. For the unit-type PIC, the particle size is, but is not limited to, for example, preferably within the range of approximately 10 nm to approximately 30 nm.

The formulation of the present invention is formed into a nano-sized particles-like structure as described above by mixing the block copolymer and the nucleic acid (as the pharmaceutical active ingredient) in the buffered aqueous solution.

The formulation of the present invention preferably has a property of accumulating specifically in tumor tissues by administration into blood and therefore has significantly low adverse reaction.

The dose of the nucleic acid for humans is, but is not limited to, for example, approximately 0.0001 mg to approximately 1,000 mg in terms of a siRNA molecule or an antisense nucleic acid molecule per dose and per kg body weight of an adult. In general, the dose or administration amount should be selected in consideration of the sex, age, body weight, symptoms, and severity of the subject, adverse reaction, etc. The administration can be performed, for example, at 1-week, 2-week, 3-week, or 4-week intervals, or at intervals exceeding 1 month, if necessary.

The formulation may be prepared in the form of a pharmaceutical composition by mixing the nucleic acid, as an active ingredient, with a carrier or a diluent and an additive. If necessary, the pharmaceutical composition may be combined with another anticancer agent (for example, a chemotherapeutic, an antibody drug, and an immune checkpoint inhibitor) and/or another treatment-related agent.

The dosage form is preferably a parenteral dosage form such as an injection or drops.

The carrier or the diluent is an aqueous solvent, for example, distilled water, sterilized water, a Ringer's solution, physiological saline, or a buffer solution.

The additive is, for example, a pharmaceutically acceptable expander, dispersant, buffer, preservative, solubilizer, stabilizer, tonicity agent, or pH adjuster.

The administration route is, for example, intravenous administration, intraarterial administration, or intracerebral administration, as described above.

It is supposed that the drug delivery formulation of the present invention is transferred into a tumor tissue where the active ingredient nucleic acid liberated from the aggregate is then taken up into the cytoplasm via endocytosis together with the block copolymer.

The present invention further provides a method for treating a subject having a tumor more highly expressing TUG1 gene, such as brain tumor, pancreatic cancer, breast cancer, colorectal cancer, prostate cancer, liver cancer, lung cancer, leukemia (particularly, myeloid leukemia) or lymphoma, as compared with normal tissues, comprising administering the formulation as an anticancer agent to the subject.

As demonstrated by Examples below, the use of the nucleic acid in, for example, brain tumor has been confirmed to have an excellent cell proliferation-suppressive effect. Therefore, the formulation of the present invention is also excellent as an anticancer agent targeting a tumor stem cell.

The composition, the subject, the dose, the administration route, the number of doses, etc. are as described above.

The formulation of the present invention can be administered to the subject in combination with the administration of another anticancer therapeutic agent, such as a chemotherapeutic, an antibody drug, or an immune checkpoint inhibitor. The administration of the formulation can be performed before, concurrently with, or after the administration of a chemotherapeutic or an antibody drug for cancer treatment. In addition, the formulation of the present invention may contain a chemotherapeutic and/or an antibody drug for cancer treatment, in addition to the nucleic acid.

Examples of the chemotherapeutic include, but are not limited to, anticancer agents as described in JP Patent Publication (Kohyo) No. 2014-508515 A (2014), for example, topoisomerase inhibitors (for example, etoposide, camptothecin, topotecan, teniposide, and mitoxantrone), DNA alkylating agents (for example, cisplatin, mechlorethamine, cyclophosphamide, ifosfamide, melphalan, chlorambucil, busulfan, thiotepa, carmustine, lomustine, carboplatin, dacarbazine, and procarbazine), DNA strand cleavage-inducing agents (for example, bleomycin, doxorubicin, daunorubicin, idarubicin, and mitomycin C), antimicrotubular agents (for example, vincristine and vinblastine), antimetabolites (for example, cytarabine, methotrexate, hydroxyurea, 5-fluorouracil, floxuridine, 6-thioguanine, 6-mercaptopurine, fludarabine, pentostatin, and chlorodeoxyadenosine), anthracycline, vinca alkaloid, epipodophyllotoxin, and temozolomide.

Examples of the antibody drug include, but are not limited to, commercially available antibodies and antibodies to be developed (clinically tested) or launched, having an anticancer effect, such as trastuzumab, bevacizumab, panitumumab, and ramucirumab.

The immune checkpoint inhibitor is an agent for preventing cancer cells from avoiding attack from immune cells, and thereby recovering the original attack capability of the immune cells against the cancer cells, and includes, for example, anti-PD-1 antibodies and anti-PD-L1 antibodies, and agents functionally equivalent thereto.

The dose of another anticancer therapeutic agent, such as a chemotherapeutic, an antibody drug, or an immune checkpoint inhibitor is selected in consideration of the sex, age, body weight, symptoms, and severity of the subject, adverse reaction, etc., or is a dose that falls within a range actually used in clinical settings.

<Method for Treatment or Prevention>

The present invention further provides a method for treating or preventing a tumor more highly expressing TUG1 gene than normal tissues, in a subject, comprising administering the drug delivery formulation to the subject having the tumor.

The drug delivery formulation, the dose, the administration method, the administration in combination with another anticancer therapeutic agent, the subject including a human, the tumor or cancer, etc. are as described above. The therapeutic effect is to achieve proliferation suppression or regression of the tumor or cancer and/or suppression of its metastasis in the subject. On the other hand, the prophylactic effect is to prevent metastasis of the tumor or cancer, i.e., recurrence of the tumor or cancer, in the subject that has undergone anticancer treatment such as surgical operation, chemotherapy, radiotherapy, or immunotherapy.

EXAMPLES

The present invention will be described in more detail with reference to the following Examples. However, it should be noted that the technical scope of the present invention is not limited to these Examples.

Example 1

<TUG1 Expression Level in Various Tumor Cell Lines>

TUG1 expression levels were measured for various tumor cell lines by using quantitative RT-PCR. The tumor cell lines used were a glioma stem cell line (GSC), glioma cell lines (T98, U251, SK-MG1, and A02), breast cancer cell lines (MCF7, MDA231, SK-BR3, and T47D), colorectal cancer cell lines (Lovo, Caco-2, RKO, SW48, SW480, and SW1083), prostate cancer cell lines (PC3, LNCap, and Vcap), liver cancer cell lines (HepG2, Huh7, and A549), lung cancer cell lines (H920 and PC9), a leukemia cell line (Jurkat), a Burkitt lymphoma cell line (Raji), and a lymphoma cell line (Pfeiffer).

The results were represented as relative TUG1 expression to GAPDH (glyceraldehyde 3-phosphate dehydrogenase) as internal standard, and are shown in FIG. 1. It can be understood that the TUG1 gene expression level is higher in most of the tumor cell lines than the TUG1 expression level in normal tissues (e.g., the TUG1 expression level in normal brain tissue is: TUG1/GAPDH=0.05394 (mean of three cases with normal brain tissues)).

Example 2

<Position of TUG1 Target Sequence for siRNA and Suppressive Effect of siRNA>

To design nucleic acids (siRNAs) to suppress TUG1 expression, candidates for target sequence regions were picked out from the entire nucleotide sequences of TUG1 lncRNA (NR_110492 (SEQ ID NO: 1), NR_110493 (SEQ ID NO: 2), and NR_002323 (SEQ ID NO: 3)) (A. M. Khalil et al., PNAS, 106: 11667-11672, 2009), siDirect version 2.0, and siRNAs for the regions (i.e., si-TUG1#1 to si-TUG1#14 (note: each of these sequences includes two deoxyribonucleotide sequences at the 3'-terminal)) were produced through outsourcing to Hokkaido System Science Co., Ltd. (Sapporo, Japan) (FIG. 3).

Figure 2:
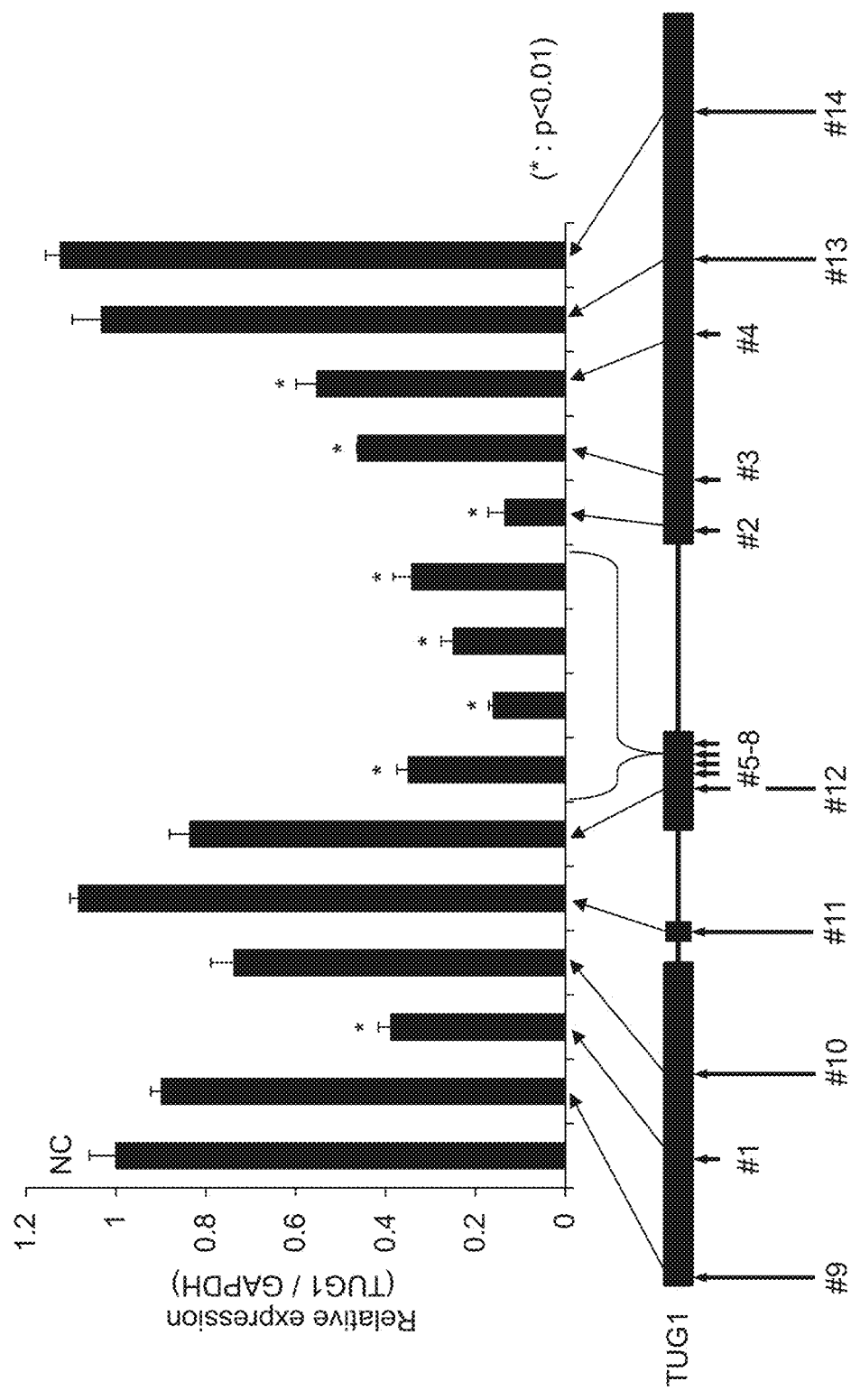
FIG. 2 illustrates positions of siRNA target sequences for TUG1 and the proliferation suppressing effect on the glioma stem cell line GSC. In the figure, si-TUG1 #1 to si-TUG1 #14 (nucleotide sequences, see FIG. 3) denote the prepared modified siRNAs (RNA/DNA chimera; "dCdA" and the like at the 3' end of the sense strand and the antisense strand are DNA sequences) and indicate the targeted positions in the TUG1 sequence. Moreover, the suppressive effect is represented by the relative expression of TUG1/GAPDH (internal standard)) to a control siRNA ("NC", Silencer Select Negative Control #1 siRNA (Life Technologies, cat. No. 4390843)). * indicates statistical significance (p<0.01).
Figure 4:
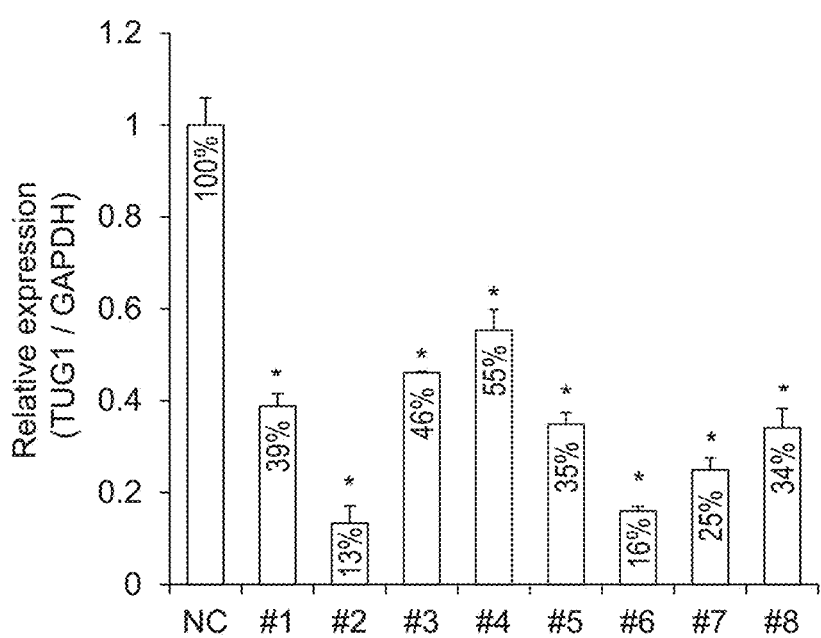
FIG. 4 illustrates the evaluation of TUG1 expression-suppressive effect of si-TUG1 #1 to si-TUG1 #8 (denoted as "#1" to "#8") on the glioma stem cell line GSC. The figure indicates relative expression levels of TUG1 (TUG1/GAPDH (internal standard)) to a control siRNA ("NC", Silencer Select Negative Control #1 siRNA (Life Technologies, cat. No. 4390843)) 3 days after the introduction of respective modified siRNAs. * indicates statistical significance (p<0.01).

Each of the siRNAs was introduced into the glioma stem cell line GSC ($1.0 \times 10^5$ cells) at a final concentration of 30 nM by using Lipofectamine 3000 (Life Technologies) in accordance with the attached protocol. Silencer Select Negative Control #1 siRNA (Life Technologies, catalog No. 4390843) was used as a control siRNA ("NC"). Three days after the siRNA introduction, the TUG1 expression level relative to that for the control siRNA was quantified by using quantitative RT-PCR (Applied Biosystems) with a GAPDH gene as an internal standard, and a significant TUG1 expression-suppressive effect was found for eight siRNAs (si-TUG1#1 to si-TUG1#8) (FIG. 2 and FIG. 4). For si-TUG1#9 to si-TUG1#14, on the other hand, a sufficient TUG1 expression-suppressive effect was not found.

In addition, it was found on the basis of these results that regions of nucleotide Nos. 1044 to 1062, 1044 to 1062, and 1044 to 1062 (the region of #1 in FIG. 2) in the respective nucleotide sequences of SEQ ID NOs: 1, 2, and 3, and/or regions of nucleotide Nos. 2997 to 5181, 2941 to 5111, and 2941 to 5125 (the region including #5 to #4 in FIG. 2) in the respective nucleotide sequences of SEQ ID NOs: 1, 2, and 3, are preferred as TUG1 target regions.

Example 3

<Suppression of GSC Tumor Proliferation>

Figure 5:
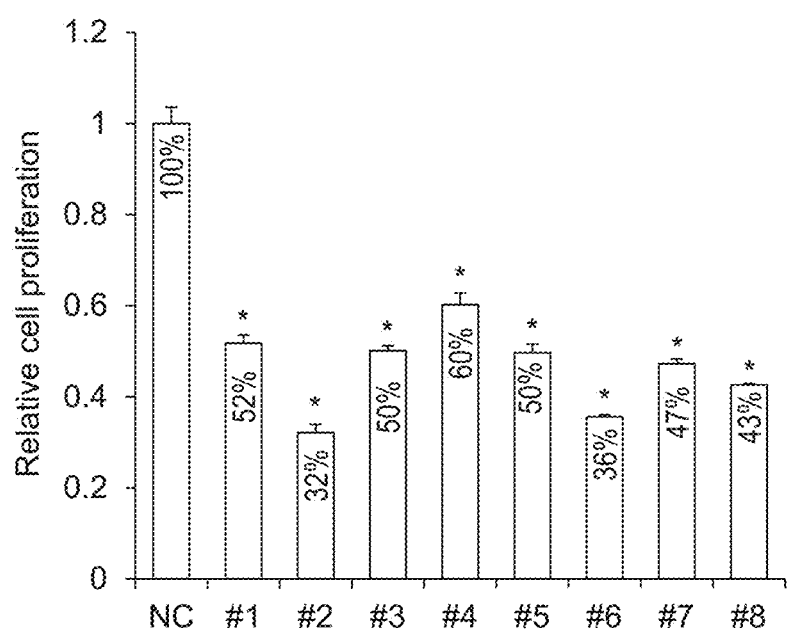
FIG. 5 illustrates the evaluation of anti-proliferation effect of si-TUG1 #1 to si-TUG1 #8 (denoted as "#1" to "#8") on the glioma stem cell line GSC. The figure indicates relative viable cell counts of GSC to a control siRNA ("NC") 3 days after the introduction of respective modified siRNAs. * indicates statistical significance (p<0.01).

Each of the eight siRNAs which had been prepared in Example 2 and found to have a TUG1 expression-suppressive effect (si-TUG1#1 to si-TUG1#8) was introduced into GSC tumor cells through lipofection as described in Example 2, and the viable cell counts were determined by the trypan blue staining (Life Technologies) 3 days after the introduction of each siRNA, and the anti-proliferation effect relative to that of the control siRNA ("NC") was analyzed. From the results, the significant anti-proliferation effect was found for each of the eight siRNAs used for the analysis (FIG. 5).

Example 4

<Suppression of GSC Tumor Proliferation with LNA-Modified Antisense RNA>

The antisense strand sequence (note: a sequence complementary to parts of the lncRNA sequence of TUG1) of si-TUG1#2, which suppressed TUG1 expression in the most effective manner in Example 2 and Example 3, was modified with LNA (Locked Nucleic Acid; 2'-O,4'-C methylene bridge (—O—CH$_2$—) nucleic acid nucleotide) to prepare three LNA-modified antisense RNAs (LNA-TUG1-1#1 (SEQ ID NO: 36), LNA-TUG1-1#2 (SEQ ID NO: 37), LNA-TUG1-1#3 (SEQ ID NO: 38); FIG. 6) through outsourcing to GeneDesign, Inc., and they were examined for TUG1 expression-suppressive effect. Each of the control siRNA ("NC"), si-TUG1#2, and the LNA-modified antisense RNAs was introduced into the glioma stem cell line GSC through lipofection, and RNA was collected 3 days, 7 days, and 10 days after the introduction to quantify the change of TUG1 expression levels over time.

Figure 7:
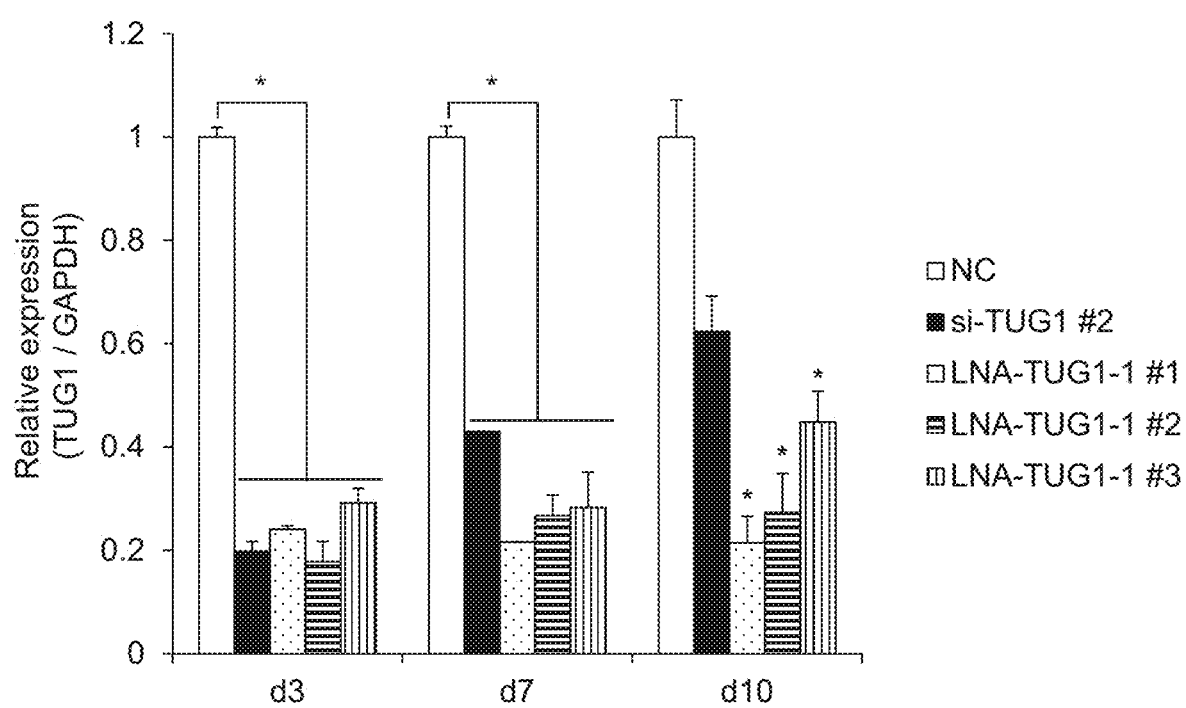
FIG. 7 illustrates the evaluation of TUG1 expression-suppressive effect of the 3 LNA modified antisense RNAs, i.e., LNA-TUG1-1 #1 (SEQ ID NO: 36), LNA-TUG1-1 #2 (SEQ ID NO: 37), and LNA-TUG1-1 #3 (SEQ ID NO: 38), and si-TUG1 #2 (sense: SEQ ID NO: 21, and antisense: SEQ ID NO: 29). For comparison, si-TUG1 #2 and a control siRNA ("NC") were used. Each of the siRNAs and LNA modified antisense RNAs was introduced into the glioma stem cell line GSC and relative TUG1 expression levels to a control siRNA ("NC") measured 3, 7, and 10 days later (d3, d7, d10) are shown in the figure. The expression levels are TUG1/GAPDH (internal standard). * indicates statistical significance (p<0.01).

The results revealed that the use of the LNA-modified antisense RNAs enabled retention of the TUG1 expression-suppressive effect for a longer period of time than in the case of si-TUG1#2 (FIG. 7).

Figure 8:
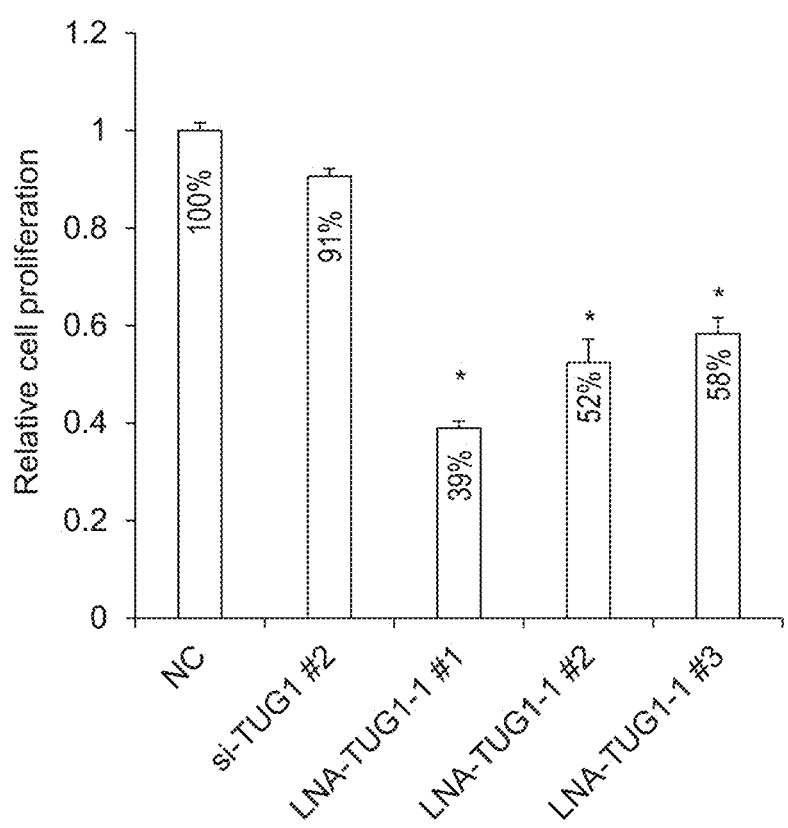
FIG. 8 illustrates the evaluation of antitumor cell proliferation-suppressive effect of each of the indicated siRNAs and LNA modified antisense RNAs (final concentration, 30 nM) on the glioma stem cell line GSC (initial cell counts, $1\times10^5$). The figure illustrates relative viable cell counts of GSC to a control siRNA ("NC") 10 days after the introduction into GSC of si-TUG1 (sense: SEQ ID NO: 21 and antisense: SEQ ID NO: 29) or each of the LNA modified antisense RNAs (LNA-TUG1-1 #1 (SEQ ID NO: 36), LNA-TUG1-1 (SEQ ID NO: 37), and LNA-TUG1-1 #3 (SEQ ID NO: 38)). * indicates statistical significance (p<0.01).

In addition, when the relative viable GSC cell counts were determined 10 days after introduction of each of the siRNAs and LNA-modified antisense RNAs, the significant anti-proliferation effect was found only for the LNA-modified antisense RNAs (FIG. 8).

Similarly, the antisense strand sequence (note: a sequence complementary to parts of the lncRNA sequence of TUG1) of si-TUG1#6 was modified with LNA to prepare three LNA-modified antisense RNAs (LNA-TUG1-2#1 (SEQ ID NO: 51), LNA-TUG1-2#2 (SEQ ID NO: 52), LNA-TUG1-2#3 (SEQ ID NO: 53); FIG. 9) through outsourcing to GeneDesign, Inc., and they were examined for TUG1 expression-suppressive effect. Each of the control siRNA ("NC"), si-TUG1#6, and the LNA-modified antisense RNAs was introduced into the glioma stem cell line GSC through lipofection, and RNA was collected 3 days, 7 days, and 10 days after the introduction to quantify the change of TUG1 expression levels over time.

Figure 10:
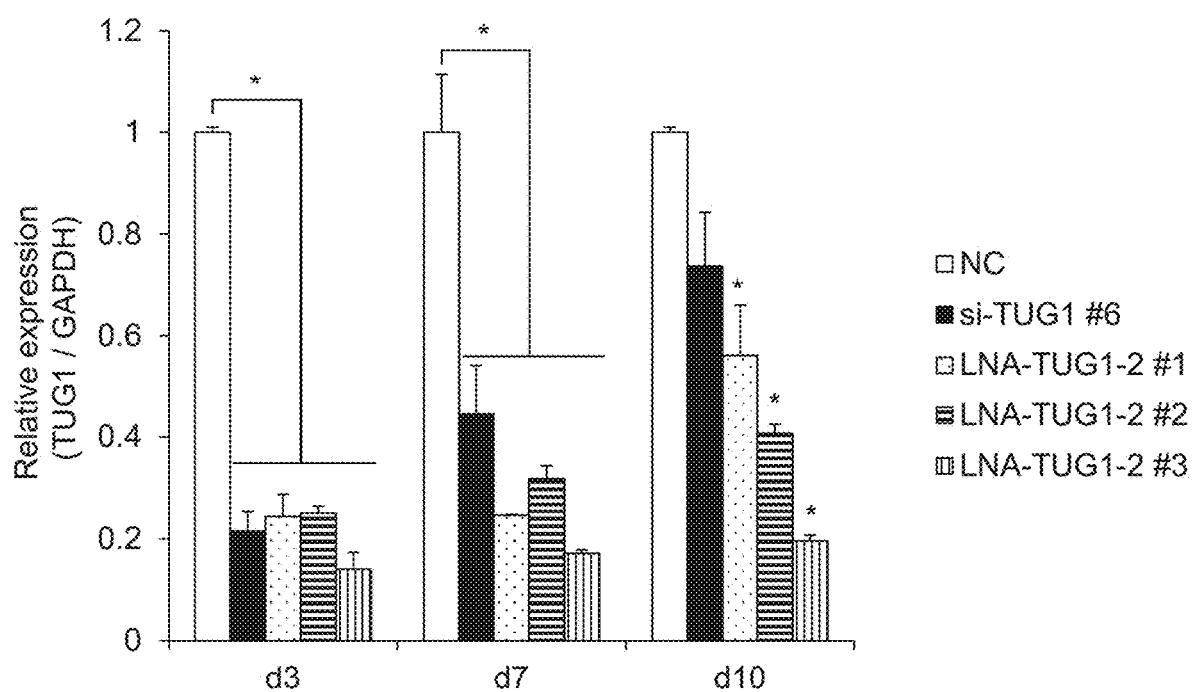
FIG. 10 illustrates the evaluation of TUG1 expression-suppressive effect of the 3 LNA modified antisense RNAs, i.e., LNA-TUG1-2 #1 (SEQ ID NO: 51), LNA-TUG1-2 #2 (SEQ ID NO: 52), and LNA-TUG1-2 #3 (SEQ ID NO: 53), and si-TUG1 #6 (sense: SEQ ID NO: 25 and antisense: SEQ ID NO: 33). For comparison, si-TUG1 #6 and a control siRNA ("NC") were used. Each of the siRNAs and LNA modified antisense RNAs was introduced into the glioma stem cell line GSC, and relative TUG1 expression levels to a control siRNA ("NC") measured 3, 7, and 10 days later (d3, d7, d10) are shown in the figure. The expression levels are TUG1/GAPDH (internal standard). * indicates statistical significance (p<0.01).

The results revealed that the use of the LNA-modified antisense RNAs enabled retention of the TUG1 expression-suppressive effect for a longer period of time than in the case of si-TUG1#6 (FIG. 10).

Figure 11:
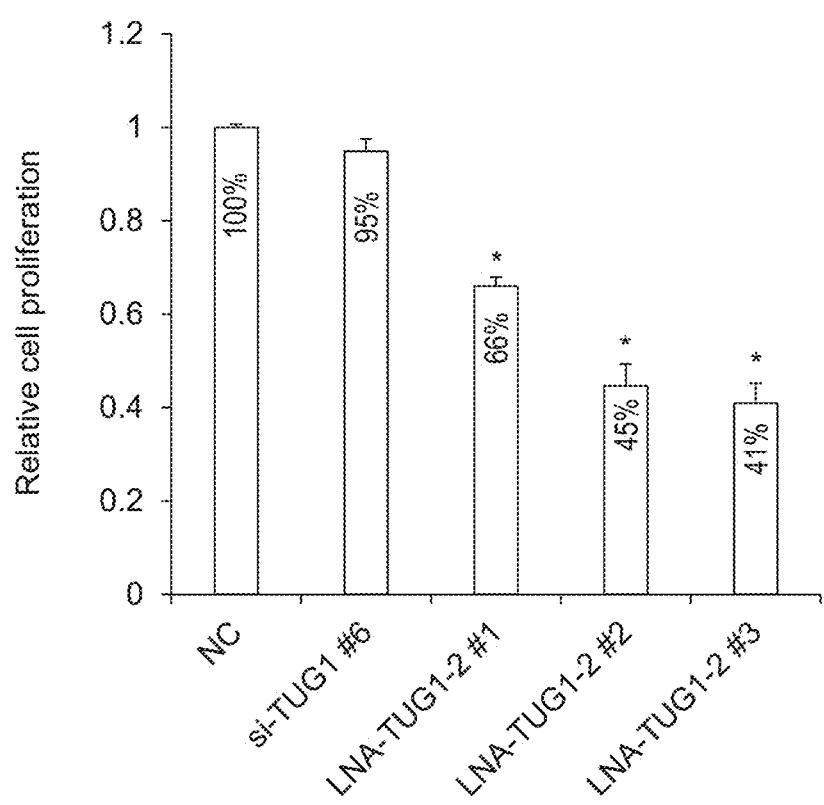
FIG. 11 illustrates the evaluation of antitumor cell proliferation-suppressive effect of each of the indicated siRNAs and respective LNA modified antisense RNAs (final concentration, 30 nM) on the glioma stem cell line GSC (initial cell counts, $1\times10^5$). The figure illustrates relative viable cell counts of GSC to a control siRNA ("NC") 10 days after the introduction into GSC of each of the si-TUG1 #6 (sense: SEQ ID NO: 25, and antisense: SEQ ID NO: 33) and LNA modified antisense RNAs (i.e., LNA-TUG1-2 #1 (SEQ ID NO: 51), LNA-TUG1-2 #2 (SEQ ID NO: 52), and LNA-TUG1-2 #3 (SEQ ID NO: 53)). * indicates statistical significance (p<0.01).

In addition, when the relative viable GSC cell counts were determined 10 days after introduction of each of the siRNAs and LNA-modified antisense RNAs, the more significant anti-proliferation effect was found for the LNA-modified antisense RNAs, and the superior anti-proliferation effect was found particularly for LNA-TUG1-2#2 (SEQ ID NO: 52) and LNA-TUG1-2#3 (SEQ ID NO: 53) (FIG. 11).

Example 5

<Suppression of Prostate Cancer Proliferation>

In accordance with the procedure as described in Example 2 and Example 3, si-TUG1#2 was introduced into the prostate cancer cell line PC3 through lipofection. The TUG1 expression level in the prostate cancer cell line PC3 and the relative cell proliferation rate of the PC3 line 3 days after the introduction were measured in the same manner as in the previous Examples. The control siRNA ("NC") was used as a negative control, and each expression level was similarly represented as the relative expression of TUG1 to GAPDH as internal standard.

Figure 12A:
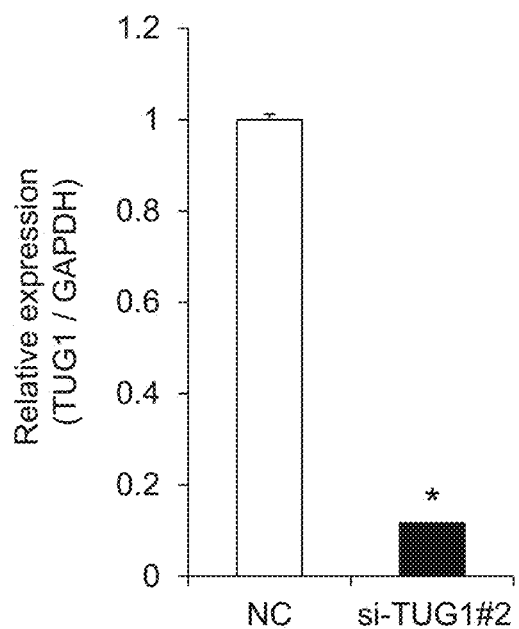
FIG. 12A illustrates the TUG1 expression level in the PC3 cell when si-TUG1 #2 or a control siRNA ("NC") was acted on the cell.
Figure 12B:
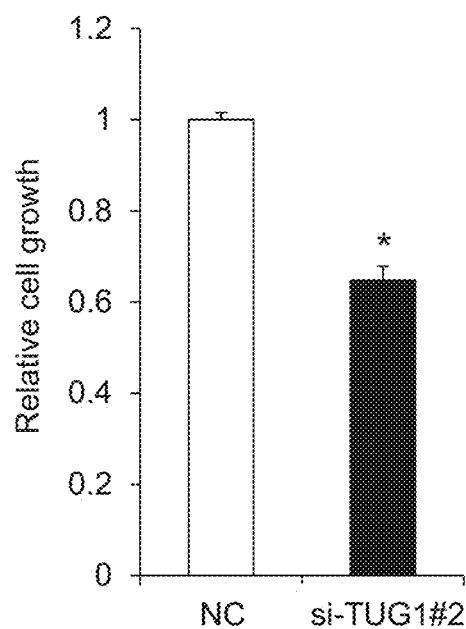
FIG. 12B illustrates the relative cell proliferation rate of the PC3 cell when the respective siRNAs were acted on the cell. * indicates statistical significance (p<0.01).

From the results, the proliferation-suppressive effect on the prostate cancer cell line PC3 due to inhibition of TUG1 was found (FIG. 12A and FIG. 12B).

Example 6

<Suppression of Tumor Proliferation in GSC Tumor-Bearing Mouse>

The glioma stem cell line GSC was subcutaneously transplanted to nude mice, and 5 μg of LNA-TUG1-1#1 (SEQ ID NO: 36) was directly administered to each tumor every 3 days after day 0, which is a day when the tumor size reached approximately 100 mm$^3$, and the tumor size was measured until day 35. As a control, the control siRNA ("NC") was administered to mice in the same manner.

Figure 13:
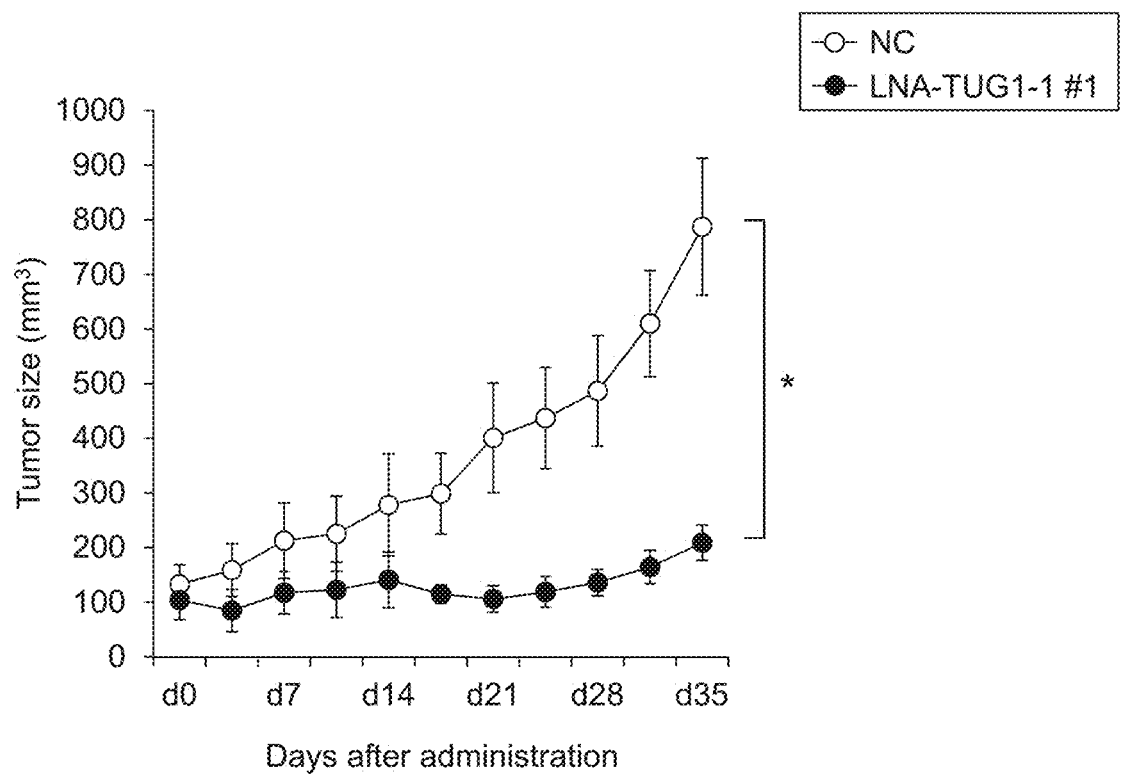
FIG. 13 illustrates the daily change of the tumor size when nude mice to which the glioma stem cell line GSC had been transplanted subcutaneously were treated by direct administration of LNA-TUG1-1 #1 ((SEQ ID NO: 36) or a control siRNA ("NC")) to the tumor of each mouse every three days. * indicates statistical significance (p<0.01).

From the results, the proliferation-suppressive effect on GSC due to use of LNA-TUG1-1#1 was found as demonstrated in FIG. 13.

Example 7

<In Vivo Suppression of Brain Tumor Proliferation with Unit-Type PIC Drug Delivery Formulation>

In this Example, drug delivery formulations containing TUG1-LNA oligomer were prepared and intravenously administered to brain tumor-orthotopically transplanted mice in order to analyze the specific accumulation of the TUG1-LNA oligomer in tumor tissues and the antitumor effect of the TUG1-LNA oligomer on an individual level.

(1) Preparation of Block Copolymer to Contain TUG1-LNA Oligomer

Two-armed α-methoxy poly(ethylene glycol)-block-poly (L-lysine) ((PEG)$_2$-PLys) was used as a block copolymer to contain the TUG1-LNA oligomer, and the block copolymer was prepared as follows in accordance with the method described in WO2013/162041.

Weighed were 2.00 g of a double-stranded poly(ethylene glycol) derivative (manufactured by NOF CORPORATION, product name: "SUNBRIGHT GL2-800PA", mean molecular weight=74,000 Da (37,000 Da×2)) purified with an ion exchange column (manufactured by GE Healthcare Japan Corp., product name: "CM-Sephadex C-50") and represented by the following formula (11):

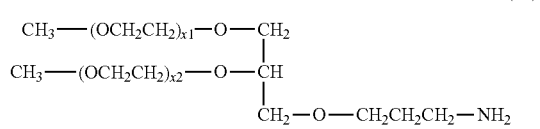

wherein x1 and x2 are each approximately 800 to 1,000, and 2.51 g of thiourea, and put in an eggplant flask. The eggplant flask was purged with argon, and 30 mL of N,N-dimethylformamide (DMF) was then added thereto. The mixture was heated to dissolve, and further stirred for 2 hours. Under argon atmosphere, 0.20 g (corresponding to 28 equivalents) of N-carboxylic anhydride of Nε-trifluoroacetyl-L-lysine (Lys(TFA)-NCA) was weighed in an eggplant flask, and dissolved in 3 mL of DMF. The resulting solution was added into the eggplant flask containing the double-stranded (PEG)$_2$ with a syringe. The mixture was reacted in a water bath at 25° C. under argon atmosphere with stirring for 2 days. After the disappearance of an absorption peak characteristic to NCA was confirmed by IR, 17 mL of methanol was added. The resulting solution was poured into 500 mL of cold diethyl ether with stirring, and reprecipitated. Further, a cycle consisting of removal of the supernatant, addition of 50 mL of methanol followed by heating for redissolution, and subsequent pouring of cold diethyl ether for reprecipitation was repeated twice. The precipitate was collected through filtration with a filter, and vacuum-dried to afford 1.95 g of (PEG)$_2$-PLys (TFA) in the form of white powder. In 100 mL of methanol, 1.00 g of the (PEG)$_2$-PLys (TFA) was dissolved. To the resulting solution, 10 mL of 1 N NaOH aqueous solution was added, and the mixture was reacted in a water bath at 35° C. with stirring for 17 hours. The reaction solution was transferred in a dialysis tube (MWCO=6,000 to 8,000), and dialysis was performed six times with 0.01 N hydrochloric acid as external solution, and then four times with pure water as external solution. The internal solution in the tube was freeze-dried to afford 0.85 g of (PEG)$_2$-PLys (hydrochloride) in the form of white powder.

The polymerization degree of PLys was determined as 20 by $^1$H-NMR on the basis of the molecular weight 74,000 of (PEG)$_2$. It was confirmed by GPC that a block copolymer: (PEG)$_2$-PLys having unimodal distribution and containing almost no homopolymer of Lys (polymerization degree, 21×2 for PEG, and 20 for PLys) was obtained.

The structure of (PEG)$_2$-PLys synthesized is as follows (formula (12)).

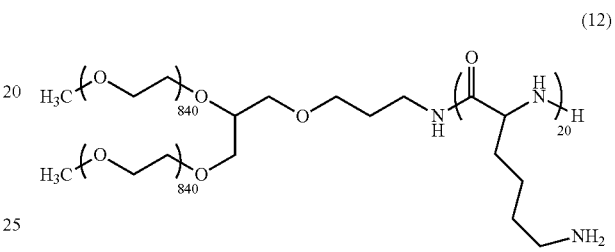

Various block copolymers differing in the type of PEG and/or the polymerization degree of polylysine can be obtained using the above-described method.

(2) Preparation of Unit-Type PIC Drug Delivery Formulation Containing TUG1-LNA Oligomer A drug delivery formulation having TUG1-LNA oligomer in the inner shell was prepared by gently stirring and mixing the (PEG)$_2$-PLys prepared in (1) above and the TUG1-LNA oligomer (LNA-TUG1-2#1 (SEQ ID NO: 51)) in 10 mM HEPES buffer solution (pH 7.3) at room temperature to give an N/P ratio of 20. In this time, the micelle-like structure (particle size, approximately 10 to 25 nm) was formed, in which the oligomer was electrostatically attracted by and attached to PLys of the block copolymer, and the hydrophilic PEG was arranged on the outer shell side.

(3) Suppression of Brain Tumor Proliferation with Unit-Type PIC Drug Delivery formulation Brain tumor stem cells (the cell line GSC-222) were orthotopically transplanted to the brain of immunodeficient mice (NOD/ShiJic-scid Jcl; CLEA Japan, Inc.), as brain tumor-orthotopically transplanted mouse model, to prepare mice with brain tumor engrafted, on day 30 after the transplantation.

Figure 14:
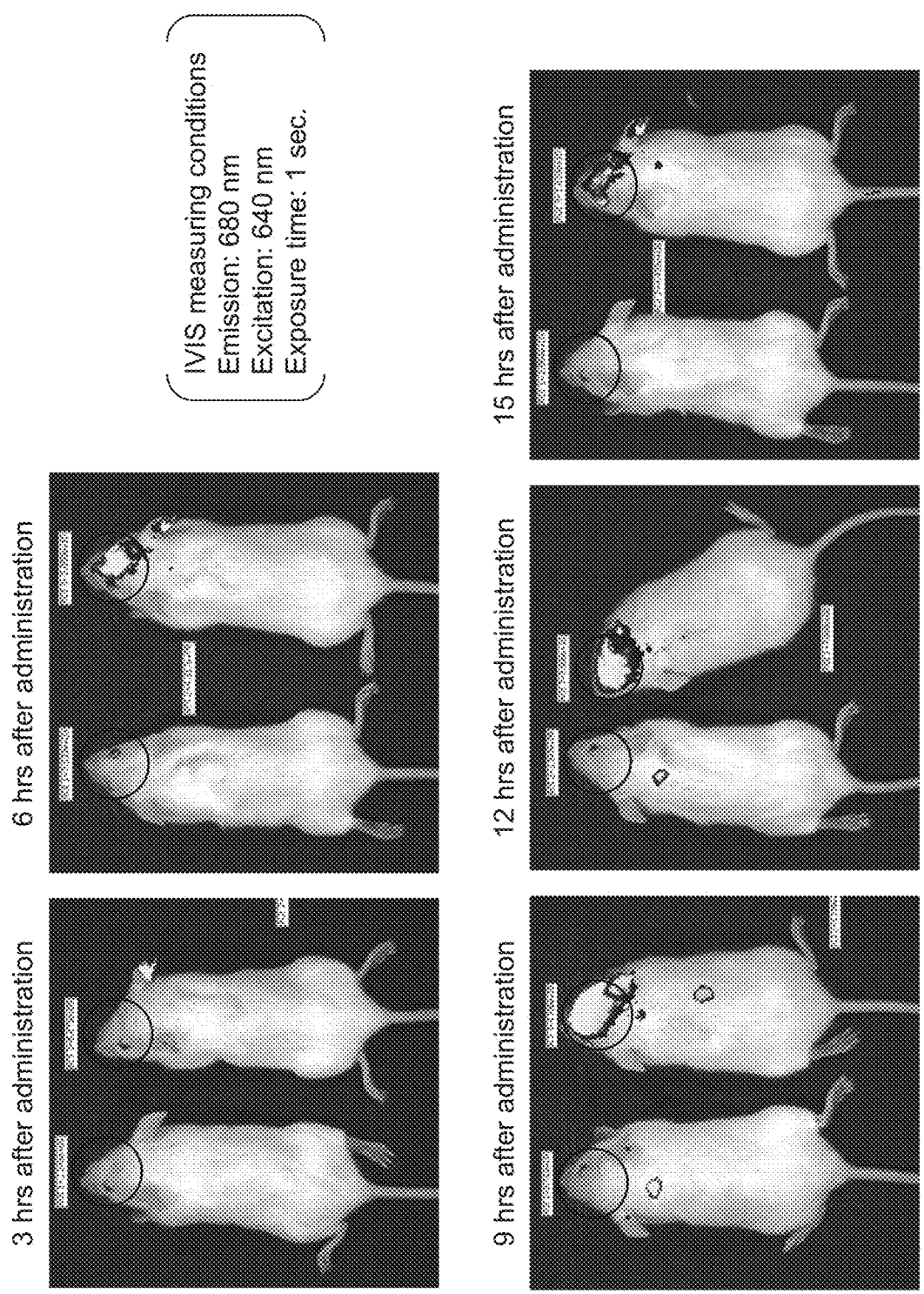
FIG. 14 illustrates that when the drug delivery formulation containing a TUG1-LNA oligomer (LNA-TUG1-2 #1 (SEQ ID NO: 51)) was administered intravenously to brain tumor orthotopic mouse models, the drug delivery formulation was specifically accumulated in the brain tumor tissue 3, 6, 9, 12, and 15 hours after the administration, as described in Example 7 below. In the panels of each time, the left panel illustrates the result in the mice to which the Alexa-647-labeled TUG1-LNA oligomer was singularly administered, and the right panel illustrates the result in the mice to which the drug delivery formulation containing the Alexa-647-labeled TUG1-LNA oligomer was administered.
Figure 15:
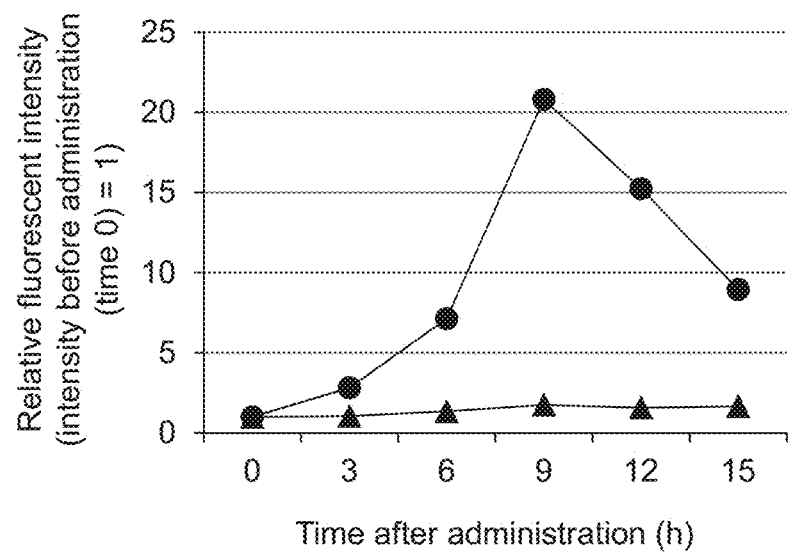
FIG. 15 is the graph illustrating change over time of fluorescence intensity of the drug delivery formulation targeted to brain tumor tissues based on the result of FIG. 14. The symbol "●" illustrates the change over time of relative fluorescence intensity in the brain tumor tissue of the mice to which the drug delivery formulation containing the Alexa-647-labeled TUG1-LNA oligomer was administered and the symbol "▲" illustrates the change over time of relative fluorescence intensity in the brain tumor tissues of the mice to which the Alexa-647-labeled TUG1-LNA oligomer was singularly administered. The relative fluorescence intensity is a value relative to the fluorescence intensity before the administration (0 hours), defined as 1.

To confirm accumulation of the TUG1-LNA oligomer in the brain on an individual mouse level, the TUG1-LNA oligomer to be contained in a drug delivery formulation was labeled with a fluorescent substance (Alexa-647). A single form of the TUG1-LNA oligomer labeled with Alexa-647 (which has not yet been in the form of polymeric micelles) was used for comparison analysis. The polymeric micelle containing the TUG1-LNA oligomer (i.e., the drug delivery formulation) and the single form of the TUG1-LNA oligomer were each intravenously administered to each of the brain tumor-orthotopically transplanted mice (25 µg/mouse), and the fluorescence intensity was measured with an IVIS Imaging System (Caliper LifeSciences). The results confirmed that the drug delivery formulation containing the TUG1-LNA oligomer was specifically accumulated in a brain tumor portion (FIG. 14, FIG. 15). FIG. 15 shows that the drug delivery formulation accumulated in the brain in 9 hours after administration provided increase of the fluorescence intensity to a maximum fluorescence intensity of 21, where the fluorescence intensity is 1 before administration, and the fluorescence intensity decreased thereafter and reached 9 after 15 hours of administration.

Subsequently, the drug delivery formulation containing the TUG1-LNA oligomer was continuously intravenously administered to each of the brain tumor-orthotopically transplanted mice (i.e., mice on day 30 after transplantation of brain tumor stem cells) (administered once every 3 days (25 μg/mouse)) to evaluate the antitumor effect. Mice to which the drug delivery formulation containing a siRNA (SEQ ID NO: 54 (sense strand) and SEQ ID NO: 55 (antisense strand)) for the Firefly GL3 Luciferase gene had been administered were used for comparison analysis.

The mouse brains were excised 30 days after the initiation of administration (10 administrations in total during this period), and the brain tissues were observed by hematoxylin/eosin (HE) staining and, as a result, it was found that the tumor significantly shrank through administration of the drug delivery formulation containing the TUG1-LNA oligomer (FIG. 16), and the drug delivery formulation containing the TUG1-LNA oligomer was specifically accumulated in the brain tumor in vivo, thereby exhibiting a potent antitumor effect.

Example 8

<Suppression of Proliferation of Pancreatic Cancer Cell Line>

TUG1-LNA oligomer (LNA-modified antisense DNA, SEQ ID NO: 56) was introduced into pancreatic cancer cell lines (MIAPACA2, PANC1, BXPC3) through lipofection. The TUG1 expression level in each pancreatic cancer cell line and relative cell proliferation rate of each pancreatic cancer cell line 3 days after the introduction were measured. LNA oligomer (LNA-modified DNA, SEQ ID NO: 57) for the Firefly GL3 Luciferase gene was used as a negative control, and each expression level was represented as the relative expression of TUG1 to GAPDH as internal standard. From the results, the proliferation-suppressive effect on the pancreatic cancer cell lines due to inhibition of TUG1 was found (FIG. 17A and FIG. 17B).

Example 9

<Suppression of Tumor Proliferation in Pancreatic Cancer Cell Line (BXPC3)-Bearing Mice>

Figure 18:
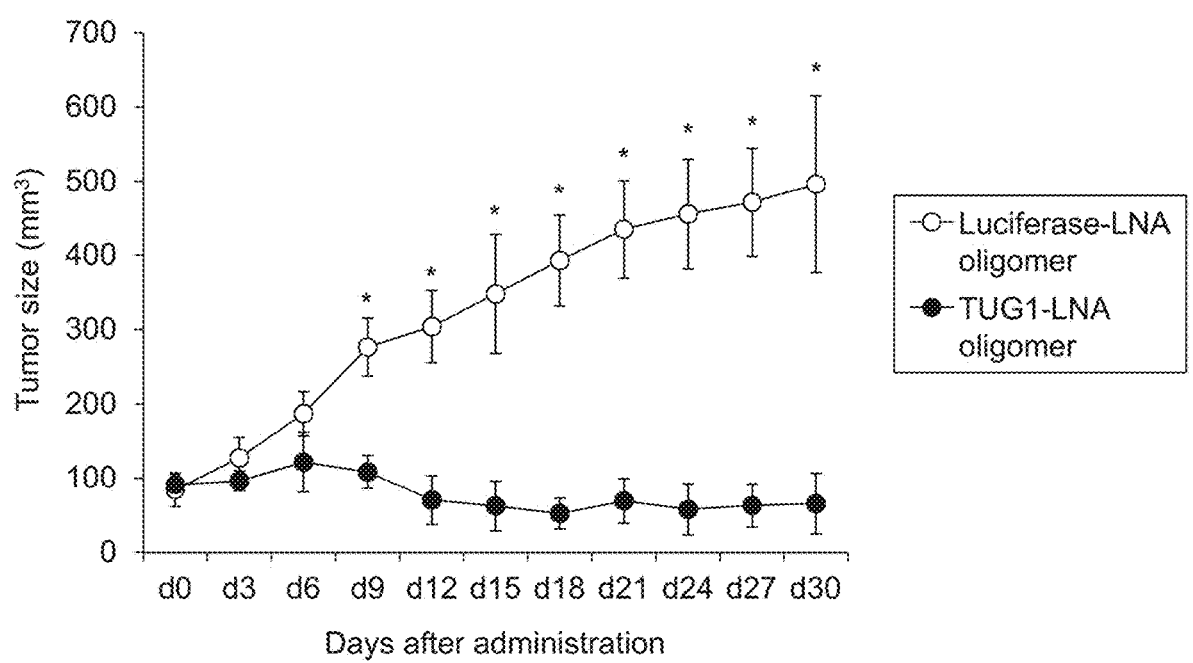
FIG. 18 illustrates the daily change of tumor size when the drug delivery formulation containing the TUG1-LNA oligomer (SEQ ID NO: 56) (i.e., the micelle-type PIC drug delivery formulation (see [Reference Example 1] below)) or the LNA oligomer (SEQ ID NO: 57) for Firefly GL3 Luciferase gene was administered intravenously and continuously to the nude mice in which the pancreatic cancer cell line (BXPC3) was transplanted subcutaneously. * indicates statistical significance (p<0.01).

The pancreatic cancer cell line (BXPC3) was subcutaneously transplanted to nude mice, and the drug delivery formulation that had incorporated TUG1-LNA oligomer (SEQ ID NO: 56) therein was continuously intravenously administered to each of the nude mice (administered once every 3 days (25 μg/mouse)) to evaluate the antitumor effect. Mice to which the drug delivery formulation encapsulating the LNA oligomer (SEQ ID NO: 57) for the Firefly GL3 Luciferase gene therein had been administered were used for comparison analysis. Each of the drug delivery formulations encapsulating different LNA oligomers therein (micelle-type PIC drug delivery formulations (see [Reference Example 1] below)) was continuously intravenously administered from day 0, which is a day when the tumor size reached approximately 100 mm³, and the tumor size was measured every 3 days until day 30. From the results as shown in FIG. 18, the tumor proliferation-suppressive effect due to use of the drug delivery formulation in which the TUG1-LNA oligomer has been incorporated was found.

Reference Example 1

<Preparation of Micelle-Type PIC Drug Delivery Formulation in which TUG1-LNA Oligomer has been Incorporated>
(1) Synthesis of Acetal-Poly(Ethylene Glycol)-Poly(L-Lysine) Block Copolymer (Acetal-PEG-PLys)

In 18 mL of N,N-dimethylformamide (DMF), 1.20 g of acetal-PEG-NH$_2$ with a mean molecular weight of 12,000 and 2.90 g of thiourea were dissolved. Then, a solution obtained by dissolving 1.34 g of N-carboxylic anhydride of Nε-trifluoroacetyl-L-lysine (Lys(TFA)-NCA, 50 equivalents with respect to acetal-PEG-NH$_2$) in 20.1 mL of DMF was added thereto, and the resultant was reacted at 20° C. for 2 days. The reaction solution was added dropwise to 600 mL of a diethyl ether-methanol (15/1) mixed solvent to yield a white precipitate. Further, a cycle consisting of dissolving the precipitate in methanol and adding the resultant dropwise into diethyl ether was repeated twice. The resulting white precipitate was collected through filtration, and vacuum-dried to afford 2.22 g of acetal-PEG-PLys (TFA).

In 200 mL of methanol, 2.00 g of the thus-obtained acetal-PEG-PLys (TFA) was dissolved, and 20 mL of 1 N sodium hydroxide aqueous solution was added thereto, and the resultant was reacted at 35° C. for 12 hours. The reaction solution was put in a dialysis tube (manufactured by Funakoshi Co., Ltd., Spectra/Por, molecular weight cut-off: 6,000 to 8,000), and dialysis was performed four times with 10 mM phosphate buffer solution (pH 7.4) containing 150 mM NaCl as an external solution, and subsequently three times with pure water as an external solution. The inner solution of the dialysis membrane was taken out, and freeze-dried to afford 1.63 g of acetal-PEG-PLys as a white solid. The compound obtained was confirmed to be the intended product by $^1$H-NMR. The polymerization degree of the polylysine segment of the acetal-PEG-PLys obtained was 45.
(2) Synthesis of cRGD-PEG-PLys In 1 mL of 10 mM phosphate buffer solution (pH 7.4), 26.2 mg (5 equivalents with respect to acetal-PEG-PLys) of cRGD peptide (formula (10)) was dissolved. Then, 5 mg (1 equivalent with respect to the cRGD peptide) of dithiothreitol (DTT) was added thereto, and the resultant was stirred at 25° C. for 30 minutes to reduce the cRGD peptide. In another container, 125 mg (1 equivalent) of the acetal-PEG-PLys obtained in the synthesis example (1) above was dissolved in 0.01 M hydrochloric acid (pH 2.0), and the resultant was stirred at 25° C. for 2 hours. Thereafter, the reduced cRGD peptide solution was added dropwise to the acetal-PEG-PLys solution, and the pH was adjusted to 5.0 with 0.05 M sodium hydroxide solution. The reaction was performed at 4° C. with stirring overnight. The reaction solution was transferred in a dialysis tube (manufactured by Funakoshi Co., Ltd., Spectra/Por, molecular weight cut-off: 6,000 to 8,000), and dialysis was performed with 10 mM phosphate buffer solution (pH 7.4) containing 150 mM NaCl for 2 days, and subsequently with distilled water for 2 days. After the dialysis, the resultant was treated with a filter (Nihon Millipore K.K., Sterivex™ GP 0.22 μm), and then freeze-dried to afford cRGD-PEG-PLys in the form of white powder (yield: 112 mg, % yield: 86%). The amount of cRGD peptide bonding to PEG-PLys was calculated from an integration ratio between the phenyl CH protein peak of the cRGD peptide and the CH$_2$ main chain peak of the PEG as measured by $^1$H-NMR. The cRGD introduction percentage of the cRGD-PEG-PLys obtained was 85%.

(3) Synthesis of cRGD-PEG-PLys (DTBP/IM) (Block Copolymer)

In 0.1 M borax buffer solution (pH 9.0), 50 mg of the cRGD-PEG-PLys obtained in (2) above was dissolved. In another container, 3.6 mg (0.1 equivalents with respect to the lysine unit of the cRGD-PEG-PLys) of 3,3'-dithiobispropionimidate (DTBP) was dissolved in cold water. The DTBP solution was added dropwise to the cRGD-PEG-PLys solution, and the resultant was stirred at 25° C. for 45 minutes. Thereafter, 38 mg (2.4 equivalents with respect to the lysine unit of the cRGD-PEG-PLys) of 2-iminothiolane (2-IM) in the form of powder was added, as it is, thereto, and the resultant was stirred at 25° C. for 30 minutes. The reaction solution was warmed to 35° C., and stirred overnight. The reaction solution was transferred in a dialysis tube (manufactured by Funakoshi Co., Ltd., Spectra/Por, molecular weight cut-off: 6,000 to 8,000), and dialysis was performed with 150 mM NaCl solution in 10 mM phosphate buffer solution (pH 7.4) for 1 hour. Then, 35 mg (2.0 equivalents with respect to the lysine unit of the cRGD-PEG-PLys) of DTT was added to the inner solution of the dialysis tube, and the dialysis tube was left to stand for 30 minutes. Thereafter, dialysis was performed with 150 mM NaCl solution for 1 hour, and with distilled water for 1 hour. After the dialysis, the resultant was treated with a filter (Nihon Millipore K.K., Sterivex™ GP 0.22 μm), and then freeze-dried to afford cRGD-PEG-PLys (DTBP/IM) in the form of white powder (yield: 56 mg). The amounts of DTBP and IM bonding to PEG-PLys (DTBP/IM) were calculated from integration percentages using the CH$_2$ peak of the DTBP, the CH$_2$ peak of the IM, and the CH$_2$ main chain peak of the PEG. The DTBP introduction and IM introduction percentages of the cRGD-PEG-PLys (DTBP/IM) obtained were 16% and 80%, respectively.

The structure of the cRGD-PEG-PLys (DTBP/IM) is as follows (formula (13)).

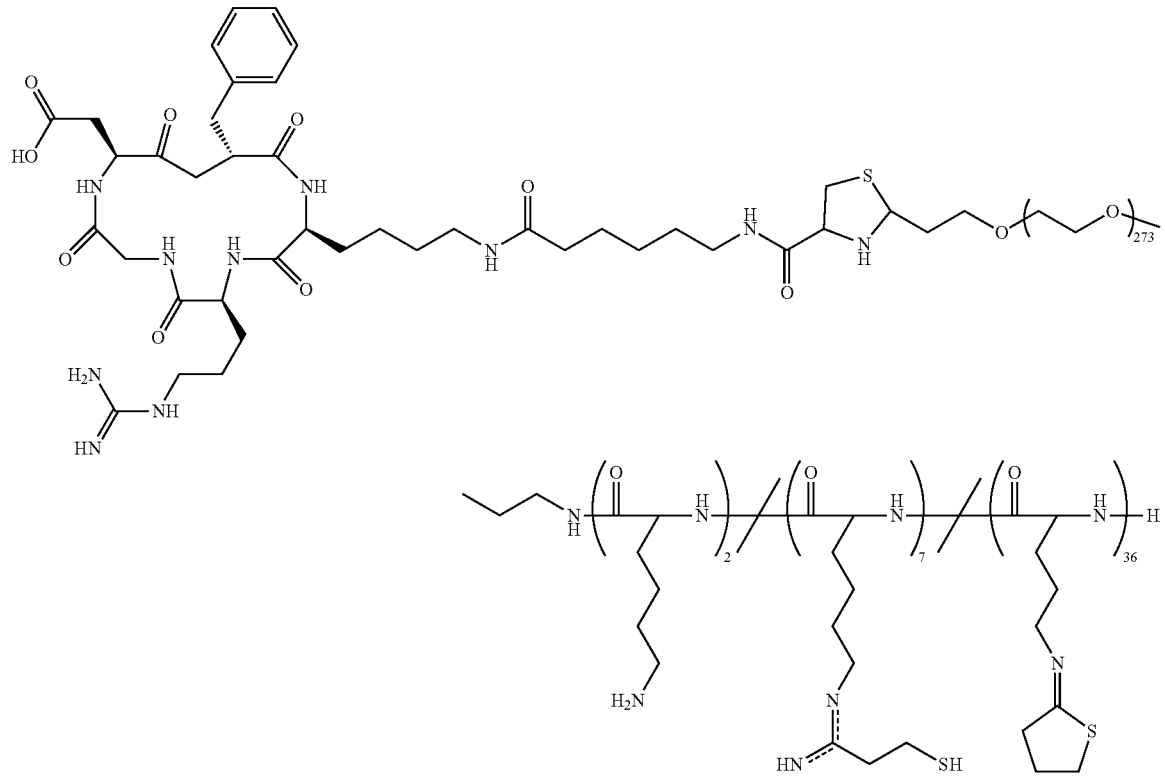

(4) Preparation of Micelle-Type PIC Drug Delivery Formulation

The cRGD-PEG-PLys (DTBP/IM) obtained in (3) above was dissolved in 10 mM HEPES buffer solution (pH 7.4) to a concentration of 5 mg/mL. Then, the resultant was mixed with 10 mM HEPES buffer solution (pH 7.4) having DTT (30.54 mg/mL), and the concentration was adjusted to give an N/P ratio of from 1 to 8, and the resultant was left to stand at room temperature for 30 minutes. The above TUG1-LNA oligomer was dissolved in 10 mM HEPES buffer solution (pH 7.4) to prepare 15 μM oligomer solution. The TUG1-LNA oligomer solution and the cRGD-PEG-PLys (DTBP/IM) solution were mixed together to give an N/P ratio of 1.3 (volume ratio, 2:1), and the resultant was left to stand at 25° C. for 24 hours. By using a Slide-A-Lyzer cassette (molecular weight cut-off: 3.5 kDa), the resulting solution was dialyzed with 10 mM HEPES solution (pH 7.4) containing 5 v/v % DMSO for 2 days, and with 10 mM HEPES solution (pH 7.4) for 2 days to afford oligomer-incorporating micelles that are complexes of a block copolymer and the TUG1-LNA oligomer solution.

The micelles obtained were used to confirm the antitumor effect through intravenous administration to tumor-transplanted mice, as described in Example 7 and Example 9.

INDUSTRIAL APPLICABILITY

The present inventors prepared modified siRNAs and modified antisense RNAs to effectively suppress the expression of TUG1 in tumor cells, and, among them, found nucleic acids that suppress the TUG1 expression and the cell proliferation of tumors such as gliomas and tumor stem cells, and, in particular, confirmed that the use of LNA-modified antisense RNAs suppresses the TUG1 expression in tumors for a longer period of time and significantly enables suppression of the tumor proliferation (JP Patent Application No. 2015-024713 (WO2016/129633A1)).

In the present application, the drug delivery formulation comprising the nucleic acid to inhibit the expression of TUG1 was further prepared, and the drug delivery formulation was administered to a subject having a tumor or cancer, such as brain tumor or pancreatic cancer. As a result, the drug delivery formulation was specifically accumulated in a tumor and exhibited a potent antitumor effect not only on tumor cells but also on tumor stem cells. Accordingly, the present invention demonstrates that the TUG1 targeting nucleic acid drug is effective for treatment of cancers such as brain tumor (for example, GBM) and pancreatic cancer.

SEQUENCE LISTING FREE TEXT

SEQ ID NOs: 4 to 19: siRNA for human TUG1,
SEQ ID NOs: 20 to 21, 28 to 29, 43, 49: siRNA for human TUG1, wherein (1) . . . (17) is RNA.
SEQ ID NOs: 22 to 27, 30 to 35, 39 to 42, 44 to 48, 50: siRNA for human TUG1, wherein (1) . . . (19) is RNA.
SEQ ID NOs: 36: LNA-modified antisense RNA, wherein (1) . . . (4) and (16) . . . (19) are locked nucleic acids.
SEQ ID NO: 37: LNA-modified antisense RNA, wherein (1) . . . (3) and (17) . . . (19) are locked nucleic acids. (19) is a locked nucleic acid.
SEQ ID NO: 38: LNA-modified antisense RNA, wherein (1) . . . (4) and (17) . . . (19) are locked nucleic acids.
SEQ ID NO: 51: LNA-modified antisense RNA, wherein (1) . . . (4) and (18) . . . (21) are locked nucleic acids.
SEQ ID NO: 52: LNA-modified antisense RNA, wherein (1) . . . (3) and (19) . . . (21) are locked nucleic acids.
SEQ ID NO: 53: LNA-modified antisense RNA, wherein (1) . . . (4) and (19) . . . (21) are locked nucleic acids.
SEQ ID NOs: 54 to 55: siRNA for Firefly GL3 Luciferase gene.
SEQ ID NO: 56: LNA-modified antisense DNA, wherein (1) . . . (4) and (19) . . . (21) are locked nucleic acids.
SEQ ID NO: 57: LNA-modified DNA for Firefly GL3 Luciferase gene, wherein (1) . . . (4) and (19) . . . (21) are locked nucleic acids.
SEQ ID NO: 58: cyclic peptide comprising Arg Gly Asp
SEQ ID NO: 59: cyclic peptide comprising Asn Gly Arg The contents disclosed in all patents, patent applications and publications cited herein are incorporated herein by reference in their entirety.

The invention claimed is:

1. An antitumor drug delivery formulation for treating a subject having a tumor selected from the group consisting of glioma, pancreatic cancer, breast cancer, colorectal cancer, prostate cancer, liver cancer, lung cancer, leukemia, and lymphoma, the tumor having tumor cells expressing a higher level of TUG1 gene as compared to the corresponding normal tissues, or for preventing the subject from tumor metastasis, comprising a polymeric micelle comprising an antisense oligonucleotide that suppresses expression of the TUG1 gene as an active ingredient;

wherein the polymeric micelle comprises a block copolymer having a cationic poly(amino acid) segment and a hydrophilic polymer chain segment and the antisense oligonucleotide, and wherein the antisense oligonucleotide is bound to a cationic group of the cationic poly(amino acid) segment to form a complex and/or the antisense oligonucleotide is incorporated in the micelle; and the antisense oligonucleotide comprises RNA, DNA, or a combination thereof and targets a TUG1 nucleotide sequence selected from the group consisting of the nucleotide sequences of nucleotide numbers 3015 to 3035 and 3394 to 3412 in the nucleotide sequence of SEQ ID NO: 3.

2. The drug delivery formulation according to claim 1, wherein the tumor is glioma or pancreatic cancer.

3. The drug delivery formulation according to claim 1, wherein the antisense oligonucleotide comprises two or more modified nucleotides at each end.

4. The drug delivery formulation according to claim 1, wherein the antisense oligonucleotide comprises at least two LNA modified nucleotides that have a 2'-O, 4'-C methylene bridge.

5. The drug delivery formulation according to claim 1, wherein the antisense oligonucleotide is an LNA-modified DNA consisting of any of the nucleotide sequences of SEQ ID NOs:51 (wherein uracil (U) is thymine (T)), 52 (wherein uracil (U) is thymine (T)), and SEQ ID NO:56.

6. The drug delivery formulation according to claim 1, wherein the hydrophilic polymer chain segment comprises a plurality of branched polymer chains.

7. The drug delivery formulation according to claim 1, wherein the cationic poly(amino acid) segment comprises polylysine or poly(ornithine).

8. The drug delivery formulation according to claim 1, wherein the hydrophilic polymer chain segment comprises poly(ethylene glycol), an end-modified poly(ethylene glycol), or branched poly(ethylene glycol) chains.

9. The drug delivery formulation according to claim 1, wherein the block copolymer comprises a linking group between the cationic poly(amino acid) segment and the hydrophilic polymer chain segment.

10. The drug delivery formulation according to claim 1, wherein the hydrophilic polymer chain segment comprises a cyclic peptide comprising the sequence of arginine-glycine-aspartic acid (SEQ ID NO: 58) or the sequence of asparagine-glycine-arginine (SEQ ID NO: 59).

11. The drug delivery formulation according to claim 1, wherein the block copolymer has an N/P ratio of more than 1, the N/P ratio being defined as [total number of cationic groups in block copolymer (N)]/[total number of phosphate groups in nucleic acid (P)].

12. The drug delivery formulation according to claim 11, wherein the N/P ratio is 2 or more.

13. The drug delivery formulation according to claim 1, wherein the antisense oligonucleotide is a modified antisense oligonucleotide.

14. The drug delivery formulation according to claim 13, wherein the modified antisense oligonucleotide comprises at least one modification selected from the group consisting of: substitution of the phosphodiester linkages with phosphorothioate, phosphorodithioate, alkylphosphonate, or phosphoramidate linkages; and substitution of 2'-position of the sugar with halogen, alkyl, alkoxy, O-alkylenyl-O-alkyl, or O—($CH_2$)$_2$—O—N($R_m$)($R_n$) where $R_m$ and $R_n$ independently represent H or a substituted or unsubstituted $C_1$-$C_{10}$ alkyl; 2'-deoxyribonucleotide; locked nucleic acid (LNA) selected from 2'-O,4'-C methylene bridge (—O—$CH_2$—)-modified nucleotide and 2'-O,4'-C ethylene bridge (—O—$CH_2CH_2$-)-modified nucleotide; and 2'-methoxyethyl nucleotide, 2'-methoxyethoxy (2'-MOE) nucleotide, 2'-methoxy (2'-OMe) nucleotide, and 2'-deoxy-2'-chloro nucleotide.

15. The drug delivery formulation according to claim 1, wherein the glioma is glioblastoma multiforme (GBM).

16. The drug delivery formulation according to claim 5, the antisense oligonucleotide further comprises a substitution of phosphodiester linkages with phosphorothioate linkages.

17. A method for treating a subject having a tumor or for preventing the subject from tumor metastasis, comprising administering to the subject the drug delivery formulation according to claim 1.

* * * * *

```
                         SEQUENCE LISTING

<160> NUMBER OF SEQ ID NOS: 59

<210> SEQ ID NO 1
<211> LENGTH: 7598
<212> TYPE: RNA
<213> ORGANISM: Homo sapiens

<400> SEQUENCE: 1
uccugcuuuc cugacccucu ccgccauuua aagaaacagu accggggcg  ggccgagcga      60 cgcagccggg acgguagcug cggugcggac cggaggagcc aucuugucuc gucgccgggg    120
agucaggccc cuaaaucgaa gaagcccugg cgcgcccucc cccccucccg ggucgguag     180 ggcgaaggaa cgggcgugcg gucgaucgag cgaucgguug gcggcucuuu cuccugcucu    240
ggcauccagc ucuuggggcg caggcccggc cgccgcggcg cgcgcccggu ggccguuggc    300
gcucgcgccg cgucuuucuu cucguacgca gaacucgggc ggcggccuau gcguuugcga    360
uucgacgagg agucguccgg guggucgcg gcggcgggca gcugcuccgc cccgcuccgg     420
gggaggcggc ggcggcagcg gccgcgggau uuggagcggc cggggaggcg gggguggccg    480
gggccggcuu ggaggccugg cgccacccuu cggggccugc aaggacccag uuggggggc     540 aggaggggc cggaggaugg uugguugugg gauuucuacu uugccuuuuc cuccuuaugc     600
cgccuuagug aggggcggga gcucuggcgg cagccccggg gugggggagac gagcuccgga   660 gucggaagag cugggguuuc uuccgggccu agccaccagu uggcggagug accuuaggcg    720
agucacucug uaauuugucu gcgccucagu uuccuccucu gccuaucaau gugugugggg    780
uugaaaucgc uuuguaaacu auaaagcgug gguguacgua aaggauggu auuguuuaua    840 auuuuuuug aguuguaaga aaacuuagca guuccccaau ccuugggguuu ugaaccuggg    900 aaccuuggau uggaguuggg gauccccaaa cuuccugaaa uugugggaau gugcgguuug    960
ggggaaugau gggaauuugu gggaaugugc guuuuagggg aaugaugauc caucgcuagc   1020
aaguuuucca aggggcugu gacccagaag aguuaagaau cacaauuucu ucaugcuaca    1080
```

```
gagaggaaac ugaggccuag augucauuug ggacccuuca caaccauuuu gaagcccugu    1140
uugagucccu gggauaugug agcuguuucu augcauaaug gauauucggg guuaacaaca    1200 gucccccugcu uggcuucuau ucugaauccu uuucuuucac caugggggugc cugaagggug   1260 gcugaugcau augguacaau ggcacccagu guaaagcagc acaauuagg aguggaugug     1320 uucuguagca uccuauuuaa auaagccuau uuuauccuuu ggcccgucaa cucuguuauc    1380
ugcugcuugu acuggugccu guacuuuucu gacucucauu gaccauauuc cacgaccaug    1440
guugucaucc auuacuugau ccuacuuuac augucuaggc ugugugguug guggugaaua    1500
ggcuucuuuu uacauggugc ugccagccca gcuaauuaau ggugcacgug gacuuuuagc    1560
aagcgggcuc acuggaagag acugaaccug gcauggaauu ccgaagaug uuuggggvuu    1620 uuuucuuucu uaaucgaaag uuaacauugu cugaaaaguu uuguuagaac acugcggaa    1680 ccucaaaauc aguagauuug gaagugauuc aaagcuaaac uuuuuccuug gcccuccuug    1740
uguucuaauu gcuugcaagu guaauacuag gauguccaag augccaguuu ugcuucuuu    1800 guuaguuguc agcugcuuuu aucaaauuuc aggccauuau ccaacaaaca cuauaaaaau    1860
guuugaacaa uuggauuuca aacauuuucg uuuuguggag uggugcucac caagugguac    1920
agcccuaagc aagugaacac aaacacauuu aagugauauu ugucugauua gauguuagcc    1980
aguuaugcua uuucauucaa augcugaaa aaaucaauug acauuccccu uuccuaaag    2040 ggcagagaca gauaaucuca cuuccagaga aaugacuugg agaaaaaaaa guguuggucu    2100
uuuugcucuu uuguaauuaa auccggaugu accaaaaag acuuaagacu ggggugauaa    2160
gaugcuuucc ucagcagaaa ggagggaaa aaaaacaacug gaaucaaag cuugaaauuc    2220 uguggcaaaa caugagaugu ccaggauugg aguugaaaaa gauuucacua caguguucug    2280
caauaguugg agcagauaac uuucagugua gccacagcca uggacuccag auuccagau    2340 uuucaagacc uggaccugga acccgaaaga gcuugucacg augcggcagg aacacuggag    2400
guagauuuuu uuuuauuuuu gaauuuuggg acuugugacc uugcugugag aaaagagaca    2460
acgacugagc aagcacuacc accagcacgu uuacugggaa uuagaagacc ugaguuucug    2520
uccagacccu cagugcaaac ugaggaugcu ccauccaaag ugaauuauga uagcagacuc    2580
cuugaaagca gggguccuugu uuagugcauc uuugcccaca uacaccacaa cauaucaaga    2640
ugcauuuauu aggaaggagg aguuuagaga gcaggcuauc agaauaacca cucaccuaca    2700
gaccugguac cuggauuuuu gcccgagaug auuccuacca ccuuacuacu gacgaagaca    2760
cccauuccag uggaccacug ugacccagga ggcauucagc caucaugaug uggccuuuac    2820
cuccacuccu gucuuguucu acccagauuc agcacagccc uuuauaguga agucagaguc    2880
cucaagccaa auagcuaaag cuguuuuauc acaacaaagg ccuaguuugu ccaugagug    2940 ugcauuucau uucuucaguu aaagccuuca gagacacaca auaaauuugg accaggggau    3000
uuuuuaguua uuaaugcucu cugaagaaag gcaacaucuu uuugagagca gcauggacc    3060 acaccccaca aucucaaaug auugaaauuc augaacaucu aggaucccgu gaaggucacu    3120 ggaccccuguu uuuucuacuu caaauccugu aguagccuac ugaaugagaa aacauauucu    3180
gacccauugg gaucaaauca aaggcacagu gaacccuca uagcaucuuc uuuggaauua    3240
cucaggaacc agaacuuuuu acacaaaugu aagaaauucu accaaggagu ccccuuaccu    3300
aacagcaucu cacaaggcug caccagauuc cagaaaaggc uucucuugau acaucaaggu    3360
agaaccucua ugcauuuugu gaccgacuua uucuuagauc auugguuuuc caaaggcuuu    3420
```

```
guggccauga agcccuuuga gugaaaacug ugcagaagcc cagaguaaaa gugaagcugc    3480
ucuggaugaa guagugaagc aagaguaggg gccugaaucc ugcuacaacu aucuuccuuu    3540
accaccgugg ugacaccuaa ggggacuucc uuacaacacc uugaacucuu ccgaacacag    3600
uuugaaaacc acugcccag acagcaauau guuugaccug aauggcauuc caaucuuuuc     3660
uguaccucca cucagcacag uucauguuca guagaugcug aacauucuua gaaauacugu    3720
gugugaacuu agaaaagugc aagaagacag gcaugucuuu gaccccagga augaucauuu    3780
gcugaagaug gugucaagug aaccuagauu aacagcccuc cacuccagau ggauauccag    3840
ugauuccuag aaugggauau agccagaaa caauucuaug cacccuacac ugacagacuc     3900
ccuuaagcaa caccagaugc ucuacuggua cuugaaguac augacuuuga agucuugacc    3960
cuccaugaau accugaauua ucagcaagcg gguuuugaag cuggugccuc auugaggcca    4020
uauuagagca acuugacau uugaccucuu guuaucagcc augguacucu acuucgugug     4080
caagagauaa cuaugaaagc caaauucaaa uacuggcaac auuuccuaaa ggggcucaau    4140
aucuaucauu cgucuucuuu uccaaacuac acaucacugu ugacucaac caguagcagu     4200 uauauugccc cuugguuuuu auucaguuua acuacuguuu ccaagauaaa ugagcuaaua    4260
agcuuuaaaa aaaaaaaaa aaaaggcuga auucuuuuuu cuucaucacu ggcauaucug     4320
ccuauucucc agaauuauua ugcuauuca gcucacuuua acaguugaac uucaagcgac     4380
aaucuuugaa caccccuucu caugugauuu aaaaugaaac cauuuggaaa aguuucuucu    4440
agccaguaau agauuuuuuu uuuaauugcu cugccuugug ccgagagaug uucuuuuaag    4500
augaaucuuu ugaugucuga uaccaccaaa uauaggguggu agggagaguu ggaggcuggc   4560
ccuuugagca ggccauuagc uuacuugcug ggcauuuccg auagcuuauu gccuaccuuu    4620
uugcuggaaa caaacugauu ugaaaaacaa aaucuaugaa gacugcagcu aaggauuuua    4680
ucgguagacu uaagagcuuu ugccuugug gauauuuuag uggaaccaca ucagucucaa     4740
uacugucauu uuacacugac ucagagcagc ugacuucauu ccuugccaug auauauauuu    4800
aaggcaggca uuguaacaga cauaaagaca acuuaucugu uucagcagga aggauucagu    4860
uuaugaacuc ucagaccaga ucauguugaa caaggagacu uugaugugug ucaugagaaa    4920
acucauucuu uacuucccag ucaauuuaaa ggccagcuau ccugagcuac ucgaaugaau    4980
gcacugguua aacauuggaa auaguuuguu uauauccuug ucucucucua ggccaauugu    5040
gauuacauga cucgacucua caucucguca aacaaggccu aggucugguu gcuguagacu    5100
gcucgcccuc aacaaauaaa aucggguuga cuagccuccu uguauauaca acuauuauuu    5160
guuaagaaga aauuaucguc aauuuucuac uaccuuccaa uugucagcuc uuuuuuuccu    5220
cucugguuuu uccuauacuu uacagaaaaa gacauugauc uauacugcca uucccucuaa    5280
uccugccaua cucagucaaa aggaaugacu uaagaugaag augaucaucu gcucgagucu    5340
aaaauauaca uuguauauaa gaauggguga uuagaaaagc aaaaaaccua aaacuuaaau    5400
cuaggagucu guauacuguc uccaugucuc caugccucag aucucaucua aaucuuugaa    5460
cagcaccauu caaccaaucu gaggccuuga cuugcuugua agaugauucu cagagaucgg    5520
cugaguuaaa aaagaugacg acuugauuac caaagaaagu agggccaacu uugacaaauc    5580
uggcucugcu gacccugu ca cucccagaug uagcauagac uccuaaacag aaccucaagu    5640
cugauugagg auaaggccuu ucccugagcu gaaaguucuu uggcagauga gcaagaaacu    5700
gaaagcugau guaccugacu ggcucuguaa gaucagaaaa cuguaccag aauaagcccu     5760 auggauuaac cccugaguac ccagaguaaa aacuaauuua cagaacuucc uuauugaucu    5820
```

-continued

```
gcugguucuu ccagaucaua uucuggcuau ugguauggcu ggccuuucug aagguacccu    5880
gcuugucuau uuuccugacu cagcucuugc cugccuuuuu cacauguugc ugcaauuaga    5940
cucaccguga ggacuacagu caauuucagu cuaucuugug cccaauacaa caaggauuuu    6000
uaauaguaac aacccacacc ucacccacua ggacucaaug uucacaacag gaaggaccau    6060
ugcugcauac uccuugacca gcaacuuuuu ugaagauauu uuuaagugca gaguaggccu    6120 cuauccugu auguaauugu cauuuucag caccuggaac cucaucuauc gggucuggaa    6180
ggaauacagc aguucgaaag ccgcguccau uucucuccuu caguagugca gaaaugaguc    6240
cgauucacca guacacacag aacuguacca guucaaccua gcaaagaag aaaaguuucc     6300 acuguacuua aaauuuacag cugacucaaa uugccucaca gaauuauuug auguagaagg    6360
cuaguugucu uacuucagau cagcaggaca guugggcucu cagacucaug accacugagu    6420
uugcuugugu ugaaacugug guuucaucca acauaugcua uuggacauga uuauuauucc    6480
auucaaaugg auuacagacu ucuugaggac aggacaaacu uaucucucau gguguuuuu     6540 uagaauacuu uuauaaccaa ggaagaaacc augccagcug uuaccauuca acuucuuaag    6600
cagagauuaa gcuuuucau aucguucucu uccuggaca ucaguaguuu uuaauugccc     6660
agcauccguu ccaucuugua caacucccu gauguuucuu aaaaccaccu cuuccuauuu    6720
ucagucugug guuggacag ucugacccaa ccuugagcuu ugggugaa cauguaauuc       6780 agaccucauc aaucagcaaa uccaucugaa cuguggagga gaagcucucu uuacugaggg    6840
ugcuuuagcu uuguaggaug aaaaccucaa acuaacaggg ccuaccaugu agagaaugaa    6900
gccagugcag gggaaagcag agccaaaaua uggagagacu ugaauccuga ugacagcguu    6960 ugugcocccug gauccaaccg ugccugaagc uagaauaucc ccuggacuuu ucaguuaugu    7020
gaaccaauaa auacccuuuu uugcuuaagu acuuugagu uggguuucug uuacuugaaa    7080
uugaauccac acuaauauau cuaccaacau ugagacuuga cagauccaag uauuuauuaa    7140
gcuagagguc auggucacug aaauuacuuu ccaaagugga agacaaaaug aaacaggaac    7200 ugagggaauua uuuaagaucc cacagaagcg uaaaaaugac auguagaaa guaauagaaa     7260 accuaaaugu cugucauuaa aggauagguu aaggugugu ucagccauau aggaauaucu      7320
cguaucuguu aaaaugaaua aaguacauuc auuguguaug gaaaaauggc caugauacau    7380
uaggugaaac aaguuauuaa uagaaaagug uacaguguga acucauuuua aaaugugugu    7440
gcuuauguuu auaaaugcau agaaaggucu auucacagcu uucuuugaac aguguagauc    7500
acaugaaacu uucaacuuua uacauuucug uauuaauauu uuacuacc cacauuauuu       7560 uuaaacuuua uuuuaaauaa agaauuuuua aaauuaaa                             7598
```

<210> SEQ ID NO 2
<211> LENGTH: 7528
<212> TYPE: RNA
<213> ORGANISM: Homo sapiens

<400> SEQUENCE: 2

```
uccugcuuuc cugacccucu ccgccauuua agaaacagu accggggcg ggccgagcga         60 cgcagccggg acgguagcug cggugcggac cggaggagcc aucuugucuc gucgccgggg      120
agucaggccc cuaaaucgaa gaagcccugg cgcgcccucc cccccucccg ggucugguag      180
ggcgaaggaa cgggcgugcg gucgaucgag cgaucgguug gcggcucuuu cuccugcucu     240
ggcauccagc ucuuggggcg caggcccggc cgccgcggcg cgcgcccggu ggccguuggc      300
```

```
gcucgcgccg cgucuuucuu cucguacgca gaacucgggc ggcggccuau gcguuugcga    360
uucgacgagg agucguccgg guggucggcg gcggcgggca gcugcuccgc cccgcuccgg    420
gggaggcggc ggcggcagcg gccgcgggau uggagcggc cggggaggcg ggggguggccg    480 gggccggcuu ggaggccugg cgccacccuu cggggccugc aaggacccag uuggggggc    540 aggaggggc cggaggaugg uugguugugg gauuucuacu uugccuuuuc cuccuuaugc    600
cgccuuagug aggggcggga gcucggcgg cagccccggg guggggagac gagcuccgga    660
gucggaagag cugggauuuc uuccgggccu agccaccagu uggcggagug accuuaggcg    720
agucacucug uaauuugucu cgccucagu uccuccucu gccuaucaau gugugugggg    780
uugaaaucgc uuuguaaacu auaaagcgug ggguacgua aaggaugguu auuguuuaua    840 auuuuuuug aguuguaaga aaacuuagca guuccccaau ccuuggguuu ugaaccuggg    900
aaccuuggau uggaguuggg gauccccaaa cuuccugaaa uugugggaau gugcgguuug    960
ggggaaugau gggaauuugu gggaauugugc guuuuagggg aaugaugauc caucgcuagc   1020
aaguuuucca aggggcugu gacccagaag aguuaagaau cacaauuucu ucaugcauaca    1080 gagaggaaac ugaggccuag augucauuug ggacccuuca caaccauuuu gaagcccugu    1140
uugagucccu gggauaugug agcuguuucu augcauaaug gauauucggg guuaacaaca    1200 gucccccugcu uggcuucuau ucgaauccu uuucuucac caugggggc cugaagggug     1260 gcugaugcau auggucacaau ggcacccagu guaaagcagc ucaauuagg aguggaugug    1320 uucuguagca uccauuuuaa auaagccuau uuuauccuuu ggcccgucaa cucuguuauc    1380 ugcugccuugu acuggugccu guacuuuucu gacucucauu gaccauauuc cacgaccaug    1440
guugucaucc auuacuugau ccuacuuuac augucuaggc ugugugguug guggugaaua    1500
ggcuucuuuu uacauggugc ugccagccca gcuaauuaau ggugcacgug gacuuuuagc    1560
aagcgggcuc acuggaagag acugaaccug gcauggaauu ccgaagaug uuuggggnuu    1620 uuucuuucu uaaucgaaag uuaacauugu cgaaaaguu uuguuagaac uacugcggaa     1680
ccucaaaauc aguagauuug gaagugauuc aaagcuaaac uuuuuccuug gcccuccuug    1740
uguucuaauu gcuugcaagu guaauacuag gaugucacaag augccaguuu uugcuucuuu    1800
guuaguuguc agcugcuuuu aucaaauuuc aggccauuau ccaacaaaca cuauaaaaau    1860 guugaacaa uuggauuuca aacauuuucg uuuuguggag uggugcucac caagugguac    1920
agcccuaagc aagugaacac aaacacauuu aagguauuu ugucugauua gauguuagcc    1980
aguuaugcua uuucauucaa auguucugaaa aaaucaauug acuauuccccu uuuccuaaag    2040 ggcagagaca gauaaucuca cuuccagaga aaugacuugg agaaaaaaaa guguuggucu    2100
uuuugcucuu uuguaauuaa auccggaugu accucaaaag acuuaagacu guggugauaa    2160
gaugcuuucc ucagcagaaa ggagggaaaa aaaacaacug gaacucaaag cuugaaauuc    2220
uguggcaaaa caugaugu ccaggauugg agguugaaaa gauuucacua cagguuucug      2280
caauaguugg agcagauaac uuucagugua gccacagcca uggacuccag auuuccagau    2340
uuucaagacc uggaccugga acccgaaaga gcuugucacg augcggcagg aacacuggag    2400 guagauuuu uuuuauuuu gaauuuuggg acguugugacc uugcugugag aaaagagaca    2460
acgacugagc aagcacuacc accagcacug uuacgggaa uuagaagacc ugaguuucug     2520
uccagacccu cagugcaaac ugaggaugcu ccauccaaag ugaauuaugu ccugugccuc    2580
cugauugcug aguguucacc uggaccucu gacuaccuuc ccugugcuau ccaucagcc      2640 uacagaccug guaccuggau uuuugcccga gaugauuccu accaccuuac uacugacgaa    2700
```

```
gacacccauu ccaguggacc acugugaccc aggaggcauu cagccaucau gauguggccu    2760
uuaccuccac uccugucuug uucuacccag auucagcaca gcccuuuaua gugaagucag    2820
aguccucaag ccaaauagcu aaagcuguuu uaucacaaca aaggccuagu uguuccaug     2880 agugugcauu ucauucuuc aguuaaagcc uucagagaca cacaauaaau uggaccagg      2940 ggauuuuuua guuauuaaug cucucugaag aaaggcaaca ucuuuugag agcagcauug     3000 gaccacaccc cacaaucuca aaugauugaa auucaugaac aucuaggauc ccgugaaggu    3060
cacuggaccc uguuuuucu acuucaaauc cuguaguagc cuacugaaug agaaaacaua     3120
uucugaccca uugggaucaa aucaaaggca cagugaacuc cucauagcau cuucuuugga   3180
auuacucagg aaccagaacu uuuuacacaa auguaagaaa uucuaccaag gaguccccuu    3240
accuaacagc aucucacaag gcugcaccag auuccagaaa aggcuucucu ugauacauca    3300
agcauuuugu gaccgacuua uucuuagauc auugguuuuc caaaggcuuu uggccauga    3360 agcccuuuga gugaaaacug ugcagaagcc cagaguaaaa gugaagcugc ucuggaugaa    3420
guagugaagc aagaguaggg gccugaaucc ugcuacaacu aucuuccuuu accaccgugg    3480
ugacaccuaa ggggacuucc uuacaacacc uugaacucuu ccgaacacag uuugaaaacc    3540
acugccccag acagcaauau guuugaccug aauggcauuc caaucuuuuc uguaccucca    3600
cucagcacag uucauguuca guagaugcug aacauucuua gaaauacugu gugugaacuu    3660
agaaaagugc aagaagacag gcaugucuuu gaccccagga augaucauuu gcugaagaug    3720
gugucaagug aaccuagauu aacagcccuc cacuccagau ggauauccag ugauuccuag    3780
aaugggauau agccagagaa caauucuaug caccccuacac ugacagacuc ccuuaagcaa   3840
caccagaugc ucuacuggua cuugaaguac augacuuuga agucuugacc cuccaugaau    3900
accugaauua ucagcaagcg gguuuugaag cuggugccuc auugaggcca uauuagagca    3960
acuuguacau uugaccucuu guuaucagcc augguacucu acuucgugug caagagauaa    4020
cuaugaaagc caaauucaaa uacuggcaac auuuccuaaa ggggcucaau aucuaucauu    4080
cgucuucuuu uccaaacuac acaucacugu augacucaac caguagcagu uauauugccc    4140
cuuggguuuu auucaguuua acuacuguuu ccaagauaaa ugagcuaaua agcuuuaaaa    4200
aaaaaaaaaa aaaaggcuga auucuuuuuu cuucaucacu ggcauaucug ccauucucc    4260 agaauuauua ugacuauuca gcucacuuua acaguugaac uucaagcgac aaucuuugaa    4320
caccccuucu caugugauuu aaaaugaaac cauuuggaaa aguucuucu agccaguaau     4380 agauuuuuuu uuuaauugcu cugccuugug ccgagaaug uucuuuuaag augaaucuuu     4440
ugaugucuga uaccaccaaa uauaggugu agggagaguu ggaggcuggc ccuuugagca     4500
ggccauuagc uuacuugcug ggcauuuccg auagcuauu gccaccuuu uugcggaaa       4560 caaacugauu ugaaaacaa aaucuaugaa gacugcagcu aaggauuuua ucgguagacu    4620
uaagagcuuu ugccuugug gauauuuag uggaaccaca ucagucucaa uacgucauu      4680 uuacacugac ucagagcagc ugacuucauu ccuugccaug auauauauuu aaggcaggca    4740
uuguaacaga cauaaagaca acuuaucugu ucagcaggaa aggauucagu uuaugaacuc    4800
ucagaccaga ucauguugaa caaggagacu uugaugugu caugagaaa acucauucuu      4860 uacuucccag ucaauuuaaa ggccagcuau ccugagcuac ucgaaugaau gcacugguua    4920
aacauuggaa auaguuuguu uauaccuug ucucucucua ggccaauugu gauuacauga    4980
cucgacucua caucucguca aacaaggccu aggucugguu gcuguagacu gcucgcccuc    5040
```

```
aacaaauaaa aucggugga cuagccuccu uguauauaca acauuauuu guuaagaaga    5100 aauuaucguc aauuuucuac uaccuuccaa uugucagcuc uuuuuuuccu cucugguuuu    5160
uccuauacuu uacagaaaaa gacauugauc uauacugcca uucccucuaa uccugccaua    5220
cucagucaaa aggaaugacu uaagaugaag augaucaucu gcucgagucu aaaauauaca    5280
uuguauauaa gaauuggauga uuagaaaagc aaaaaaccua aaacuuaaau cuaggagucu    5340
guauacuguc uccaugucuc caugccucag aucucaucua aaucuuugaa cagcaccauu    5400
caaccaaucu gaggccuuga cuugcuugua agaugauucu cagagaucgg cugaguuaaa    5460
aaagaugacg acuugauuac caaagaaagu agggccaacu uugacaaauc uggcucugcu    5520
gacccuguca cucccagaug uagcauagac uccuaaacag aaccucaagu cugauugagg    5580
auaaggccuu uccugagcu gaaaguucuu uggcagauga gcaagaaacu gaaagcugau    5640
guaccugacu ggcucuguaa gaucagaaaa cuguauccag aauaagcccu auggauuaac    5700
cccugaguac ccagaguaaa aacuaauuua cagaacuucc uuauugaucu gcugguucuu    5760
ccagaucaua uucggcuau ugguauggcu ggccuuucg aagguacccu gcuugucuau    5820 uuuccgacu cagcucuugc cugccuuuuu cacauguugc ugcaauuaga cucaccguga    5880
ggacuacagu caauuucagu cuacuugug cccaauacaa caaggauuuu uaauaguaac    5940
aacccacacc ucacccacua ggacucaaug uucacaacag gaaggaccau ugcugcauac    6000
uccuugacca gcaacuuuuu ugaagauauu uuuaagugca gaguaggccu cuauuccugu    6060
auguaauugu caugucag caccuggaac cucaucuauc gggucuggaa ggaauacagc    6120
aguucgaaag ccgcguccau uucucuccuu cagaguagca gaaaugaguc cgauuccacca    6180 guacacacag aacuguacca guucaaccua gcaaagaag aaaaguuucc acuguacuua    6240
aaauuuacag cugacucaaa uugccucaca gaauuauuug auguagaagg cuaguugucu    6300
uacuucagau cagcaggaca guugggcucu cagacucaug accacugagu ugcuugugu    6360 ugaaacugug guucauccca acauaugcua ugggacauga uuauuaucc auucaaaugg    6420 auuacagacu ucuugaggac aggacaaacu uaucucucau gguguuuuu uagaauacuu    6480 uuauaaccaa ggaagaaacc augccagcug uuaccauuca acuucuuaag cagagauuaa    6540 gcuuuucau aucguucuu auccuggaca ucaguaguuu uuaauugccc agcauccguu    6600
ccaucuugua acaacccccu gauguuucuu aaaaccaccu cuuccuauuu ucagucugug    6660 guuggacag ucugacccaa ccuugagcuu uguggugaa cauguaauuc agaccucauc    6720
aaucagcaaa uccaucugaa cuguggagga gaagcucucu uuacgagg ugcuuuagcu    6780 uuguaggaug aaaccucaa acuaacaggg ccuaccaugu agagaaugaa gccagugcag    6840
gggaaagcag agccaaaaua uggagagacu ugaauccuga ugacagcguu ugugcccccug    6900 gauccaaccg ugccugaagc uagaauaucc ccuggacuuu ucaguuaugu gaaccaauaa    6960
auacccuuuu uugcuuuagu uacuuugagu uggguucug uuacuugaaa uugaaccac    7020 acuaauauau cuaccaacau ugagacuuga cagaccaag uauuuauuaa gcuagagguc    7080
auggucacug aaauuacuuu ccaaagugga agacaaaaug aaacaggaac ugagggaaua    7140
uuuaagaucc cacagaagcg uaaaaaugac augguagaaa guauagaaaa accuaaaugu    7200
cugucauuaa aggauaggu aaggguggu ucagccauau aggaauaucu cguaucuguu    7260
aaaaugaaua aaguacauuc auuguguaug gaaaaauggc caugauacau uaggugaaac    7320 aaguauuaa uagaaagug uacaguguga acucauuuua aaaugugugu gcuuauguu    7380 auaaaugcau agaaaggucu auucacagcu uucuuugaac aguguagauc acaugaaacu    7440
```

| | |
|---|---:|
| uucaacuuua uacauuucug uauuaauauu uuacacuacc cacauuauuu uuaaacuuua | 7500 |
| uuuuaaauaa agaauuuuua aaauuaaa | 7528 |

<210> SEQ ID NO 3
<211> LENGTH: 7542
<212> TYPE: RNA
<213> ORGANISM: Homo sapiens

<400> SEQUENCE: 3

| | |
|---|---:|
| uccugcuuuc cugacccucu ccgccauuua aagaaacagu accgggggcg ggccgagcga | 60 |
| cgcagccggg acgguagcug cggugcggac cggaggagcc aucugucuc ucgccgggg | 120 |
| agucaggccc cuaaaucgaa gaagcccugg cgcgcccucc ccccucccg ggucugguag | 180 |
| ggcgaaggaa cgggcgugcg gucgaucgag cgaucgguug gcggcucuuu uccugcucu | 240 |
| ggcauccagc ucuuggggcg caggcccggc cgccgcggcg cgcgcccggu ggccguuggc | 300 |
| gcucgcgccg cgucuuucuu cucguacgca gaacucgggc ggcggccuau gcguuugcga | 360 |
| uucgacgagg agucguccgg guggucggcg gcggcgggca gcugcuccgc cccgcuccgg | 420 |
| gggaggcggc ggcggcagcg gccgcgggau uggagcggc cggggaggcg ggguggccg | 480 |
| gggccggcuu ggaggccugg cgccacccuu cggggccugc aaggacccag uuggggggc | 540 |
| aggaggggc cggaggaugg uugguugugg gauuucuacu uugccuuuuc ucccuuaugc | 600 |
| cgccuuagug agggcggga gcucuggcgg cagccccggg guggggagac gagcuccgga | 660 |
| gucggaagag cuggguuuuc uuccggggccu agccaccagu uggcggagug accuuaggcg | 720 |
| agucacucug uaauuugucu gcgccucagu uuccuccucu gccuaucaau guguguggg | 780 |
| uugaaaucgc uuuguaaacu auaaagcgug gguguacgua aaggaugguu auuguuuaua | 840 |
| auuuuuuug aguguaaga aaacuuagca guuccccaau ccuugggu ugaaccuggg | 900 |
| aaccuuggau uggaguuggg gauccccaaa cuuccgaaa uuguggaau ugcgguuug | 960 |
| gggaaugau gggaauuugu gggaugugc guuuagggg aaugaugauc caucgcuagc | 1020 |
| aaguuuucca aggggcugu gacccagaag aguuaagaau cacaauuucu ucaugcuaca | 1080 |
| gagaggaaac ugaggccuag augucauuug ggacccuuca caaccauuuu gaagcccugu | 1140 |
| uugagucccu gggauaugug agcuguuucu augcauaaug gauauucggg guuacaaca | 1200 |
| gucccccugcu uggcuucuau ucugaauccu uucuuucac caugggguc cugaaggug | 1260 |
| gcugaugcau augguacaau ggcacccagu guaaagcagc uacaauuagg aguggaugug | 1320 |
| uucuguagca uccauuuaa auaagccuau uuuauccuuu ggcccgucaa cucguuauc | 1380 |
| ugcugcuugu acuggugccu guacuuuucu gacucucauu gaccauauuc cacgaccaug | 1440 |
| guugucaucc auuacuugau ccuacuuuac augucuaggc uguguggug guggugaaua | 1500 |
| ggcuucuuuu uacauggugc ugccagccca gcuaauuaau ggugcacgug gacuuuagc | 1560 |
| aagcgggcuc acuggaagag acugaaccug gcauggaauu ccgaagaug uuggggguuu | 1620 |
| uuuucuuucu uaaucgaaag uuaacauugu cugaaaaguu uguuagaac uacugcggaa | 1680 |
| ccucaaaauc aguagauuug gaagugauuc aaagcuaaac uuuuuccuug gcccuccuug | 1740 |
| uguucuaauu gcugcaagu guauacuag gaugccaag augccaguuu uugcuucuuu | 1800 |
| guuaguuguc agcugcuuuu aucaaauuuc aggccauuau ccaacaaaca cuauaaaaau | 1860 |
| guuugaacaa uuggauuuca aacauuuucg uuuuguggag uggugcucac caagguguac | 1920 |
| agcccuaagc aagugaacac aaacacauuu aagguauuu ugcugauua gauguuagcc | 1980 |

```
aguuaugcua uuucauucaa augucugaaa aaaucaauug acuauucccu uuccuaaag    2040 ggcagagaca gauaaucuca cuuccagaga aaugacuugg agaaaaaaaa guguuggucu    2100
uuuugcucuu uuguaauuaa auccggaugu accucaaaag acuuaagacu guggugauaa    2160
gaugcuuucc ucagcagaaa ggagggaaaa aaaacaacug gaacucaaag cuugaaauuc    2220
ugggcaaaaa caugagaugu ccaggauugg agguugaaaa gauuucacua caguguucug    2280
caauaguugg agcagauaac uucagugua gccacagcca uggacuccag auuccagau     2340 uuucaagacc uggaccugga acccgaaaga gcuugucacg augcggcagg aacacuggag    2400
guagauuuuu uuuuauuuuu gaauuuuggg acuguugacc uugcugugag aaaagagaca    2460
acgacugagc aagcacuacc accagcacug uuacugggaa uuagaagacc ugaguuucug    2520
uccagacccu cagugcaaac ugaggaugcu ccauccaaag ugaauuaugu ccugugccuc    2580
cugauugcug aguguucacc uggaccuucu gacuaccuuc ccugugcuau uccaucagcc    2640
uacagaccug guaccuggau uuugcccga gaugauuccu accaccuuac uacugacgaa     2700
gacacccauu ccaguggacc acugugaccc aggaggcauu cagccaucau gaugugggccu    2760 uuaccuccac uccugucuug uucuaccag auucagcaca gcccuuuaua gugaagucag    2820
aguccucaag ccaaauagcu aaagcuguuu uaucacaaca aaggcuagu uuguuccaug    2880 agugugcauu ucauucuuc aguuaaagcc uucagagaca cacaauaaau uggaccagg     2940 ggauuuuuua guuauuaaug cucucugaag aaaggcaaca ucuuuugag agcagcauug    3000 gaccacaccc cacaaucuca aaugauugaa auucaugaac aucuaggauc ccgugaaggu    3060
cacuggaccc uguuuuucu acuucaaauc cuguagaugc cuacugaaug agaaaacaua    3120
uucugaccca uggggaucaa aucaaaggca cagugaacuc cucauagcau cuucuuugga    3180
auuacucagg aaccagaacu uuuacacaa auguaagaaa uucuaccaag gaguccccuu     3240 accaacagc aucucacaag gcugcaccag auuccagaaa aggcuucucu ugauacauca     3300
agguagaacc ucuaugcauu uugugaccga cuuauucuua gaucauuggu uuccaaagg    3360 cuuugugcc augaagcccu ugagugaaa acugugcaga agcccagagu aaaagugaag    3420
cugcucugga ugaaguagug aagcaagagu agggccuga auccgcuac aacuaucuuc     3480 cuuuaccacc guggugacac cuaagggac uuccuuacaa caccuugaac ucuuccgaac    3540
acaguuugaa aaccacugcc ccagacagca auauguuuga ccugaauggc auuccaaucu    3600
uuucuguacc uccacucagc acaguucaug uucaguagau gcugaacauu cuuagaaaua    3660 cguguguga acuugaaaaa gugcaagaag acaggcaugu cuuugacccc aggaaugauc    3720
auuugcugaa gaugguguca agugaaccua gauuaacagc ccuccacucc agauggauau    3780
ccagugauuc cuagaaugg auauagccag agaacaauuc uaugcacccu acacugacag    3840 acuccccuuaa gcaacaccag augcucuacu gguacuugaa gacaugacu uugaagucuu    3900 gacccuccau gaauaccuga auuaucagca agcggguuuu gaagcugguug ccucauugag    3960 gccauauuag agcaacuugu acauuugacc ucuuguuauc agccauggua ucucuacuucg    4020 ugugcaagag auaacuauga aagccaaauu caaauacugg caacauuucc uaaaggggcu    4080
caauaucuau cauucgucuu cuuuuccaaa cuacacauca cuguaugacu caaccaguag    4140
caguuauauu gccccuuggu uuuauucag uuuaacuacu guuccaaga uaaaugagcu     4200 aauaagcuuu aaaaaaaaaa aaaaaaaagg cugaauucuu uuucuucau cacuggcaua    4260 ucugccuauu cuccagaauu auuaugacua uucagcucac uuuaacaguu gaacuucaag    4320
cgacaaucuu ugaacacccc uucucaugug auuuaaaaug aaaccauuug gaaaaguuuc    4380
```

```
uucuagccag uaauagauuu uuuuuuuaau ugcucugccu ugugccgaga gauguucuuu    4440
uaagaugaau cuuuugaugu cugauaccac caaauauagg ugguagggag aguuggaggc    4500
uggcccuuug agcaggccau uagcuuacuu gcugggcauu uccgauagcu uauugccuac    4560
cuuuuugcug gaaacaaacu gauuugaaaa acaaaaucua ugaagacugc agcuaaggau    4620
uuuaucggua gacuuaagag cuuuugnccu uguggauauu uuagnggaac cacaucaguc    4680
ucaauacugu cauuuuacac ugacucagag cagcugacuu cauuccuugc caugauauau    4740
auuuaaggca ggcauuguaa cagacauaaa gacaacuuau cuguuucagc aggaaggauu    4800
caguuuauga acucucagac cagaucaugu ugaacaagga gacuuugaug ugugucauga    4860
gaaaacucau ucuuuacuuc ccagucaauu uaaaggccag cuaccugag cuacucgaau     4920 gaaugcacug guuaaacauu ggaaauaguu uguuuauauc cuugucucuc ucuaggccaa    4980
uugugauuac augacucgac ucuacaucuc gucaaacaag gccuaggucu gguugcugua    5040
gacugcucgc cccuaacaaa uaaaaucugg uugacuagcc uccuuguaua uacaacuauu    5100
auuuguuaag aagaaauuau cgucaauuuu cuacuaccuu ccaauuguca gcucuuuuuu    5160
uccucucugg uuuuuccuau acuuuacaga aaaagacauu gaucuauacu gccauuccou    5220 cuaauccugc cauacucagu caaaaggaau gacuuaagau gaagaugauc aucugcucga    5280
gucuaaaaua uacauuguau auaagaauug ugauuagaa aagcaaaaaa ccuaaaacuu     5340
aaaucuagga gucuguauac ugucuccaug ucuccaugcc ucagaucuca ucuaaaucuu    5400
ugaacagcac cauucaacca aucugaggcc uugacuugcu uguaagauga uucucagaga    5460
ucggcugagu uaaaaagau gacgacuuga uuaccaaaga aguagggcc aacuuugaca      5520 aaucuggcuc ugcugacccu gucacuccca gauguagcau agacuccuaa acagaaccuc    5580
aagucugauu gaggauaagg ccuucuccug agcugaaagu ucuuuggcag augagcaaga    5640
aacugaaagc ugauguaccu gacuggcucu guaagaucag aaaacuguau ccagaauaag    5700
cccuauggau uaaccccuga guacccagag uaaaaacuaa uuuacagaac uuccuuauug    5760
aucugcuggu ucuuccagau cauauucugg cuauugguau ggcuggccuu ucugaaggua    5820
cccugcuugu cuauuuuccu gacucagcuc uugccugccu uuuucacaug uugcugcaau    5880
uagacucacc gugaggacua cagcaauuu cagucuaucu ugugcccaau acaacaagga     5940
uuuuuaauag uaacaaccca caccucaccc acuaggacuc aauguucaca acaggaagga    6000
ccauugcugc auacuccuug accagcaacu uuuuugaaga uauuuuaag ugcagaguag     6060 gcccucuauuc cuguauguaa uuguucauuu ucagcaccug gaaccucauc uaucgggucu    6120
ggaaggaaua cagcaguucg aaagccgcgu ccauucucu ccuucaguag ugcagaaaug     6180
aguccgauuc accaguacac acagaacugu accaguucaa ccuagcaaaa gaagaaaagu    6240 uccacugua cuuaaaauuu acagcugacu caaauugccu cacagaauua uuugauguag     6300
aaggcuaguu gucuuacuuc agaucagcag gacaguuggg cucucagacu caugaccacu    6360
gaguuugcuu guguugaaac cugguuuuca uccaacauau gcauuggac augauuauua     6420 uuccauucaa auggauuaca gacuucuuga ggacaggaca aacuuaucuc ucaugugguu    6480
uuuuuagaau acuuuuauaa ccaaggaaga aaccaugcca gcguuuacca uucaacuucu    6540
uaagcagaga uuaagcuuuu ucauaucugu ucuuauccug gacaucagua guuuuuaauu    6600
gcccagcauc cguccaucu uguaacaacu cccugauguu ucuuaaaacc accucuuccu     6660
auuuucaguc gugguuugg acagucugac ccaaccuuga gcuuugnggg ugaacaugua     6720
```

-continued

```
auucagaccu caucaaucag caaauccauc ugaacugugg aggagaagcu cucuuuacug    6780
agggugcuuu agcuuuguag gaugaaaacc ucaaacuaac agggccuacc auguagagaa    6840
ugaagccagu gcaggggaaa gcagagccaa aauauggaga gacuugaauc cugaugacag    6900
cguuugugcc ccuggaucca accgugccug aagcuagaau aucccccugga cuuuucaguu   6960 augugaaccu auaaauaccc uuuuuugcuu aaguuacuuu gaguuggguu ucuguuacuu    7020
gaaauugaau ccacacuaau auaucuacca acauugagac uugacagauc caaguauuua    7080
uuaagcuaga ggucaugguc acugaaauua cuuuccaaag uggaagacaa aaugaaacag    7140
gaacugaggg aauauuuaag aucccacaga agcguaaaaa ugacaugguua gaaaguaaua   7200 gaaaaccuaa augucuguca uuaaaggaua gguuaaggug ugguucagcc auauaggaau    7260
aucucguauc uguuaaaaug aauaaaguac auucauugug uauggaaaaa uggccaugau    7320
acauuaggug aaacaaguua uuaauagaaa aguacagu gugaacucau uuuaaaaugu     7380
gugugcuuau guuuauaaau gcauagaaag gucuauucac agcuuucuuu gaacagugua    7440
gaucacauga aacuuucaac uuuauacauu ucuguauua uauuuuacac uacccacauu     7500
auuuuuaaac uuuauuuuaa auaaagaauu uuuaaaauua aa                        7542
```

```
<210> SEQ ID NO 4
<211> LENGTH: 19
<212> TYPE: RNA
<213> ORGANISM: Artificial
<220> FEATURE:
<223> OTHER INFORMATION: siRNA for human TUG1

<400> SEQUENCE: 4
ccagaagagu uaagaauca                                                   19

<210> SEQ ID NO 5
<211> LENGTH: 19
<212> TYPE: RNA
<213> ORGANISM: Artificial
<220> FEATURE:
<223> OTHER INFORMATION: siRNA for human TUG1

<400> SEQUENCE: 5
gugcagaagc ccagaguaa                                                   19

<210> SEQ ID NO 6
<211> LENGTH: 21
<212> TYPE: RNA
<213> ORGANISM: Artificial
<220> FEATURE:
<223> OTHER INFORMATION: siRNA for human TUG1

<400> SEQUENCE: 6
ggauauagcc agagaacaau u                                                21

<210> SEQ ID NO 7
<211> LENGTH: 21
<212> TYPE: RNA
<213> ORGANISM: Artificial
<220> FEATURE:
<223> OTHER INFORMATION: siRNA for human TUG1

<400> SEQUENCE: 7
guuaagaaga aauuaucguc a                                                21

<210> SEQ ID NO 8
<211> LENGTH: 21
```

<212> TYPE: RNA
<213> ORGANISM: Artificial
<220> FEATURE:
<223> OTHER INFORMATION: siRNA for human TUG1

<400> SEQUENCE: 8
ggauuuuuua guuauuaaug c					21

<210> SEQ ID NO 9
<211> LENGTH: 21
<212> TYPE: RNA
<213> ORGANISM: Artificial
<220> FEATURE:
<223> OTHER INFORMATION: siRNA for human TUG1

<400> SEQUENCE: 9
cucaaaugau ugaaaucau g					21

<210> SEQ ID NO 10
<211> LENGTH: 21
<212> TYPE: RNA
<213> ORGANISM: Artificial
<220> FEATURE:
<223> OTHER INFORMATION: siRNA for human TUG1

<400> SEQUENCE: 10
ccuguuuuuu cuacuucaaa u					21

<210> SEQ ID NO 11
<211> LENGTH: 21
<212> TYPE: RNA
<213> ORGANISM: Artificial
<220> FEATURE:
<223> OTHER INFORMATION: siRNA for human TUG1

<400> SEQUENCE: 11
cacaaaugua agaaauucua c					21

<210> SEQ ID NO 12
<211> LENGTH: 19
<212> TYPE: RNA
<213> ORGANISM: Artificial
<220> FEATURE:
<223> OTHER INFORMATION: siRNA for human TUG1

<400> SEQUENCE: 12
ugauucuuaa cucuucugg					19

<210> SEQ ID NO 13
<211> LENGTH: 19
<212> TYPE: RNA
<213> ORGANISM: Artificial
<220> FEATURE:
<223> OTHER INFORMATION: siRNA for human TUG1

<400> SEQUENCE: 13
uuacucuggg cuucugcac					19

<210> SEQ ID NO 14
<211> LENGTH: 21
<212> TYPE: RNA
<213> ORGANISM: Artificial
<220> FEATURE:
<223> OTHER INFORMATION: siRNA for human TUG1

<400> SEQUENCE: 14
uuguucucug gcuauauccc a                              21

<210> SEQ ID NO 15
<211> LENGTH: 21
<212> TYPE: RNA
<213> ORGANISM: Artificial
<220> FEATURE:
<223> OTHER INFORMATION: siRNA for human TUG1

<400> SEQUENCE: 15
acgauaauuu cuucuuaaca a                              21

<210> SEQ ID NO 16
<211> LENGTH: 21
<212> TYPE: RNA
<213> ORGANISM: Artificial
<220> FEATURE:
<223> OTHER INFORMATION: siRNA for human TUG1

<400> SEQUENCE: 16
auuaauaacu aaaaauccc c                               21

<210> SEQ ID NO 17
<211> LENGTH: 21
<212> TYPE: RNA
<213> ORGANISM: Artificial
<220> FEATURE:
<223> OTHER INFORMATION: siRNA for human TUG1

<400> SEQUENCE: 17
ugaauuucaa ucauuugaga u                              21

<210> SEQ ID NO 18
<211> LENGTH: 21
<212> TYPE: RNA
<213> ORGANISM: Artificial
<220> FEATURE:
<223> OTHER INFORMATION: siRNA for human TUG1

<400> SEQUENCE: 18
uugaaguaga aaaaacaggg u                              21

<210> SEQ ID NO 19
<211> LENGTH: 21
<212> TYPE: RNA
<213> ORGANISM: Artificial
<220> FEATURE:
<223> OTHER INFORMATION: siRNA for human TUG1

<400> SEQUENCE: 19
agaauuucuu acauuugugu a                              21

<210> SEQ ID NO 20
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 20
ccagaagagu uaagaauca                                 19

<210> SEQ ID NO 21

```
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 21
gugcagaagc ccagaguaa                                                  19

<210> SEQ ID NO 22
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 22
ggauauagcc agagaacaat t                                               21

<210> SEQ ID NO 23
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 23
guuaagaaga aauuaucguc a                                               21

<210> SEQ ID NO 24
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 24
ggauuuuuua guuauuaaug c                                               21

<210> SEQ ID NO 25
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 25
cucaaaugau ugaaauucat g                                               21

<210> SEQ ID NO 26
<211> LENGTH: 21
<212> TYPE: DNA
<213> ORGANISM: Artificial
<220> FEATURE:
```

```
<223> OTHER INFORMATION: siRNA for human TUG1
<220> FEATURE:
<221> NAME/KEY: misc_RNA
<222> LOCATION: (1)..(19)

<400> SEQUENCE: 26 ccuguuuuu cuacuucaaa t                                              21

<210> SEQ ID NO 27
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 27
cacaaaugua agaaauucua c                                             21

<210> SEQ ID NO 28
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 28
ugauucuuaa cucuucugg                                                19

<210> SEQ ID NO 29
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 29
uuacucuggg cuucugcac                                                19

<210> SEQ ID NO 30
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 30
uuguucucug gcuauauccc a                                             21

<210> SEQ ID NO 31
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)
```

```
<400> SEQUENCE: 31
acgauaauuu cuucuuaaca a                                              21

<210> SEQ ID NO 32
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 32
auuaauaacu aaaaaauccc c                                              21

<210> SEQ ID NO 33
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 33
ugaauuucaa ucauuugaga t                                              21

<210> SEQ ID NO 34
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 34
uugaaguaga aaaaacaggg t                                              21

<210> SEQ ID NO 35
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 35
agaauuucuu acauuugugt a                                              21

<210> SEQ ID NO 36
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (16)..(19)
```

<223> OTHER INFORMATION: locked nucleic acid

<400> SEQUENCE: 36
uuacucuggg cuucugcac                                                    19

<210> SEQ ID NO 37
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(3)
<223> OTHER INFORMATION: locked nucleic acid
<220> FEATURE:
<221> NAME/KEY: misc_feature
<222> LOCATION: (17)..(19)
<223> OTHER INFORMATION: locked nucleic acid

<400> SEQUENCE: 37
uuacucuggg cuucugcac                                                    19

<210> SEQ ID NO 38
<211> LENGTH: 19
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (17)..(19)
<223> OTHER INFORMATION: locked nucleic acid

<400> SEQUENCE: 38
uuacucuggg cuucugcac                                                    19

<210> SEQ ID NO 39
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 39
uacuguuucu uuaaauggcg g                                                 21

<210> SEQ ID NO 40
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 40
aaaaguuuag cuuugaauca c                                                 21

<210> SEQ ID NO 41
<211> LENGTH: 21

```
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 41
auaaaugcau cuugauaugt t                                              21

<210> SEQ ID NO 42
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 42
auuaauaacu aaaaaauccc c                                              21

<210> SEQ ID NO 43
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 43
gaauaagccc uaggauta                                                  19

<210> SEQ ID NO 44
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 44
uaacuuaagc aaaaaagggt a                                              21

<210> SEQ ID NO 45
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 45
gccauuuaaa gaaacaguac c                                              21

<210> SEQ ID NO 46
<211> LENGTH: 21
<212> TYPE: DNA
<213> ORGANISM: Artificial
<220> FEATURE:
<223> OTHER INFORMATION: siRNA for human TUG1
```

```
<220> FEATURE:
<221> NAME/KEY: misc_RNA
<222> LOCATION: (1)..(19)

<400> SEQUENCE: 46
gauucaaagc uaaacuuuut c                                              21

<210> SEQ ID NO 47
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 47
cauaucaaga ugcauuuaut a                                              21

<210> SEQ ID NO 48
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 48
ggauuuuuua guuauuaaug c                                              21

<210> SEQ ID NO 49
<211> LENGTH: 19
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(17)

<400> SEQUENCE: 49
uaauccauag ggcuuautc                                                 19

<210> SEQ ID NO 50
<211> LENGTH: 21
<212> TYPE: DNA
<213> ORGANISM: Artificial
<220> FEATURE:
<223> OTHER INFORMATION: siRNA for human TUG1
<220> FEATURE:
<221> NAME/KEY: misc_RNA
<222> LOCATION: (1)..(19)

<400> SEQUENCE: 50
cccuuuuuug cuuaaguuac t                                              21

<210> SEQ ID NO 51
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
```

```
<220> FEATURE:
<221> NAME/KEY: misc_feature
<222> LOCATION: (18)..(21)
<223> OTHER INFORMATION: locked nucleic acid

<400> SEQUENCE: 51
ugaauuucaa ucauuugaga u                                              21

<210> SEQ ID NO 52
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(3)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 52
ugaauuucaa ucauuugaga u                                              21

<210> SEQ ID NO 53
<211> LENGTH: 21
<212> TYPE: RNA
<213> ORGANISM: Artificial
<220> FEATURE:
<223> OTHER INFORMATION: LNA-modified antisense RNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 53
ugaauuucaa ucauuugaga u                                              21

<210> SEQ ID NO 54
<211> LENGTH: 21
<212> TYPE: DNA
<213> ORGANISM: Artificial
<220> FEATURE:
<223> OTHER INFORMATION: siRNA for firefly GL3 luciferase
<220> FEATURE:
<221> NAME/KEY: misc_RNA
<222> LOCATION: (1)..(19)

<400> SEQUENCE: 54
cuuacgcuga guacuucgat t                                              21

<210> SEQ ID NO 55
<211> LENGTH: 21
<212> TYPE: DNA
<213> ORGANISM: Artificial
<220> FEATURE:
<223> OTHER INFORMATION: siRNA for firefly GL3 luciferase
<220> FEATURE:
<221> NAME/KEY: misc_RNA
<222> LOCATION: (1)..(19)

<400> SEQUENCE: 55
ucgaaguacu cagcguaagt t                                              21
```

```
<210> SEQ ID NO 56
<211> LENGTH: 21
<212> TYPE: DNA
<213> ORGANISM: Artificial
<220> FEATURE:
<223> OTHER INFORMATION: LNA-modified antisense DNA
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 56
tgaatttcaa tcatttgaga t                                             21

<210> SEQ ID NO 57
<211> LENGTH: 21
<212> TYPE: DNA
<213> ORGANISM: Artificial
<220> FEATURE:
<223> OTHER INFORMATION: LNA-modified DNA for firefly GL3 luciferase
<220> FEATURE:
<221> NAME/KEY: misc_feature
<222> LOCATION: (1)..(4)
<223> OTHER INFORMATION: locked nucleic acid
<220> FEATURE:
<221> NAME/KEY: misc_feature
<222> LOCATION: (19)..(21)
<223> OTHER INFORMATION: locked nucleic acid

<400> SEQUENCE: 57
tcgaagtact cagcgtaagt t                                             21

<210> SEQ ID NO 58
<211> LENGTH: 3
<212> TYPE: PRT
<213> ORGANISM: Artificial Sequence
<220> FEATURE:
<223> OTHER INFORMATION: Cyclic peptide

<400> SEQUENCE: 58

Arg Gly Asp
1

<210> SEQ ID NO 59
<211> LENGTH: 3
<212> TYPE: PRT
<213> ORGANISM: Artificial Sequence
<220> FEATURE:
<223> OTHER INFORMATION: Cyclic peptide

<400> SEQUENCE: 59

Asn Gly Arg
1
```